US009068011B2

(12) United States Patent
Neijssen et al.

(10) Patent No.: US 9,068,011 B2
(45) Date of Patent: Jun. 30, 2015

(54) MONOCLONAL ANTIBODIES AGAINST C-MET

(75) Inventors: Joost J. Neijssen, Werkhoven (NL);
Bart De Goeij, Maarssen (NL); Edward
Norbert Van Den Brink, Halfweg (NL);
Aran Frank Labrijn, Nigtevecht (NL);
Rene Hoet, Boxmeer (NL); Janine
Schuurman, Diemen (NL); Paul
Parren, Odijk (NL); Jan Van De
Winkel, Zeist (NL)

(73) Assignee: GENMAB A+S, Copenhagen (DK)

( * ) Notice: Subject to any disclaimer, the term of this
patent is extended or adjusted under 35
U.S.C. 154(b) by 95 days.

(21) Appl. No.: 13/583,743

(22) PCT Filed: Mar. 10, 2011

(86) PCT No.: PCT/EP2011/053646
§ 371 (c)(1),
(2), (4) Date: Nov. 2, 2012

(87) PCT Pub. No.: WO2011/110642
PCT Pub. Date: Sep. 15, 2011

(65) Prior Publication Data
US 2013/0216548 A1 Aug. 22, 2013

Related U.S. Application Data

(60) Provisional application No. 61/312,622, filed on Mar. 10, 2010.

(30) Foreign Application Priority Data

Mar. 10, 2010 (DK) .................. 2010 00191
Sep. 24, 2010 (DK) .................. 2010 00862

(51) Int. Cl.
C07K 16/30 (2006.01)
C07K 16/40 (2006.01)
C07K 16/28 (2006.01)
A61K 39/395 (2006.01)
A61K 45/06 (2006.01)
A61K 39/00 (2006.01)

(52) U.S. Cl.
CPC ............ *C07K 16/40* (2013.01); *A61K 2039/505*
(2013.01); *C07K 16/2863* (2013.01); *C07K
2317/21* (2013.01); *C07K 2317/53* (2013.01);
*C07K 2317/74* (2013.01); *C07K 2317/76*
(2013.01); *C07K 2317/92* (2013.01); *A61K
39/3955* (2013.01); *A61K 45/06* (2013.01)

(58) Field of Classification Search
CPC ................ C07K 16/18–16/44; C07K 2317/21;
C07K 2317/76
See application file for complete search history.

(56) References Cited

U.S. PATENT DOCUMENTS

| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,646,036 | A | 7/1997 | Schwall et al. |
| 5,661,016 | A | 8/1997 | Lonberg et al. |
| 5,686,292 | A | 11/1997 | Schwall et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 6,214,344 | B1 | 4/2001 | Schwall et al. |
| 7,498,420 | B2 | 3/2009 | Michaud et al. |
| 7,632,926 | B2 | 12/2009 | Kim et al. |
| 2005/0191293 | A1 | 9/2005 | Deshpande et al. |
| 2010/0129369 | A1 | 5/2010 | Davies et al. |
| 2014/0141000 | A1* | 5/2014 | Chiu et al. ................ 424/136.1 |

FOREIGN PATENT DOCUMENTS

| EP | 2014681 A1 | 1/2009 |
| WO | 91/09974 A1 | 7/1991 |
| WO | 92/03918 A1 | 3/1992 |
| WO | 92/05184 A1 | 4/1992 |
| WO | 92/13097 A1 | 8/1992 |
| WO | 92/22645 A1 | 12/1992 |
| WO | 93/01227 A1 | 1/1993 |
| WO | 93/15754 A1 | 8/1993 |
| WO | 94/00764 A1 | 1/1994 |
| WO | 94/06909 A2 | 3/1994 |
| WO | 94/25585 A1 | 11/1994 |
| WO | 96/38557 A1 | 12/1996 |

(Continued)

OTHER PUBLICATIONS

Paul, Fundamental Immunology, 3rd Edition, 1993, pp. 292-295.*
Muyldermans, Rev Mol Biotech 2001; 74:277-302.*
Rudikoff et al., Proc. Nat'l Acad. Sci. USA 1982; 79:1979-83.*
Brown et al., J. Immunol. 1996; 156(9):3285-91.*
Portolano et al., J. Immunol. 1993; 150:880-7.*
Tseng, Jeffrey R. et al., "Preclinical Efficacy of the c-Met Inhibitor CE-355621 in a U87 MG Mouse Xenograft Model Evaluated by 18F-FDG Small-Animal PET," J. Nucl. Med., vol. 49:129-134 (2008).
Tuaillon, Nadine et al., "Biased Utilization of DHQ52 and JH4 Gene Segments in a Human Ig Transgenic Minilocus Is Independent of Antigenic Selection," Journal of Immunology, vol. 152:2912-2920 (1994).

(Continued)

*Primary Examiner* — Sheela J Huff
*Assistant Examiner* — Jessica H Roark
(74) *Attorney, Agent, or Firm* — Nelson Mullins Riley & Scarborough LLP; Jane E. Remillard, Esq.; Christopher L. Frank

(57) ABSTRACT

Isolated monoclonal antibodies which bind to human c-Met, the hepatocyte growth factor receptor, and related antibody-based compositions and molecules, are disclosed. Pharmaceutical compositions comprising the antibodies and therapeutic and diagnostic methods for using the antibodies are also disclosed.

24 Claims, 22 Drawing Sheets

(56) References Cited

FOREIGN PATENT DOCUMENTS

| | | |
|---|---|---|
| WO | 96/40914 A1 | 12/1996 |
| WO | 98/24884 A1 | 6/1998 |
| WO | 01/09187 A2 | 2/2001 |
| WO | 01/14424 A2 | 3/2001 |
| WO | 02/02593 A2 | 1/2002 |
| WO | 02/43478 A2 | 6/2002 |
| WO | 02/102854 A2 | 12/2002 |
| WO | 02/102972 A2 | 12/2002 |
| WO | 02/102973 A2 | 12/2002 |
| WO | 03/057155 A2 | 7/2003 |
| WO | 2004/072117 A2 | 8/2004 |
| WO | 2004/108766 A2 | 12/2004 |
| WO | 2005/001486 A1 | 1/2005 |
| WO | 2005/016382 A1 | 2/2005 |
| WO | 2005/044848 A1 | 5/2005 |
| WO | 2005/058965 A1 | 6/2005 |
| WO | 2005/063816 A2 | 7/2005 |
| WO | 2006/015371 A2 | 2/2006 |
| WO | 2006/104911 A2 | 10/2006 |
| WO | 2006/105511 A1 | 10/2006 |
| WO | 2007/090807 A1 | 8/2007 |
| WO | 2007/126799 A2 | 11/2007 |
| WO | WO2007/126799 A2 * | 11/2007 |
| WO | 2008/146137 A1 | 12/2008 |
| WO | WO2008/145137 A2 * | 12/2008 |
| WO | 2009/007427 A2 | 1/2009 |
| WO | 2009/097006 A2 | 8/2009 |
| WO | 2009/142738 A2 | 11/2009 |
| WO | 2010/037835 A2 | 4/2010 |
| WO | 2010/059654 A1 | 5/2010 |
| WO | 2010/063746 A1 | 6/2010 |
| WO | 2010/064089 A1 | 6/2010 |
| WO | 2010/064090 A1 | 6/2010 |
| WO | 2010/069765 A1 | 6/2010 |

OTHER PUBLICATIONS

Van Der Horst, Edward Htun et al., "Discovery of Fully Human Anti-Met Monoclonal Antibodies with Antitumor Activity against Colon Cancer Tumor Models In Vivo," Neoplasia, vol. 11:355-364 (2009).

Baeuerle, Patrick A. et al., "BiTE: Teaching antibodies to engage T-cells for cancer therapy," Current Opinion in Molecular Therapeutics, vol. 11(1):22-30(2009).

Basilico, Cristina et al., "A High Affinity Hepatocyte Growth Factor-binding Site in the Immunoglobulin-like Region of Met," The Journal of Biological Chemistry, vol. 283(30):21267-21277 (2008).

Birchmeier, Carmen et al., "Met, Metastasis, Motility and More," Nature Reviews Molecular Cell Biology, vol. 4 (12):915-925 (2003).

Boccaccio, Carla et al., "Invasive growth: a MET-driven genetic programme for cancer and stem cells," Nature Reviews Cancer, vol. 6:637-645 (2006).

Burgess, Teresa et al., "Fully Human Monoclonal Antibodies to Hepatocyte Growth Factor with Therapeutic Potential against Hepatocyte Growth Factor/c-Met-Dependent Human Tumors," Cancer Research, vol. 66 (3):1721-1729 (2006).

Camacho, L.H. et al., "First in human phase I study of MK-2461, a small molecule inhibitor of c-Met, for patients with advanced solid tumors," Journal of Clinical Oncology, 2008 ASCO Annual Meeting Proceedings, vol. 26(155), 2 pages, Poster 14657 (2008).

Cao, Brian et al., "Neutralizing monoclonal antibodies to hepatocyte growth factor/scatter factor (HGF/SF) display antitumor activity in animal models," PNAS, vol. 98(13):7443-7448 (2001).

Cecchi, Fabiola et al., "Targeting the HGF/Met signalling pathway in cancer," European Journal of Cancer, vol. 46:1260-1270 (2010).

Chen, Jianzhu et al., "Immunoglobulin gene rearrangement in B cell deficient mice genereated by targeted deletion of the JH locus," International Immunology, vol. 5(6):647-656 (1993).

Chirgadze, Dimitri Y. et al., "Crystal structure of the NK1 fragment of HGF/SF suggests a novel mode for growth factor dimerization and receptor binding," Nature Structural Biology, vol. 6(1):72-79 (1999).

Comoglio, Paolo M. et al., "Drug development of MET inhibitors: targeting oncogene addiction and expedience," Nat. Rev. Drug Discov., vol. 7(6):504-516 (2008).

Corso, S. et al., "Silencing the MET oncogene leads to regression of experimental tumors and metastases," Oncogene, vol. 27:684-693 (2008).

Corvaia, Nathalie et al., "First bivalent fully antagonist anti-c-Met antibody targeting the c-Met receptor: I? in vitro mechanism of action," 100th AACR Annual Meeting, 2 pages, Poster 835 (2009).

Dall'Acqua, William F. et al., "Modulation of the Effector Functions of a Human IgG1 through Engineering of Its Hinge Region," The Journal of Immunology, vol. 177:1129-1138 (2006).

Dangl, Jeffrey L. et al., "Segmental flexibility and complement fixation of genetically engineered chimeric human, rabbit and mouse antibodies," The EMBO Journal, vol. 7(7):1989-1994 (1988).

Eder, Joseph Paul et al., "Novel Therapeutic Inhibitors of the c-Met Signaling Pathway in Cancer," Clin. Cancer Res., vol. 15(7):2207-2214 (2009).

Ferracini, Riccardo et al., "The Met/ HGF receptor is over-expressed in human osteosarcomas and is activated by either a paracrine or an autocrine circuit," Oncogene, vol. 10:739-749 (1995).

Fishwild, Dianne M. et al., "High-avidity human IgGk monoclonal antibodies from a novel strain of minilocus transgenic mice," Nature Biotechnology, vol. 14:845-851 (1996).

Foveau, Benedicte et al., "Down-Regulation of the Met Receptor Tyrosine Kinase by Presenilin-dependent Regulated Intramembrane Proteolysis," Molecular Biology of the Cell, vol. 20:2495-2507 (2009).

Genmab, "Better Antibodies by Design," 106 pages (2011).

Giordano, Silvia, "Rilotumumab, a mAb against human hepatocyte growth factor for the treatment of cancer," Current Opinion in Molecular Therapeutics, vol. 11(4):448-455 (2009).

Goetsch, Liliane et al., "First bivalent fully antagonist anti-c-Met antibody targeting the c-Met receptor: II—in vivo activity," 100th AACR Annual Meeting, Poster 2792, 2 pages (2009).

Goetsch, Liliane et al., "h224G11, a humanized whole antibody targeting the c-Met receptor, induces c-Met down-regulation and triggers ADCC functions," AACR 101st Annual Meeting, 1 page, Poster 2448 (2010).

Goetsch, Liliane et al., "Selection criteria for c-Met-targeted therapies: emerging evidence for biomarkers," Biomarkers Med., vol. 4(1):149-170 (2010).

Goetsch, Liliane et al., "Single or combined in vivo therapies of cancer with h224G11, a humanized antibody targeting the c-Met receptor," Molecular Cancer Therapeutics, vol. 8(12 Suppl. 1): doi: 10.1158/1535-7163.TARG-09-B127, 1 page, Poster B127 (2009).

Harding, Fiona A. et al., "Class Switching in Human Immunoglobulin Transgenic Mice," Ann. N.Y. Acad. Sci., vol. 764:536-546 (1995).

Jin, Hongkui et al., "MetMAb, the One-Armed 5D5 Anti-c-Met Antibody, Inhibits Orthotopic Pancreatic Tumor Growth and Improves Survival," Cancer Research, vol. 68(11):4360-4368 (2008).

Kakkar, Tarundeep et al., "Pharmacokinetics and Safety ofa Fully Human Hepatocyte Growth Factor Antibody, AMG 102, in Cynomolgus Monkeys," Pharmaceutical Research, vol. 24(10):1910-1918 (2007).

Kim, K. Jin et al., "Systemic Anti-Hepatocyte Growth Factor Monoclonal Antibody Therapy Induces the Regression of Intracranial Glioma Xenografts," Clin. Cancer Res., vol. 12(4):1292-1298 (2006).

Knudsen, Beatrice S. et al., "Showering c-Met-dependent cancers with drugs," Current Opinion in Genetics & Development, vol. 18:87-96 (2008).

Li, De-Quan et al., "Three Patterns of Cytokine Expression Potentially Involved in Epithelial-Fibroblast Interactions of Human Ocular Surface," Journal of Cellular Physiology, vol. 163:61-79 (1995).

Lonberg, Nils et al., "Antigen-specific human antibodies from mice comprising four distinct genetic modifications," Nature, vol. 368:856-859 (1994).

Lonberg, Nils et al., "Human Antibodies from Transgenic Mice," Intern. Rev. Immunol., vol. 13:65-93 (1995).

(56) References Cited

OTHER PUBLICATIONS

Martens, Tobias et al., "A Novel One-Armed Anti-c-Met Antibody Inhibits Glioblatoma Growth In vivo," Clin. Cancer Res., vol. 12(20):6144-6152 (2006).

Mueller, Kelly L. et al., "Met and c-Src Cooperate to Compensate for Loss of Epidermal Growth Factor Receptor Kinase Activity in Breast Cancer Cells," Cancer Res., vol. 68(9): doi:10.1158/0008-5472.CAN-08-0132, 19 pages.

Pacchiana, Giovanni et al., "Monovalency Unleashes the Full Therapeutic Potential of the DN-30 Anti-Met Antibody," J. Biol. Chem., 18 pages (2010).

Parren, Paul W.H.I., "Novel human monoclonal antibodies against c-Met," 6th European Antibody Congress, 1 page (2010).

Patnaik, A. et al., "Phase I study of SCH 900105 (SC), an anti-hepatocyte growth factor (HGF) monoclonal antibody (MAb), as a single agent and in combination with erlotinib (E) in patients (pts) with advanced solid tumors," J. Clin. Oncol., vol. 28(15s), 2 pages, Poster 2525 (2010).

Peruzzi, Benedetta et al., "Targeting the c-Met Signaling Pathway in Cancer," Clin. Cancer Res., vol. 12 (12):3657-3660 (2006).

Petrelli, Annalisa et al., "Ab-induced ectodomain shedding mediates hepatocyte growth factor receptor down-regulation and hampers biological activity." PNAS, vol. 103(13):5090-5095 (2006).

Prat, Maria et al., "Agonistic monoclonal antibodies against the Met receptor dissect the biological responses to HGF," Journal of Cell Science, vol. 111:237-247 (1998).

Raum, Tobias J. et al., "Novel Primate-crossreactive BiTE Antibodies that Eliminate Cancer Cells Expressing cMet, IGF-1R, FAP-alpha, PSCA, ENdosialin, CA IX or Her2/neu," AACR, 1 page, Poster 2434 (2010).

Salgia, R. et al., "A phase I, open-label, dose-escalation study of the safety and pharmacology of MetMAb, a monoclonal antagonist antibody to the receptor c-Met, administered IV in patients with locally advanced or metastatic solid tumors," 20th Annual AACR-NCI-EORTC International Conference: Molecular Targets and Cancer Therapeutics, p. 129, Poster 411 (2008).

Saphire, Erica Ollmann et al., "Contrasting IgG Structures Reveal Extreme Asymmetry and Flexibility," J. Mol. Biol., vol. 319:9-18 (2002).

Schmidt, Laura et al., "Germline and somatic mutations in the tyrosine kinase domain of the MET proto-oncogene in papillary renal carcinomas," Nature Genetics, vol. 16:68-73 (1997).

Spigel, D.R. et al., "Final efficacy results from OAM4558g, a randomized phase II study evaluating MetMAb or placebo in combination with erlotinib in advanced NCSLC," J. Clin. Oncol., vol. 29: 2 pages, Poster 7505 (2011).

Tam, Eric et al., "Targeted disruption of the hepatocyte growth factor beta-chain/Met interface inhibits HGF-dependent Met signaling," 98th AACR Annual Meeting, Poster 2524, 2 pages (2007).

Taylor, Lisa D. et al., "A transgenic mouse that expresses a diversity of human sequence heavy and light chain immunoglobulins," Nucleic Acids Research, vol. 20(23):6287-6295 (1992).

Taylor, Lisa D. et al., "Human immunoglobulin transgenes undergo rearrangement, somatic mutation and class switching in mice that lack endogenous IgM," International Immunology, vol. 6(4):579-591 (1994).

Tetreault, Jonathan et al., "Gastric cancer cell lines with c-Met gene amplification are sensitive to growth inhibition by the bivalent c-Met antibody LA480," Proceedings: AACR 101st Annual Meeting, Cancer Research, vol. 70(8 Suppl. 1): doi: 10.1158/1538-7445.AM10-2430, 1 page, Poster 2430 (2010).

Lonberg, N., "Transgenic Approaches to Human Monoclonal Antibodies," The Pharmacology of Monoclonal Antibodies, M. Rosenberg (Ed.), Springer-Verlag, Berlin, Chapter 3, pp. 49-101 (1994).

\* cited by examiner

Figure 1

VH Comparison 1:
```
IgHV1-18-1   QVQLVQSGAEVKKPGASVKVSCKASGYTFTSYGISWVRQAPGQGLEWMGWISAYNGNTNYAQ
VH1016-181   QVQLVQSGAEVKKPGASVKVSCKASGYTFTSYGISWVRQAPGQGLEWMGWISAYNGYTNYAQ
VH1016-066   QVQLVQSGAEVKKPGASVKVSCEASGYTFTSYGISWVRQAPGHGLEWMGWISAYNGYTNYAQ
VH1016-065   QVQLVQSGAEVKKPGASVKVSCEASGYTFTNYGISWVRQAPGHGLEWMGWISAYNGYTNYAQ
VH1016-069   QVQLVQSGAEVKKPGASVKVSCESSGYTFTSYGISWVRQAPGHGLEWMGWISAYNGYTNYAQ
VH1016-082   QVQLVQSGAEVKKPGASVKVSCESSGYTFTSYGISWVRQAPGHGLEWMGWISAYNGYTNYAQ
VH1016-089   QVQLVQSGAEVKKPGASVKVSCESSGYTFTSYGISWVRQAPGHGLEWMGWISAYNGYTNYAQ
Consensus    QVQLVQSGAEVKKPGASVKVSCEASGYTFTSYGISWVRQAPGHGLEWMGWISAYNGYTNYAQ IgHV1-18-1   KLQGRVTMTTDTSTSTAYMELRSLRSDDTAVYYCAR---------------------
VH1016-181   KLQGRVTMTTDTSTSTAYMELRSLRSDDTAVYYCARDLRGTNYFDYWGQGTLVTVSS
VH1016-066   KLQGRVTMTTDTSTSTAYMELRSLRSDDTAVYYCARDLRGTNYFDYWGQGTLVTVSS
VH1016-065   KLQGRVTMTTDTSTSTAYMELRSLRSDDTAVYYCARDLRGTNYFDYWGQGTLVTVSS
VH1016-069   KLQGRVTMTTDTSTSTAYMELRSLRSDDTAVYYCARDLRGTNYFDYWGQGTLVTVSS
VH1016-082   KLQGRVTMTTDTSTSTAYMELRSLRSDDTAVYYCARDLRGTNYFDYWGQGTLVTVSS
VH1016-089   KLQGRVTMTTDTSTSTAYMELRSLRSDDTAVYYCARDLRGTNYFDYWGQGTLVTVSS
Consensus    KLQGRVTMTTDTSTSTAYMELRSLRSDDTAVYYCARDLRGTNYFDYWGQGTLVTVSS
```

VH Comparison 2:
```
IgHV1-69-4   QVQLVQSGAEVKKPGSSVKVSCKASGGTFSSYAISWVRQAPGQGLEWMGRIIPILGIANYAQ
VH1016-005   QVQLVQSGAEVKKPGSSVKVSCKASGGTFSSYGIGWVRQAPGQGLEWMGRIIPILGIANYAQ
VH1016-031   QVQLVQSGAEVKKPGSSVKVSCKASGGTFSSYGIGWVRQAPGQGLEWMGRIIPILGIANYAQ
VH1016-006   QVQLVQSGAEVKKPGSSVKVSCKASGGTFSSIGIGWVRQAPGQGLEWMGRIEPILGTANYAQ
VH1016-007   QVQLVQSGAEVKKPGSSVKVSCKASGGTFSSYGIGWVRQAPGQGLEWMGRIEPILGTANYAQ
VH1016-011   QVQLVQSGAEVKKPGSSVKVSCKASGGTFSSYGIGWVRQAPGQGLEWMGRIFPILGTANYAQ
Consensus    QVQLVQSGAEVKKPGSSVKVSCKASGGTFSSYGIGWVRQAPGQGLEWMGRIEPILGTANYAQ IgHV1-69-4   MFQGRVTITADKSTSTAYMELSSLRSEDTAVYYCAR-----------------------
VH1016-005   MFQGRVTITADKSTSTAYMELSSLRSEDTAVYYCARDVGYDMRDIFDIWGQGTMVAVSS
VH1016-031   MFQGRVTITADKSTSTAYMELSSLRSEDTAVYYCARDVGYDMRDIFDIWGQGTMVAVSS
VH1016-006   MFQGRVTITADKSTSTAYMELGLRSEDTAVYYCARDVGYDSADAFDIWGQGTMVTVSS
VH1016-007   MFQGRVTITADKSTSTAYMELSSLRSEDTAVYYCARDVGYDSADAFDIWGQGTMVTVSS
VH1016-011   MFQGRVTITADKSTSTAYMELSSLRSEDTAVYYCARDVGYDSADAFDIWGQGTMVTVSS
Consensus    MFQGRVTITADKSTSTAYMELSSLRSEDTAVYYCARDVGYDSADAFDIWGQGTMVTVSS
```

VH Comparison 3:
```
IgHV3-30-3-1 QVQLVESGGGVVQPGRSLRLSCAASGFTFSSYAMHWVRQAPGKGLEWVAVISYDGSNKYYAD
VH1016-017   QVQLVESGGGVVQPGRSLRLSCAASGFTFSSYAMHWVRQAPGKGLEWVAVISYDGSNKYYAD
VH1016-025   QVQLVESGGGVVQPGRSLRLSCAASGFTFSSYAMHWVRQAPGKGLEWVAVISYDGSNKYYAD
VH1016-022   QVQLVESGGGVVQPGRSLRLSCAASGFTFSSYAMHWVRQAPGKGLEWVAVISYDGSNKYYAD
Consensus    QVQLVESGGGVVQPGRSLRLSCAASGFTFSSYAMHWVRQAPGKGLEWVAVISYDGSNKYYAD IgHV3-30-3-1 SVKGRFTISRDNSKNTLYLQMNSLRAEDTAVYYCAR-----------------------
VH1016-017   SVKGRFTISRDNSKNTLYLQMNSLRAEDTAVYYCARELLWFGELWGYFDLWGRGTLVTVSS
VH1016-025   SVKGRFTISRDNSKNTLYLQMNSLRAEDTAVYYCARELLWFGELWGYFDLWGRGTLVTVSS
VH1016-022   SVKGRFTISRDNSKNTLYLQMNSLRAEDTAVYYCARELLWFGELWGYFDLWGRGTLVTVSS
Consensus    SVKGRFTISRDNSKNTLYLQMNSLRAEDTAVYYCARELLWFGELWGYFDLWGRGTLVTVSS
```

VH Comparison 4:
```
IgHV3-23-1   EVQLLESGGGLVQPGGSLRLSCAASGFTFSSYAMSWVRQAPGKGLEWVSAISGSGGITYYAD
VH1016-040   EVQLLESGGGLVQPGGSLRLSCAASGFTFSSYAMSWVRQAPGKGLEWVSAISGSGGITYYAD
VH1016-045   EVQLLESGGGLVQPGGSLRLSCAASGFTFSSYAMSWVRQAPGKGLEWVSNISGSGGITYYAD
VH1016-039   EVQLLESGGGLVQPGGSLRLSCAASGFTFSSYAMSWVRQAPGKGLEWVSAISGSGGITYYAD
Consensus    EVQLLESGGGLVQPGGSLRLSCAASGFTFSSYAMSWVRQAPGKGLEWVSAISGSGGITYYAD
```

Figure 1 (continued)

```
IgHV3-23-1   SVKGRFTISRDNSKNTLYLQMNSLRAEDTAVYYCA-------------------
VH1016-040   SVKGRFTISRDNSKNTLYLQMNSLRAEDTAVYYCAKDRGWGSDYWGQGTLVTVSS
VH1016-045   SVKGRFTISRDNSKNTLYLQMNSLRAEDTAVYYCAKDRGWGSDYWGQGTLVTVSS
VH1016-039   SVKGRFTISRDNSKNTLYLQMNSLRAEDTAVYYCAKDRGWGSDYWGQGTLVTVSS
Consensus    SVKGRFTISRDNSKNTLYLQMNSLRAEDTAVYYCAKDRGWGSDYWGQGTLVTVSS VH Comparison 5:
IgHV4-30-2-1 QLQLQESGSGLVKPSQTLSLTCAVSGGSISSGGSSWSWIRQPPGKGLEWIGCIYHSGSTY
VH1016-068   QLQLQESGSGLVKPSQTLSLTCAVSGGSISSGGSSWSWIRQPPGKGLEWIGCIYHSGSTY
VH1016-078   QLQLQESGSGLVKPSQTLSLTCAVSGGSISSGGHSWSWIRQPPGKGLEWIGCIYHSGNTY
VH1016-084   QLQLQESGSGLVKPSQTLSLTCAVSGGSISSGGHSWSWIRQPPGKGLEWIGCIYHSGNTY
VH1016-061   QLQLQESGSGLVKPSQTLSLTCAVSGGSISSGGHSWSWIRQPPGKGLEWIGCIYHSGNTYD
VH1016-062   QLQLQESGSGLVKPSQTLSLTCAVSGGSISSGGHSWSWIRQPPGKGLEWIGCIYHSGNTYD
VH1016-063   QLQLQESGSGLVKPSQTLSLTCAVSGGSISSGGHSWSWIRQPPGKGLEWIGCIYHSGNTYD
VH1016-064   QLQLQESGSGLVKPSQTLSLTCAVSGGSISSGGHSWSWIRQPPGKGLEWIGCIYHSGNTYD
VH1016-087   QLQLQESGSGLVKPSQTLSLTCAVSGGSISSGGHSWSWIRQPPGKGLEWIGCIYHSGNTYD
Consensus    QLQLQESGSGLVKPSQTLSLTCAVSGGSISSGGHSWSWIRQPPGKGLEWIGCIYHSGNTYD IgHV4-30-2-1 NPSLKSRVTISVDRSKNQFSLKLSSVTAADTAVYYCAR-------------------
VH1016-068   NPSLKSRVTISVDRSKNQFSLKLSSVTAADTAVYYCARSSYDILTDWGQGTLVTVSS
VH1016-078   NPSLKSRVTISVDRSKNQFSLKLSSVTAADTAVYYCARSSYDILTDWGQGTLVTVSS
VH1016-084   NPSLKSRVTISVDRSKNQFSLKLSSVTAADTAVYYCARSSYDILTDWGQGTLVTVSS
VH1016-061   NPSLKSRVTISVDRSKNQFSLKLSSVTAADTAVYYCARSSYDILTDWGQGTLVTVSS
VH1016-062   NPSLKSRVTISVDRSKNQFSLKLSSVTAADTAVYYCARSSYDILTDWGQGTLVTVSS
VH1016-063   NPSLKSRVTISVDRSKNQFSLKLSSVTAADTAVYYCARSSYDILTDWGQGTLVTVSS
VH1016-064   NPSLKSRVTISVDRSKNQFSLKLSSVTAADTAVYYCARSSYDILTDWGQGTLVTVSS
VH1016-087   NPSLKSRVTISVDRSKNQFSLKLSSVTAADTAVYYCARSSYDILTDWGQGTLVTVSS
Consensus    NPSLKSRVTISVDRSKNQFSLKLSSVTAADTAVYYCARSSYDILTDWGQGTLVTVSS VH Comparison 6:
IgHV5-51-1   EVQLVQSGAEVKKPGESLKISCKGSGYSFTSYWIGWVRQMPGKGLEWMGIIYPGDSD
VH1016-016   EVQLVQSGAEVKKPGESLKISCKGSGYSFTSYWIGWVRQMPGKGLEWMGIIYPGDSD
VH1016-028   EVQLVQSGAEVKKPGESLKISCKGSGYSFTSYWIGWVRQMPGKGLEWMGIIYPGDSD
VH1016-008   EVQLVQSGAEVKKPGESLKISCKGSGYSFTSYWIGWVRQMPGKGLEWMGIIYPGDSD
VH1016-012   EVQLVQSGAEVKKPGESLKISCKGSGYSFTSYWIGWVRQMPGKGLEWMGIIYPGDSD
VH1016-035   EVQLVQSGAEVKKPGESLKISCKGSGYSFTSYWIGWVRQMPGKGLEWMGIIYPGDSD
VH1016-095   EVQLVQSGAEVKKPGESLKISCKGSGYSFTSYWIGWVRQMPGKGLEWMGIIYPGDSD
VH1016-093   EVQLVQSGAEVKKPGESLKISCKGSGYSFTSYWIGWVRQMPGKGLEWMGIIYPGDSD
VH1016-096   EVQLVQSGAEVKKPGESLKISCKGSGYSFTSYWIGWVRQMPGKGLEWMGIIYPGDSD
VH1016-104   EVQLVQSGAEVKKPGESLKISCKGSGYSFTSYWIGWVRQMPGKGLEWMGIIYPGDSD
Consensus    EVQLVQSGAEVKKPGESLKISCKGSGYSFTSYWIGWVRQMPGKGLEWMGIIYPGDSD IgHV5-51-1   TRYSPSFQGQVTISADKSISTAYLQWSSLKASDTAMYYCAR-------------------
VH1016-016   TRYSPSFQGQVTISADKSISTAYLQWSSLKASDTAMYYCARQEITGDFDYWGQGTLVTVSS
VH1016-028   TRYSPSFQGQVTISADKSISTAYLQWSSLKASDTAMYYCARQEITGDFDYWGQGTLVTVSS
VH1016-008   TRYSPSFQGQVTISADKSISTAYLQWSSLKASDTAMYYCARQEITGDFDYWGQGTLVTVSS
VH1016-012   TRYSPSFQGQVTISADKSISTAYLQWSSLKASDTAMYYCARQEITGDFDYWGQGTLVTVSS
VH1016-035   TRYSPSFQGQVTISADKSISTAYLQWSSLKASDTAMYYCARQEITGDFDYWGQGTLVTVSS
VH1016-095   TRYSPSFQGQVTISADKSISTAYLQWSSLKASDTAMYYCARQEITGDFDYWGQGTLVTVSS
VH1016-093   TRYSPSFQGQVTISADKSISTAYLQWSSLKASDTAMYYCARQEITGDFDYWGQGTLVTVSS
VH1016-096   TRYSPSFQGQVTISADKSISTAYLQWSSLKASDTAMYYCARQEITGDFDYWGQGTLVTVSS
VH1016-104   TRYSPSFQGQVTISADKSISTAYLQWSSLKASDTAMYYCARQEITGDFDYWGQGTLVTVSS
Consensus    TRYSPSFQGQVTISADKSISTAYLQWSSLKASDTAMYYCARQEITGDFDYWGQGTLVTVSS
```

Figure 2

```
IGKV1-12*01              DIQMTQSPSSVSASVGDRVTITCRASQGISNWLAWYQKP
VL1016-065  MDMMVPAQLLGLLLLWFPGSRCDIQMTQSPSSVSASVGDRVTITCRASQGISNWLAWYQHKP
VL1016-066  MDMMVPAQLLGLLLLWFPGSRCDIQMTQSPSSVSASVGDRVTITCRASQGISNWLAWYQHKP
VL1016-069  MDMMVPAQLLGLLLLWFPGSRCDIQMTQSPSSVSASVGDRVTITCRASQGISNWLAWYQHKP
VL1016-089  MDMMVPAQLLGLLLLWFPGSRCDIQMTQSPSSVSASVGDRVTITCRASQGISNWLAWYQHKP
VL1016-082  MDMMVPAQLLGLLLLWFPGSRCDIQMTQSPSSVSASVGDRVTITCRASQGISNWLAWYQHKP
VL1016-181  MDMMVPAQLLGLLLLWFPGSRCDIQMTQSPSSVSASVGDRVTITCRASQGISNWLAWYQHKP
Consensus   MDMMVPAQLLGLLLLWFPGSRCDIQMTQSPSSVSASVGDRVTITCRASQGISNWLAWYQHKP IGKV1-12*01 GKAPKLLIYAASSLSGVPSRFSGSGSGTDFTLTISSLQPEDFATYYCQQANSFPITFGQGTRLEIK
VL1016-065  GKAPKLLIYAASSLLSGVPSRFSGSGSGTDFTLTISSLQPEDFATYYCQQANSFPITFGQGTRLEIK
VL1016-066  GKAPKLLIYAASSLLSGVPSRFSGSGSGTDFTLTISSLQPEDFATYYCQQANSFPITFGQGTRLEIK
VL1016-069  GKAPKLLIYAASSLLSGVPSRFSGSGSGTDFTLTISSLQPEDFATYYCQQANSFPITFGQGTRLEIK
VL1016-089  GKAPKLLIYAASSLLSGVPSRFSGSGSGTDFTLTISSLQPEDFATYYCQQANSFPITFGQGTRLEIK
VL1016-082  GKAPKLLIYAASSLLSGVPSRFSGSGSGTDFTLTISSLQPEDFATYYCQQANSFPITFGQGTRLEIK
VL1016-181  GKAPKLLIYAASSLLSGVPSRFSGSGSGTDFTLTISSLQPEDFATYYCQQANSFPITFGQGTRLEIK
Consensus   GKAPKLLIYAASSLLSGVPSRFSGSGSGTDFTLTISSLQPEDFATYYCQQANSFPITFGQGTRLEIK IGKV1D-16*01             DIQMTQSPSSLSASVGDRVTITCRASQGISSWLAWYQQKPE
VL1016-005  MDMRVLAQLLGLLLLCFPGARCDIQMTQSPSSLSASVGDRVTITCRASQGISSWLAWYQQKPE
VL1016-031  MDMRVLAQLLGLLLLCFPGARCDIQMTQSPSSLSASVGDRVTITCRASQGISSWLAWYQQKPE
VL1016-006  MDMRVLAQLLGLLLLCFPGARCDIQMTQSPSSLSASVGDRVTITCRASQGISSWLAWYQQKPE
VL1016-007  MDMRVLAQLLGLLLLCFPGARCDIQMTQSPSSLSASVGDRVTITCRASQGISSWLAWYQQKPE
VL1016-011  MDMRVLAQLLGLLLLCFPGARCDIQMTQSPSSLSASVGDRVTITCRASQGISSWLAWYQQKPE
Consensus   MDMRVLAQLLGLLLLCFPGARCDIQMTQSPSSLSASVGDRVTITCRASQGISSWLAWYQQKPE IGKV1D-16*01KAPKSLIYAASSLQSGVPSRFSGSGSGTDFTLTISSLQPEDFATYYCQQYNSYPPTFGQGTKVEIK
VL1016-005  KAPKSLIYAASSLQSGVPSRFSGSGSGTDFTLTISSLQPEDFATYYCQQYNSYPPTFGQGTKVEIK
VL1016-031  KAPKSLIYAASSLQSGVPSRFSGSGSGTDFTLTISSLQPEDFATYYCQQYNSYPPTFGQGTKVEIK
VL1016-006  KAPKSLIYAASSLQSGVPSRFSGSGSGTDFTLTISSLQPEDFATYYCQQYNSYPPTFGQGTKVEIK
VL1016-007  KAPKSLIYAASSLQSGVPSRFSGSGSGTDFTLTISSLQPEDFATYYCQQYNSYPPTFGQGTKVEIK
VL1016-011  KAPKSLIYAASSLQSGVPSRFSGSGSGTDFTLTISSLQPEDFATYYCQQYNSYPPTFGQGTKVEIK
Consensus   KAPKSLIYAASSLQSGVPSRFSGSGSGTDFTLTISSLQPEDFATYYCQQYNSYPPTFGQGTKVEIK IGKV1-12*01              DIQMTQSPSSVSASVGDRVTITCRASQGISSWLAWYQQKPG
VL1016-017  MDMMVPAQLLGLLLLWFPGSRCDIQMTQSPSSVSASVGDRVTITCRASQGISSWLAWYQHKPG
VL1016-022  MDMMVPAQLLGLLLLWFPGSRCDIQMTQSPSSVSASVGDRVTITCRASQGISSWLAWYQHKPG
VL1016-025  MDMMVPAQLLGLLLLWFPGSRCDIQMTQSPSSVSASVGDRVTITCRASQGISSWLAWYQHKPG
Consensus   MDMMVPAQLLGLLLLWFPGSRCDIQMTQSPSSVSASVGDRVTITCRASQGISSWLAWYQHKPG IGKV1-12*01 KAPKLLIYAASSLQSGVPSRFSGSGSGTDFTLTISSLQPEDFATYYCQQANSFPWTFGQGTKVEIK
VL1016-017  KAPKLLIYAASSLQSGVPSRFSGSGSGTDFTLTISSLQPEDFATYYCQEANSFTWTFGQGTKVEIK
VL1016-022  KAPKLLIYAASSLQSGVPSRFSGSGSGTDFTLTISSLQPEDFATYYCQEANSFTWTFGQGTKVEIK
VL1016-025  KAPKLLIYAASSLQSGVPSRFSGSGSGTDFTLTISSLQPEDFATYYCQEANSFTWTFGQGTKVEIK
Consensus   KAPKLLIYAASSLQSGVPSRFSGSGSGTDFTLTISSLQPEDFATYYCQEANSFTWTFGQGTKVEIK IGKV3-11*01              EIVLTQSPATLSLSPGERATLSCRASQSVSSYLAWYQQKPGQ
VL1016-039  MEAPAQLLFLLLLWLPDTTGEIVLTQSPATLSLSPGERATLSCRASQSVSSYLAWYQQKPGQ
VL1016-040  MEAPAQLLFLLLLWLPDTTGEIVLTQSPATLSLSPGERATLSCRASQSVSSYLAWYQQKPGQ
VL1016-045  MEAPAQLLFLLLLWLPDTTGEIVLTQSPATLSLSPGERATLSCRASQSVSSYLAWYQQKPGQ
Consensus   MEAPAQLLFLLLLWLPDTTGEIVLTQSPATLSLSPGERATLSCRASQSVSSYLAWYQQKPGQ IGKV3-11*01 APRLLIYDASNRATGIPARFSGSGSGTDFTLTISSLEPEDFAVYYCQQRSNWPFTFGPGTKVDIK
VL1016-039  APRLLIYDASNRATGIPARFSGSGSGTDFTLTISSLEPEDFAVYYCQQRSNWPFTFGPGTKVDIK
VL1016-040  APRLLIYDASNRATGIPARFSGSGSGTDFTLTISSLEPEDFAVYYCQQRSNWPFTFGPGTKVDIK
VL1016-045  APRLLIYDASNRATGIPARFSGSGSGTDFTLTISSLEPEDFAVYYCQQRSNWPFTFGPGTKVDIK
Consensus   APRLLIYDASNRATGIPARFSGSGSGTDFTLTISSLEPEDFAVYYCQQRSNWPFTFGPGTKVDIK
```

Figure 2 (continued)

```
IGKV1-12*01              DIQMTQSPSSVSASVGDRVTIITCRASQGISSWLAWYQ KPG
VL1016-061   MDMMVPAQLLGLLLLWFPGSRCDIQMTQSPSSVSASVGDRVTIITCRASQGISSWLAWYQ KPG
VL1016-062   MDMMVPAQLLGLLLLWFPGSRCDIQMTQSPSSVSASVGDRVTIITCRASQGISSWLAWYQ KPG
VL1016-063   MDMMVPAQLLGLLLLWFPGSRCDIQMTQSPSSVSASVGDRVTIITCRASQGISSWLAWYQ KPG
VL1016-064   MDMMVPAQLLGLLLLWFPGSRCDIQMTQSPSSVSASVGDRVTIITCRASQGISSWLAWYQ KPG
VL1016-068   MDMMVPAQLLGLLLLWFPGSRCDIQMTQSPSSVSASVGDRVTIITCRASQGISSWLAWYQ KPG
VL1016-084   MDMMVPAQLLGLLLLWFPGSRCDIQMTQSPSSVSASVGDRVTIITCRASQGISSWLAWYQ KPG
Consensus    MDMMVPAQLLGLLLLWFPGSRCDIQMTQSPSSVSASVGDRVTIITCRASQGISSWLAWYQHKPG IGKV1-12*01  KAPKLLIYAASSLQSGVPSRFSGSGSGTDFTLTISSLQPEDFATYYCQQAN FPITFGQGTRLEIK
VL1016-061   KAPKLLIYAASSLQSGVPSRFSGSGSGTDFTLTISSLQPEDFATYYCQQAN FPITFGQGTRLEIK
VL1016-062   KAPKLLIYAASSLQSGVPSRFSGSGSGTDFTLTISSLQPEDFATYYCQQAN FPITFGQGTRLEIK
VL1016-063   KAPKLLIYAASSLQSGVPSRFSGSGSGTDFTLTISSLQPEDFATYYCQQAN FPITFGQGTRLEIK
VL1016-064   KAPKLLIYAASSLQSGVPSRFSGSGSGTDFTLTISSLQPEDFATYYCQQAN FPITFGQGTRLEIK
VL1016-068   KAPKLLIYAASSLQSGVPSRFSGSGSGTDFTLTISSLQPEDFATYYCQQAN FPITFGQGTRLEIK
VL1016-084   KAPKLLIYAASSLQSGVPSRFSGSGSGTDFTLTISSLQPEDFATYYCQQAN FPITFGQGTRLEIK
Consensus    KAPKLLIYAASSLQSGVPSRFSGSGSGTDFTLTISSLQPEDFATYYCQQANGFPITFGQGTRLEIK IGKV1-13*02              AIQLTQSPSSLSASVGDRVTITCRASQGISSALAWYQQKPG
VL1016-008   MDMRVPAQLLGLLLLWLPGARCAIQLTQSPSSLSASVGDRVTITCRASQGISSALAWYQQKPG
VL1016-012   MDMRVPAQLLGLLLLWLPGARCAIQLTQSPSSLSASVGDRVTITCRASQGISSALAWYQQKPG
VL1016-035   MDMRVPAQLLGLLLLWLPGARCAIQLTQSPSSLSASVGDRVTITCRASQGISSALAWYQQKPG
VL1016-104   MDMRVPAQLLGLLLLWLPGARCAIQLTQSPSSLSASVGDRVTITCRASQGISSALAWYQQKPG
VL1016-093   MDMRVPAQLLGLLLLWLPGARCAIQLTQSPSSLSASVGDRVTITCRASQGISSALAWYQQKPG
VL1016-096   MDMRVPAQLLGLLLLWLPGARCAIQLTQSPSSLSASVGDRVTITCRASQGISSALAWYQQKPG
VL1016-016   MDMRVPAQLLGLLLLWLPGARCAIQLTQSPSSLSASVGDRVTITCRASQGISSALAWYQQKPG
VL1016-028   MDMRVPAQLLGLLLLWLPGARCAIQLTQSPSSLSASVGDRVTITCRASQGISSALAWYQQKPG
VL1016-095   MDMRVPAQLLGLLLLWLPGARCAIQLTQSPSSLSASVGDRVTITCRASQGISSALAWYQQKPG
Consensus    MDMRVPAQLLGLLLLWLPGARCAIQLTQSPSSLSASVGDRVTITCRASQGISSALAWYQQKPG IGKV1-13*02  KAPKLLIYDASSLESGVPSRFSGSGSGTDFTLTISSLQPEDFATYYCQQFNSYP  TFGQGTKVEIK
VL1016-008   KAPKLLIYDASSLESGVPSRFSGSGSGTDFTLTISSLQPEDFATYYCQQFNSYP  TFGQGTKVEIK
VL1016-012   KAPKLLIYDASSLESGVPSRFSGSGSGTDFTLTISSLQPEDFATYYCQQFNSYP  TFGQGTKVEIK
VL1016-035   KAPKLLIYDASSLESGVPSRFSGSGSGTDFTLTISSLQPEDFATYYCQQFNSYP  TFGQGT  EIK
VL1016-104   KAPKLLIY ASSLESGVPSRFSGSGSGTDFTLTI SLQPEDFATYYCQQFNSYP  TFGQGT  EIK
VL1016-093   KAP LLIY ASSLESGVPSRFSGSGSGTDFTLTI SLQPEDFATYYCQQFNSYPL TFGGGTKVEIK
VL1016-096   KAP LLIY ASSLESGVPSRFSGSGSGTDFTLTI SLQPEDFATYYCQQFNSYPL TFGGGTKVEIK
VL1016-016   KAP LLIY ASSLESGVPSRFSGSGSGTDFTLTI SLQPEDFATYYCQQFNSYPL TFGGGTKVEIK
VL1016-028   KAP LLIY ASSLESGVPSRFSGSGSGTDFTLTI SLQPEDFATYYCQQFNSYPL TFGGGTKVEIK
VL1016-095   KAP LLIY ASSLESGVPSRFSGSGSGTDFTLTI SLQPEDFATYYCQQFNSYPL TFGGGTKVEIK
Consensus    KAPKLLIYDASSLESGVPSRFSGSGSGTDFTLTISSLQPEDFATYYCQQFNSYPL TFGGGTKVEIK
```

Figure 5
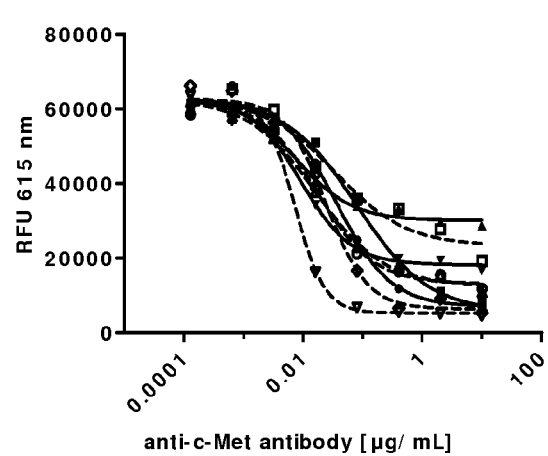
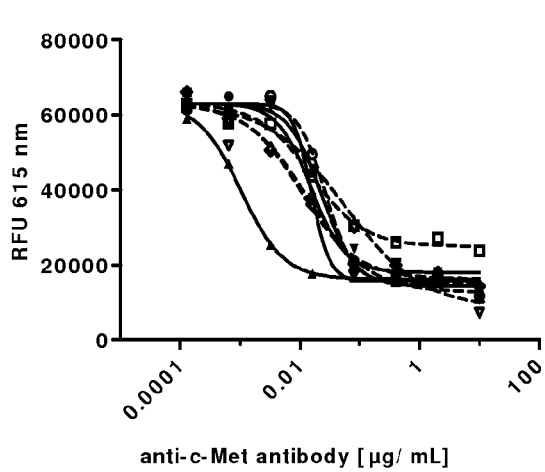

Figure 6
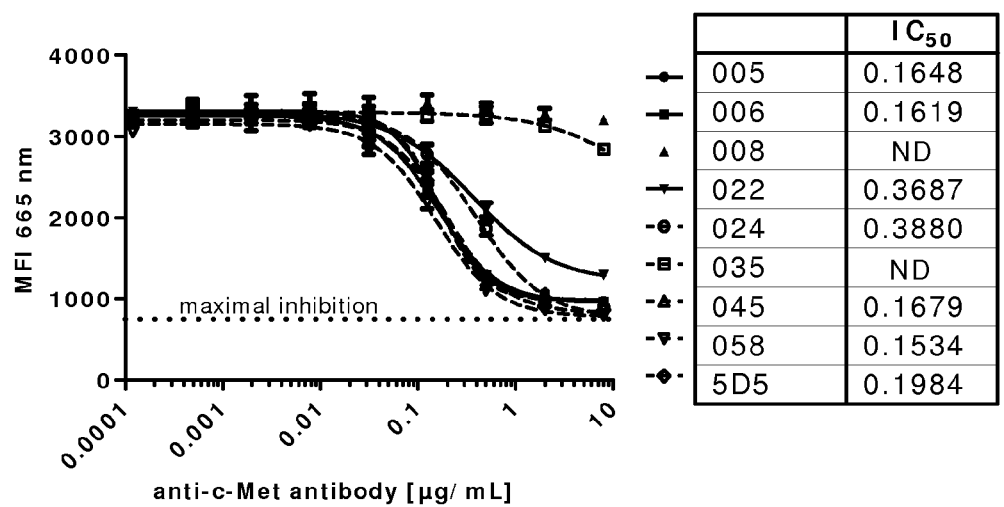
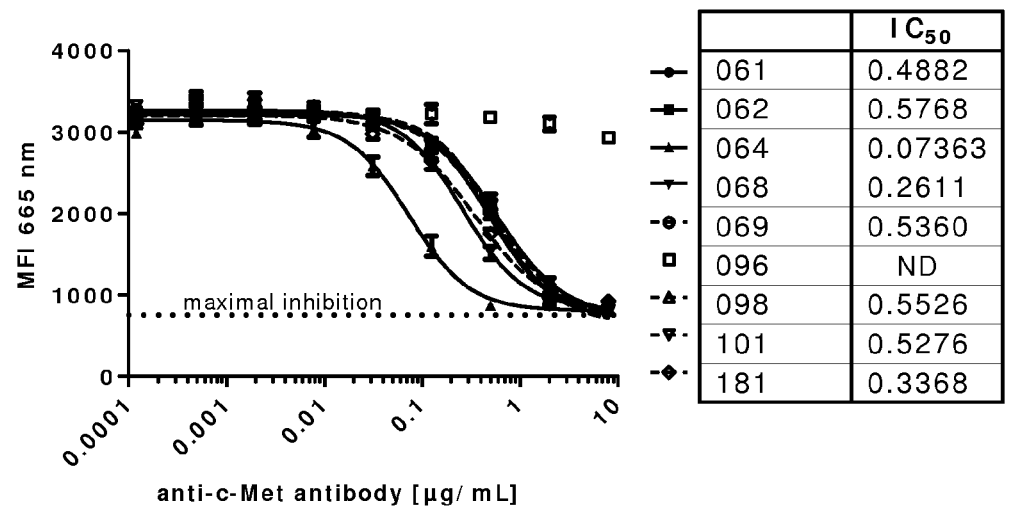

Figure 14
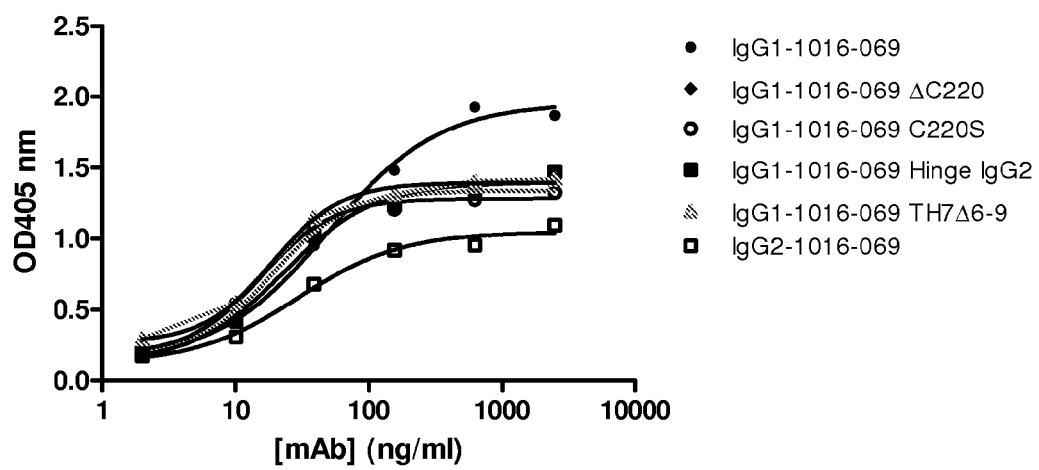
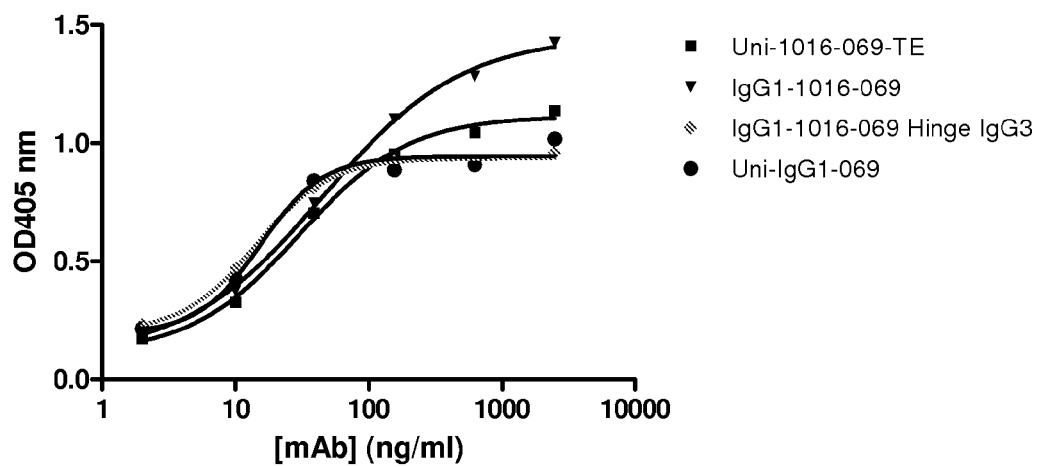

MONOCLONAL ANTIBODIES AGAINST C-MET

RELATED APPLICATIONS

This application is a 35 U.S.C. 371 national stage filing of International Application No. PCT/EP2011/053646 filed Mar. 10, 2011, which claims priority to Denmark Patent Application No. PA 2010 00862 filed on Sep. 24, 2010, to Denmark Patent Application No. PA 2010 00191 filed on Mar. 10, 2010, and US Provisional Application No. 61/312, 622 filed on Mar. 10, 2010. The contents of the aforementioned applications are hereby incorporated by reference.

FIELD OF THE INVENTION

The present invention relates to monoclonal antibodies directed to human c-Met, the hepatocyte growth factor receptor, and to uses of such antibodies, in particular their use in the treatment of cancer.

BACKGROUND OF THE INVENTION c-Met is a membrane-spanning receptor tyrosine kinase protein. The primarily single chain precursor is post-translationally cleaved to produce the mature form of the c-Met heterodimer that consists of an extracellular α-chain (50 kDa) and a longer transmembrane β-chain (145 kDa), which are disulfide-linked (Birchmeier et al. 2003. Nat Rev Mol Cell Biol 4:915). The extracellular part of c-Met is composed of three domain types. The N-terminal SEMA domain is formed by the whole α-subunit and part of the β-subunit, and encompasses homology to semaphorin proteins. The SEMA domain is followed by a cysteine-rich domain and further by four immunoglobulin-(Ig)-like domains. The cytoplasmic part contains a juxtamembrane kinase domain and a carboxy-terminal tail that is essential for downstream signaling. The only known high affinity ligand for c-Met, hepatocyte growth factor (HGF), is mainly expressed by fibroblasts under normal conditions (Li and Tseng 1995. J Cell Physiol 163:61) and by tumor cells (Ferracini et al. 1995. Oncogene 10:739). HGF (also called scatter factor: SF) is synthesized as a precursor that is converted proteolytically into an active α/β heterodimer. Based on the crystal structure of the receptor-binding fragment, HGF is thought to bind c-Met as a dimer (Chirgadze et al. 1999. Nat Struct Biol 6:72). The HGF-α chain binds with high affinity to the Ig-like domain in c-Met, whereas the HGF-β chain binds with low affinity to the c-Met SEMA domain (Basilico et al. 2008. J Biol Chem 283:21267). The latter interaction is responsible for c-Met dimerization and receptor tyrosine kinase activation upon binding of the active HGF heterodimer. Receptor autophosphorylation results in a unique docking site for recruitment of effectors, of which Gab1 (growth factor receptor-bound protein 2 [Grb2]-associated binder 1) binding is essential for the major c-Met downstream signaling pathways (Comoglio et al. 2008. Nat Rev Drug Discov 7:504):

Ras-ERK1/2 pathway: proliferation.
Ras-Rac pathway: invasion, motility, epithelial-to-mesenchymal transition.
PI3K-Akt pathway: survival.

c-Met is expressed on the surface of epithelial and endothelial cells of many organs during embryogenesis and in adulthood, including the liver, pancreas, prostate, kidney, muscle, and bone marrow. c-Met activation plays an essential role in the so-called "invasive growth" programme that consists of a series of processes, including proliferation, motility, angiogenesis and protection from apoptosis (Boccaccio and Comoglio 2006. Nat Rev Cancer 6:637). These c-Met-regulated processes occur under normal physiological conditions during embryonic development, hepatic and cardiac injury repair, and pathologically during oncogenesis (Eder et al. 2009. Clin Cancer Res 15:2207).

Inappropriate c-Met signaling occurs in virtually all types of solid tumors, such as bladder, breast, cervical, colorectal, gastric, head and neck, liver, lung, ovarian, pancreatic, prostate, renal, and thyroid cancers, as well as in various sarcomas, hematopoietic malignancies, and melanoma (Birchmeier et al. 2003. Nat Rev Mol Cell Biol 4:915; Comoglio et al. 2008. Nat Rev Drug Discov 7:504; Peruzzi and Bottaro 2006. Clin Cancer Res 12:3657). The underlying mechanisms for tumorigenicity of c-Met are typically achieved in three different ways:

autocrine HGF/c-Met loops,
c-Met or HGF overexpression,
kinase-activating mutations in the c-Met receptor coding sequence.

Most notably, activating c-Met mutations have been identified in patients with hereditary papillary renal cancer (Schmidt et al. 1997. Nat Genet 16:68). Constitutive activation of c-Met contributes to one or a combination of proliferative, invasive, survival, or angiogenic cancer phenotypes. Gene silencing of endogenously expressed c-Met in tumor cells has been shown to result in lack of proliferation and tumor growth and regression of established metastasis, as well as decreased generation of new metastases (Corso et al. 2008. Oncogene 27:684).

As c-Met contributes to multiple stages of cancer development, from initiation through progression to metastasis, c-Met and its ligand HGF have become leading candidates for targeted cancer therapies (Comoglio et al. 2008. Nat Rev Drug Discov 7:504; Knudsen and Vande Woude 2008. Curr Opin Genet Dev 18:87). Several strategies are being explored to reach this goal:

Decoy receptors: subregions of HGF or c-Met or molecular analogs can act antagonistic as stoichiometric competitors by blocking ligand binding or receptor dimerization. One example of such an antagonistic subregion of HGF is NK4 (Kringle Pharma).

Small molecule tyrosine kinase inhibitors (TKIs): Three c-Met-specific TKIs in different stages of clinical evaluation are ARQ197 (ArQule), JNJ 38877605 (Johnson & Johnson) and PF-04217903 (Pfizer).

Anti-HGF monoclonal antibodies, such as AMG102, rilotumumab (Amgen), HuL2G7 (Takeda), and AV-299 (Schering).

Anti-c-Met monoclonal antibodies have been described in WO2005016382, WO2006015371, WO2007090807, WO2007126799 WO2009007427, WO2009142738 and van der Horst et al. (van der Horst et al. 2009. Neoplasoa 11:355). MetMAb (Genentech) is a humanized monovalent (one-armed) OA-5D5 antibody that binds to the extracellular domain of c-Met, thereby preventing HGF binding and subsequent receptor activation (Jin et al. 2008. Cancer Res 68:4360). In mouse xenograft models, treatment with MetMAb was found to inhibit tumor growth of HGF-driven orthotopic glioblastoma and subcutaneous pancreatic tumors (Jin et al. 2008. Cancer Res 68:4360; Martens et al. 2006. Clin Cancer Res 12:6144). h224G11 (Pierre Fabre) (Corvaia and Boute 2009. Abstract 835 AACR 100th Annual Meeting) is a humanized bivalent anti-c-Met IgG1 antibody. Anti-tumor effects of this antibody have been observed in mice (Goetsch et al. 2009. Abstract 2792 AACR 100th Annual Meeting). CE-355621 (Pfizer) is a human IgG2 that blocks ligand binding by binding to the extracellular domain of c-Met and inhibits HGF-dependent growth in tumor xenograft models (Tseng et al. 2008.3 Nucl Med 49:129).

In conclusion, several anti-c-Met products are being investigated, but so far no anti-c-Met product has yet been approved for therapeutic use. There remains a need for effective and safe products for treating serious c-Met-related diseases, such as cancer.

SUMMARY OF THE INVENTION

It is an object of the present invention to provide novel highly specific and effective monoclonal anti-c-Met antibodies for medical use. The antibodies of the invention exhibit c-Met binding characteristics that differ from the antibodies described in the art. In preferred embodiments, the antibodies of the invention have a high affinity towards human c-Met, are antagonistic and have a favorable pharmacokinetic profile for use in human patients.

BRIEF DESCRIPTION OF THE DRAWINGS

FIG. 1: Alignment of HuMabs heavy chain variable region sequences. On the basis of these sequences, consensus sequence can be defined for some of the CDR sequences. These consensus sequences are given in Table 4.

VH Comparison 1: IgHV1-18-1 (SEQ ID NO: 221), VH1016-181(SEQ ID NO: 129), VH1016-066, (SEQ ID NO: 136), VH1016-065, (SEQ ID NO: 139), VH1016-069, (SEQ ID NO: 97), VH1016-082, (SEQ ID NO: 141), VH1016-089, (SEQ ID NO: 143), Consensus (SEQ ID NO: 222).

VH Comparison 2: IgHV1-69-4, (SEQ ID NO: 223), VH1016-005, (SEQ ID NO: 1), VH1016-031, (SEQ ID NO: 145), VH1016-006, SEQ ID NO: 9), VH1016-007, SEQ ID NO: 147), VH1016-011, SEQ ID NO: 149), Consensus (SEQ ID NO: 224).

VH Comparison 3: IgHV3-30-3-1, (SEQ ID NO: 225), VH1016-017, (SEQ ID NO: 151), VH1016-025, (SEQ ID NO: 153), VH1016-022, SEQ ID NO: 25), Consensus (SEQ ID NO: 25).

VH Comparison 4: IgHV3-23-1, (SEQ ID NO: 226), VH1016-040, (SEQ ID NO: 155), VH1016-045, (SEQ ID NO: 49), VH1016-039, (SEQ ID NO: 157), Consensus (SEQ ID NO: 227).

VH Comparison 5: IgHV4-30-2-1, (SEQ ID NO: 228), VH1016-068 ID NO: 89), VH1016-078,(SEQ ID NO: 159) VH1016-084(SEQ ID NO: 161), VH1016-061, (SEQ ID NO: 65), VH1016-062, (SEQ ID NO: 73), VH1016-063, (SEQ ID NO: 163), VH1016-064, (SEQ ID NO: 81), VH1016-087, (SEQ ID NO: 165), Consensus (SEQ ID NO: 165).

VH Comparison 6: IgHV5-51-1, (SEQ ID NO: 229), VH1016-016, (SEQ ID NO: 167), VH1016-028, (SEQ ID NO: 169), VH1016-008, (SEQ ID NO: 17), VH1016-012, (SEQ ID NO: 171), VH1016-035, (SEQ ID NO: 41), VH1016-095, (SEQ ID NO: 173), VH1016-093, (SEQ ID NO: 175), VH1016-096, (SEQ ID NO: 105), VH016-104, (SEQ ID NO: 177), Consensus (SEQ ID NO: 105).

FIG. 2: Alignment of HuMabs light chain variable region sequences. On the basis of these sequences, consensus sequence can be defined for some of the CDR sequences. These consensus sequences are given in Table 4.

IGKV1-12*01, (SEQ ID NO: 230), VL1016-065, (SEQ ID NO: 140), VL1016-066, (SEQ ID NO: 138), VL1016-069, (SEQ ID NO: 101), VL1016-089, (SEQ ID NO: 144), VL1016-082(SEQ ID NO: 142), VL1016-181, (SEQ ID NO: 133), Consensus (SEQ ID NO: 133).

IGKV1D-16*01, (SEQ ID NO: 231), VL1016-005, (SEQ ID NO: 5), VL1016-031, (SEQ ID NO: 146), VL1016-006, (SEQ ID NO: 13), VL1016-007, (SEQ ID NO: 148), VL1016-011(SEQ ID NO: 150), Consensus (SEQ ID NO: 150).

IGKV1-12*01, (SEQ ID NO: 230), VL1016-017 (SEQ ID NO: 152), VL1016-022, (SEQ ID NO: 29), VL1016-025, (SEQ ID NO: 154), Consensus (SEQ ID NO: 152).

IGKV3-11*01, (SEQ ID NO: 232), VL1016-039, (SEQ ID NO: 158), VL1016-040, (SEQ ID NO: 156), VL1016-045, (SEQ ID NO: 53), Consensus (SEQ ID NO: 53).

IGKV1-2*01, (SEQ ID NO: 230), VL016-061, (SEQ ID NO: 69), VL1016-062, (SEQ ID NO: 77), VL1016-063, (SEQ ID NO: 164), VL1016-064, (SEQ ID NO: 85), VL1016-068(SEQ ID NO: 93), VL1016-084, (SEQ ID NO: 162), Consensus (SEQ ID NO: 85).

IGKV1-13*02, (SEQ ID NO: 233), VL1016-008, (SEQ ID NO: 21), VL1016-012, (SEQ ID NO: 172), VL1016-035, (SEQ ID NO: 45), VL1016-104, (SEQ ID NO: 178), VL1016-093 (SEQ ID NO: 176), VL1016-096, (SEQ ID NO: 109), VL1016-016, (SEQ ID NO: 168), VL1016-028, (SEQ ID NO: 170), VL1016-095, (SEQ ID NO: 174), Consensus (SEQ ID NO: 174).

Figure 3:
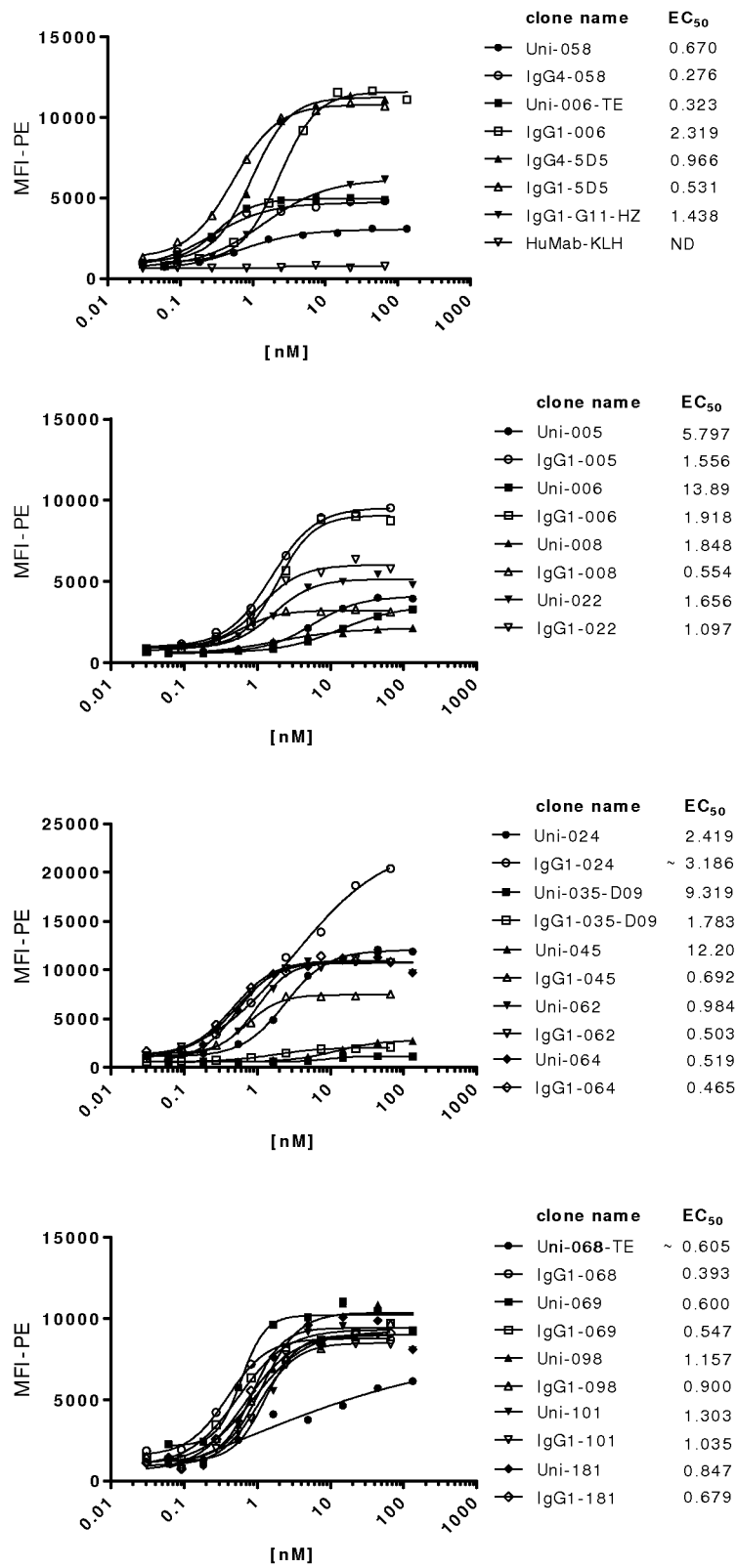

FIG. 3: Binding curves of monovalent and bivalent forms of anti-c-Met antibodies to c-Met expressing A431 cells. Data shown are MFI of one representative experiment. Because IgG1-024 and Uni-068 did not show saturated binding to A431 cells it was not possible to calculate an accurate $EC_{50}$ value.

Figure 4:
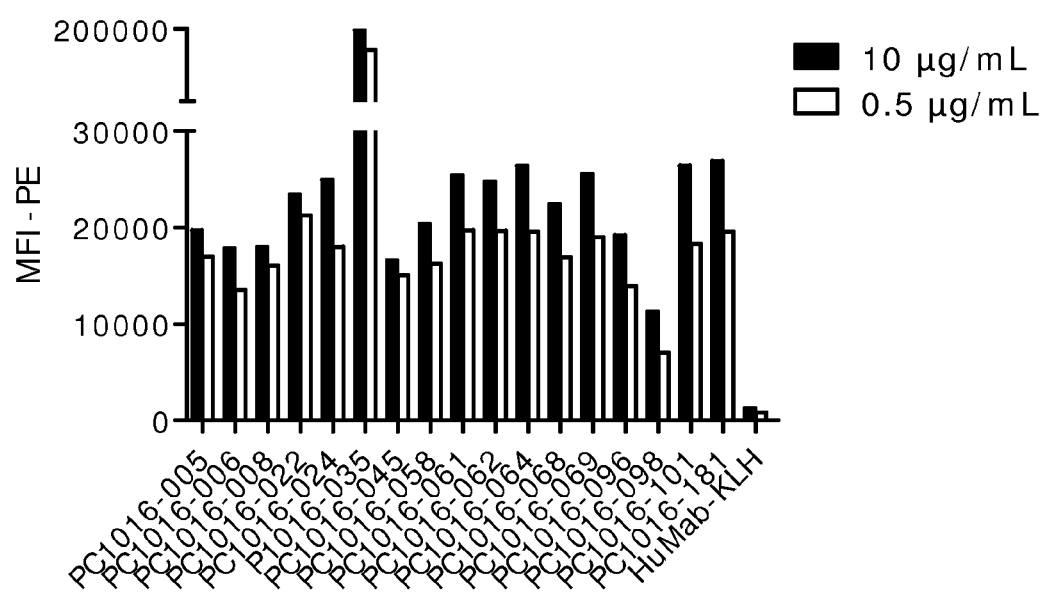

FIG. 4: Binding of antibodies to c-Met expressed on Rhesus monkey epithelial cells. Data shown are MFI of one experiment.

FIG. 5: Anti-c-Met antibody-induced inhibition of HGF binding to the extracellular domain of the c-Met receptor. Data shown is one representative experiment.

FIG. 6: HGF binding inhibition curves of the various anti-c-Met antibodies for binding to cMetSEMA_567His8 tested with TR-FRET. Data shown are mean MFI±standard deviation of three independent experiments.

Figure 7:
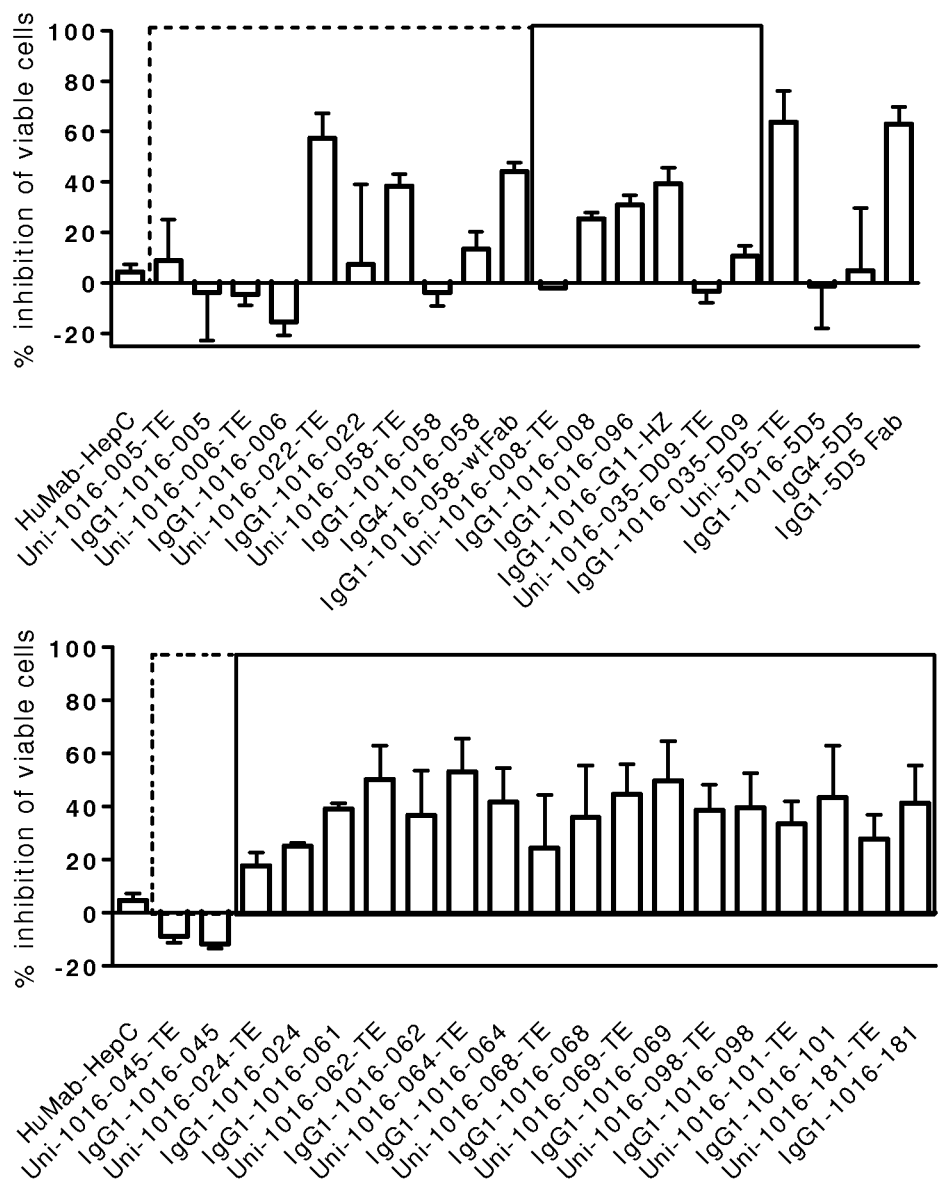

FIG. 7: Percentage inhibition of viable KP4 cells after anti-c-Met antibody treatment compared to untreated cells (0%). Data shown are percentages inhibition of viable cells of two independent experiments±the standard deviation. IgG1-1016-022 was only positive in one experiment.

Figure 8:
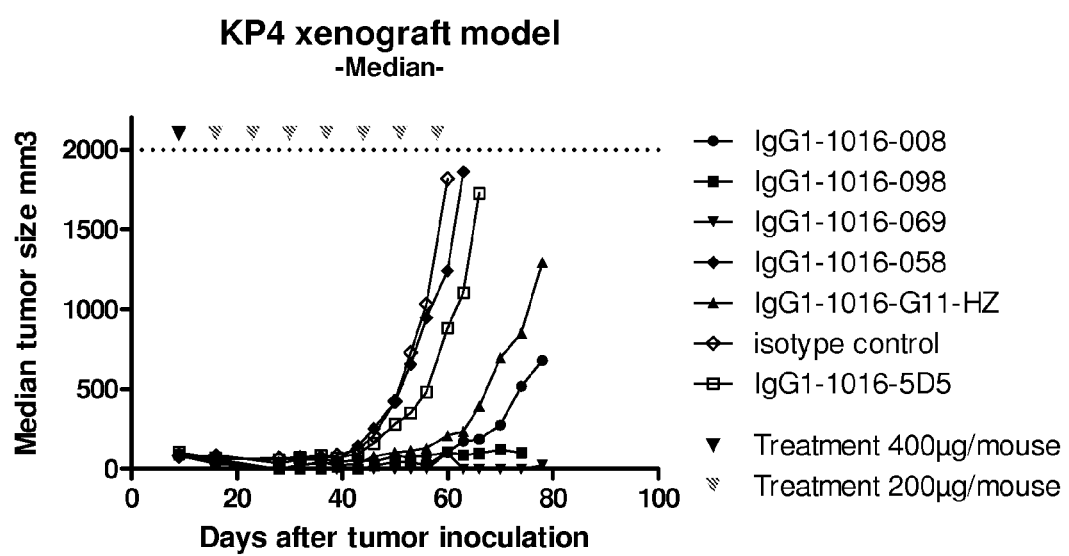

FIG. 8: Efficacy of anti-c-Met antibodies to inhibit tumor growth in a KP4 xenograft model in SCID mice. Mice were treated with 400 µg antibody at day 9 followed weekly with a maintenance dose of 200 µg. Median tumor sizes per treatment group are shown.

Figure 9:
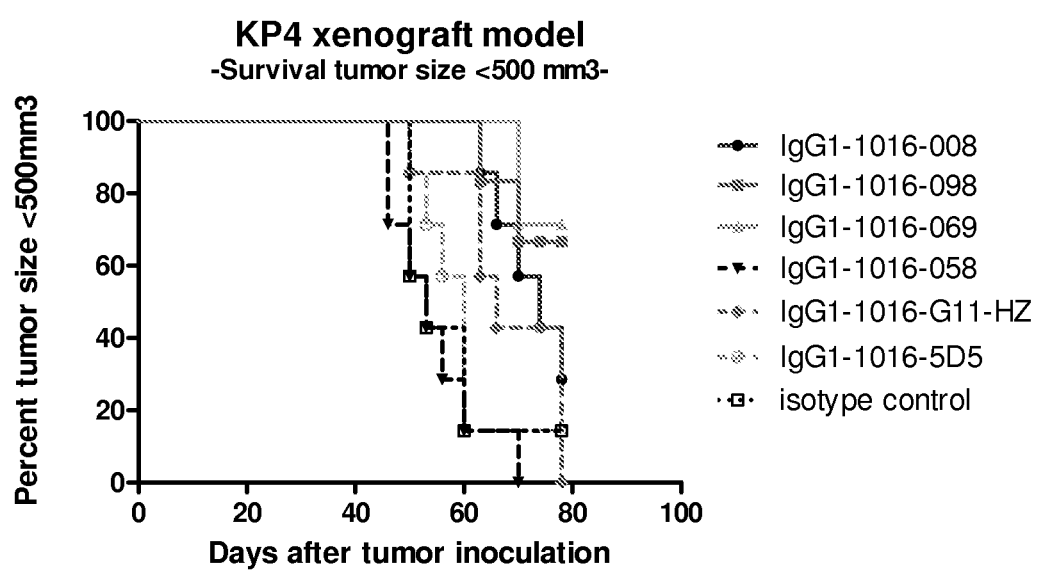

FIG. 9: Efficacy of anti-c-Met antibodies to inhibit tumor growth in a KP4 xenograft model in SCID mice. Mice were treated with 400 µg antibody at day 9 followed weekly with a maintenance dose of 200 µg. Effect of treatment on tumor incidence in time. Shown is the percentage tumor free mice (tumor sizes <500 mm$^3$). Tumor formation is delayed in mice treated with antagonistic antibodies compared to control antibodies.

Figure 10:
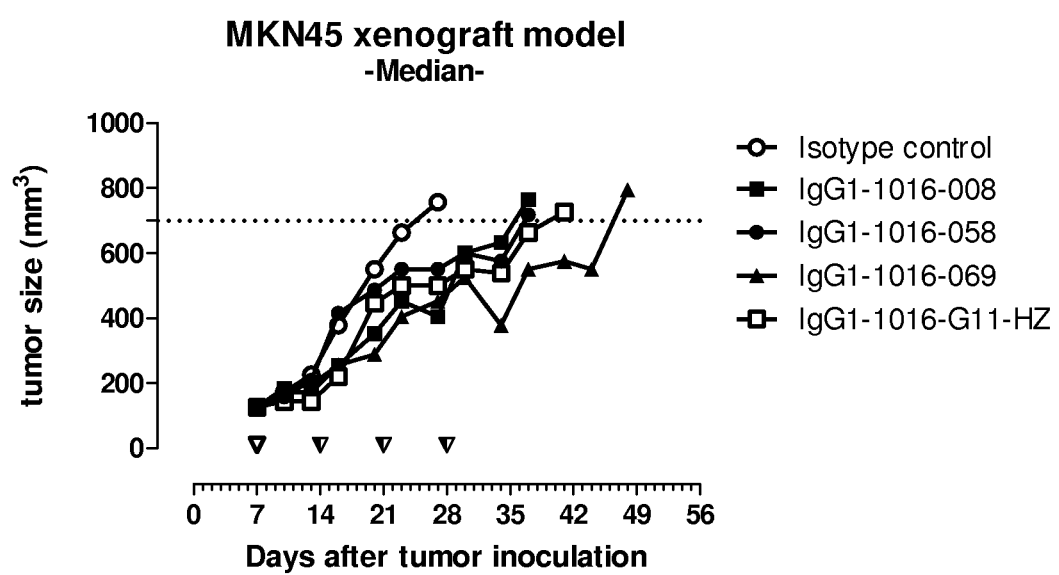

FIG. 10: Efficacy of anti-c-Met antibodies to inhibit tumor growth in an MKN45 xenograft model in SCID mice. Mice were treated with 40 mg/kg antibody on day 7 and 20 mg/kg antibody on days 14, 21 and 28. Median tumor sizes until 50% of the mice reached the 700 mm$^3$ endpoint, per treatment group are shown.

Figure 11:
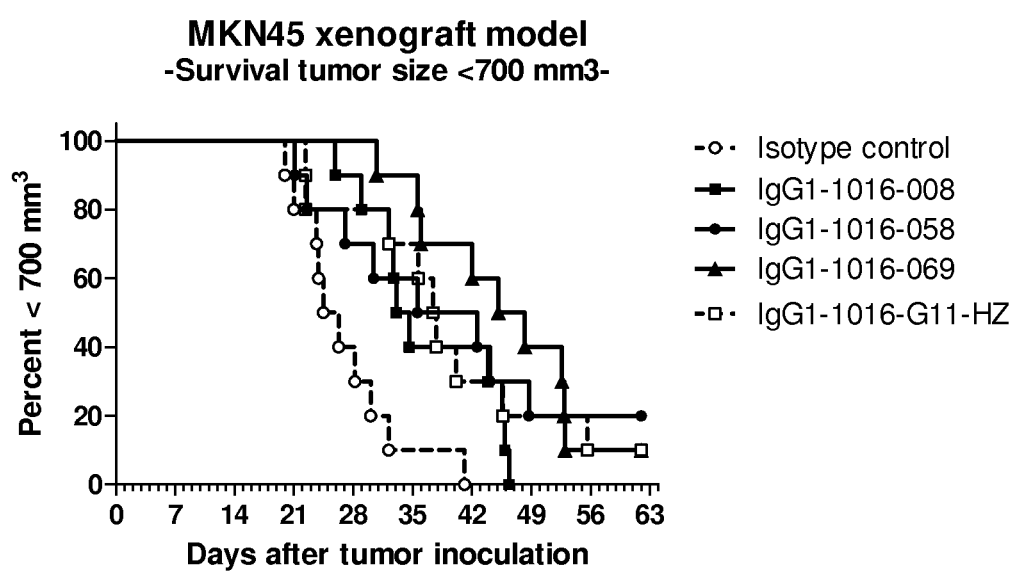

FIG. 11: Efficacy of anti-c-Met antibodies to inhibit tumor growth in an MKN45 xenograft model in SCID mice. Mice were treated with 40 mg/kg antibody on day 7 and 20 mg/kg antibody on days 14, 21 and 28. The percentage mice with tumor sizes smaller then 700 mm³ is shown in a Kaplan Meier plot. Tumor formation is delayed in mice treated with anti-c-Met antibodies compared to isotype control antibody.

Figure 12:
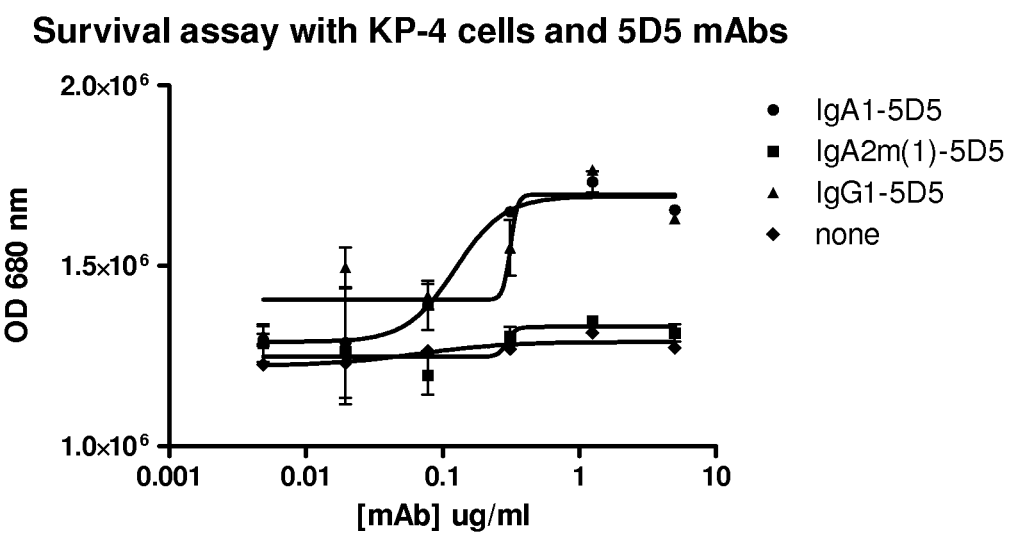

FIG. 12: KP4 viability assay to determine the effect of antibody flexibility on agonistic activity. The IgA2m(1) format did not induce proliferation, in contrast to IgA1 and IgG1 formats of the same antibody. Variants of the 5D5 anti-c-Met antibody (see U.S. Pat. No. 6,468,529 and Example 2) were used in this experiment.

Figure 13:
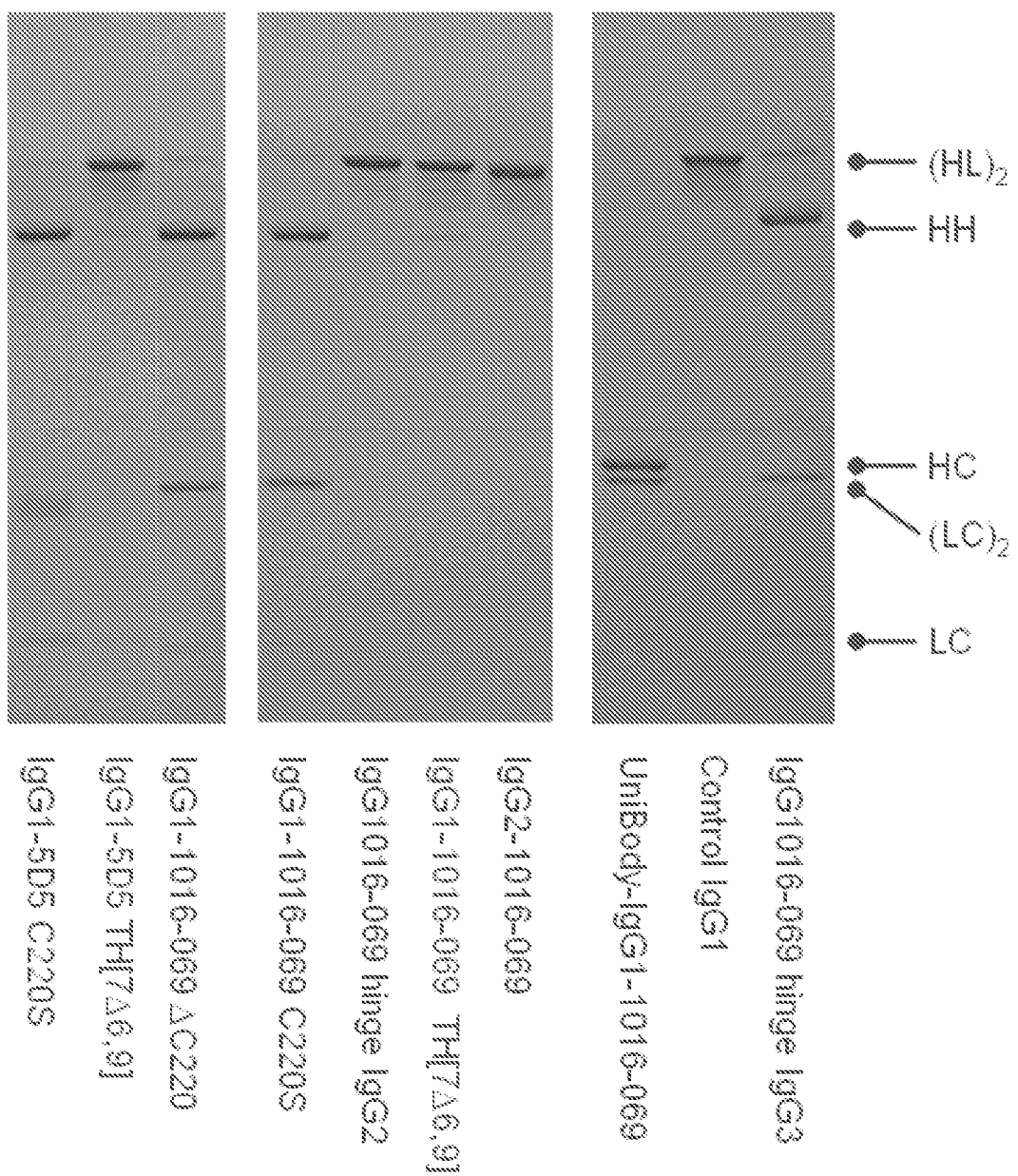

FIG. 13: Non-reduced SDS-PAGE analysis of the flexibility mutants of (069). No aberrant multimers or degradation products were observed whereas the light chain paring was visible as a 50 kD band ((LC)$_2$) in the C220S, ΔC220 and IgG1-hinge IgG3 mutants.

FIG. 14: Antigen binding ELISA to measure c-Met binding of hinge mutants of c-Met antibodies. All mutants bind with comparable affinity to c-Met as shown in ELISA.

Figure 15:
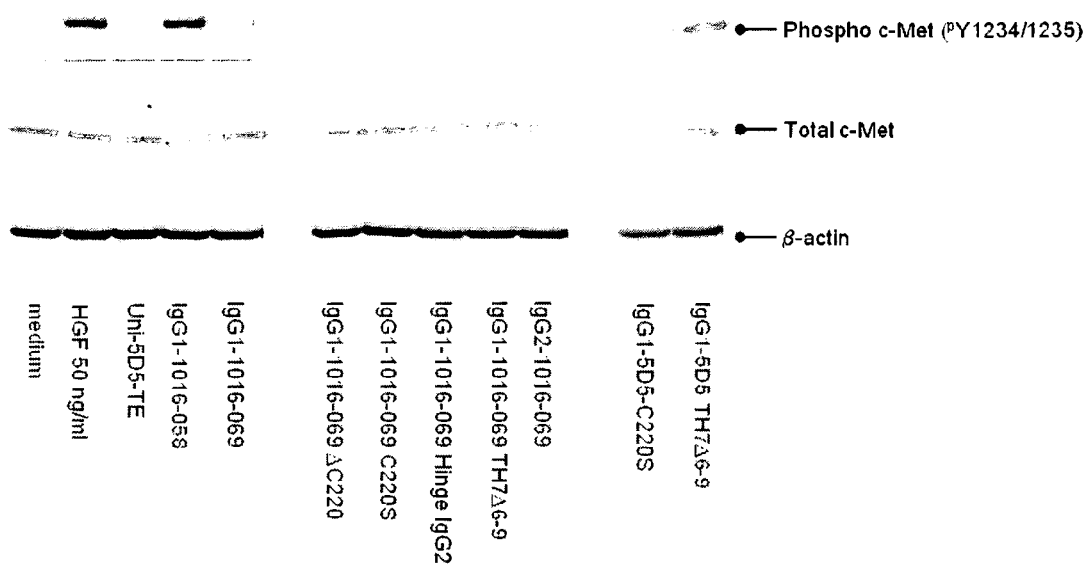

FIG. 15: c-Met phosphorylation as readout for agonistic activity of antibodies against c-Met. FIG. 15 shows Western blot results of A549 lysates; membranes stained with antibodies against phosphorylated c-met, total c-Met or β-actin.

Figure 16:
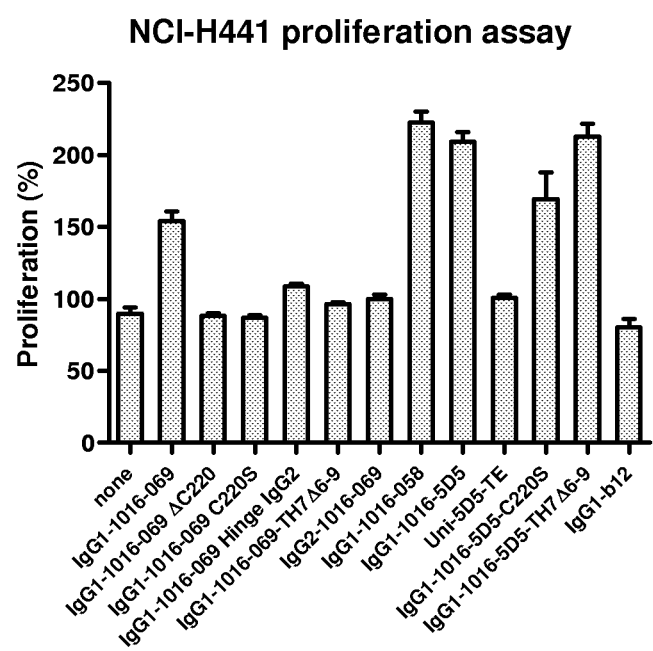

FIG. 16: Proliferation assay with NCI-H441 cells. Cell mass was determined after 7 days incubation in the presence of antibody or controls and plotted as percentage of non-treated samples (set as 100%).

Figure 17:
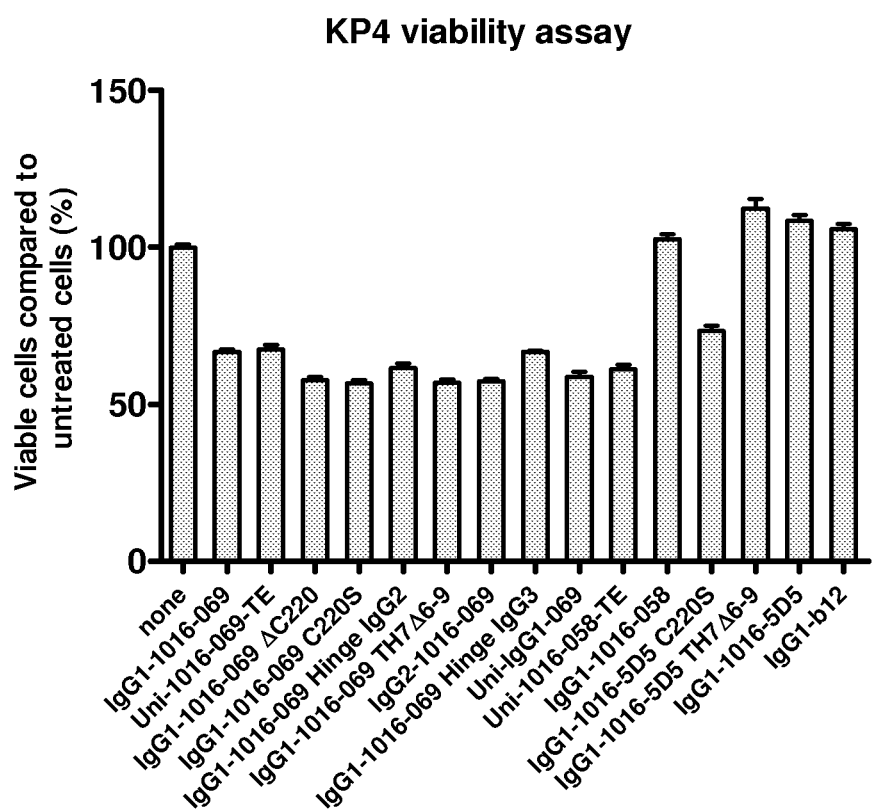

FIG. 17: KP4 viability assay. The effect of antibodies against c-Met on the overall viability of KP4 cells was tested. The ability of IgG1-1016-069 to reduce the viability of KP4 was retained and/or improved by introducing mutations that decrease the flexibility of the antibodies.

Figure 18:
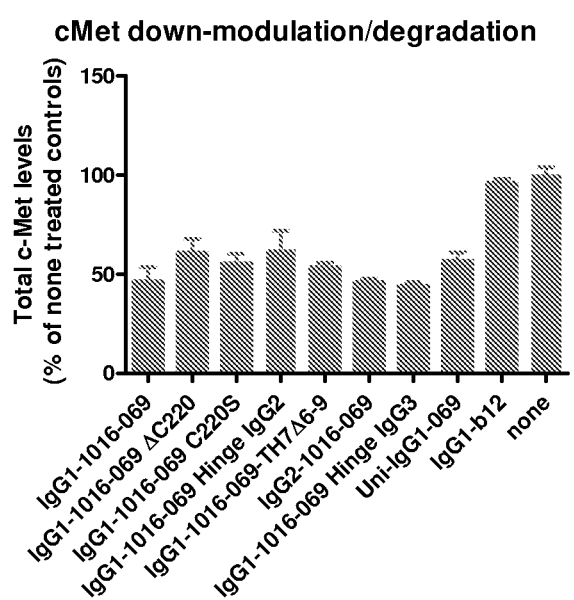

FIG. 18: Down-modulation as measured as total c-Met levels in A549 lysates using ELISA. All variants of antibody (069) retained the down-modulating capacity.

Figure 19:
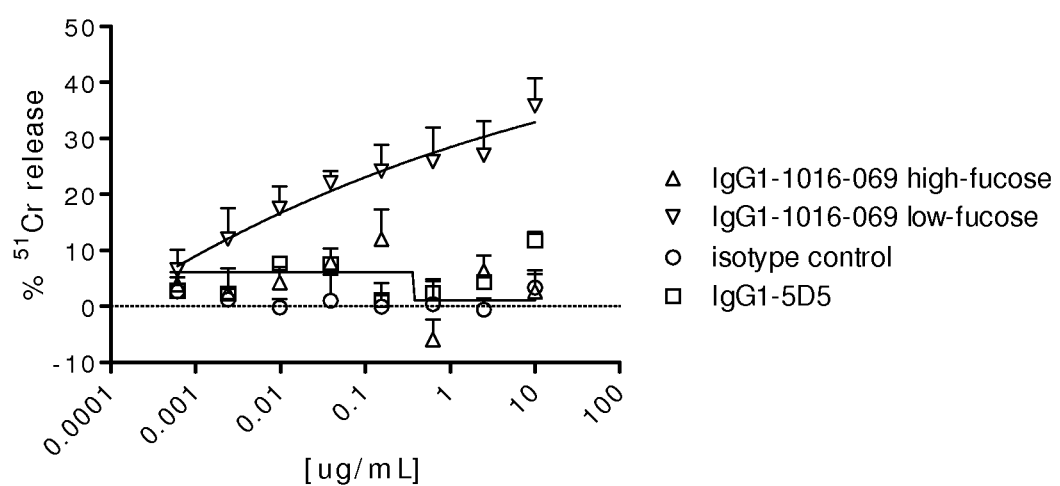

FIG. 19: ADCC assay to compare high and low fucose versions of antibody IgG1-1016-069.

Figure 20:
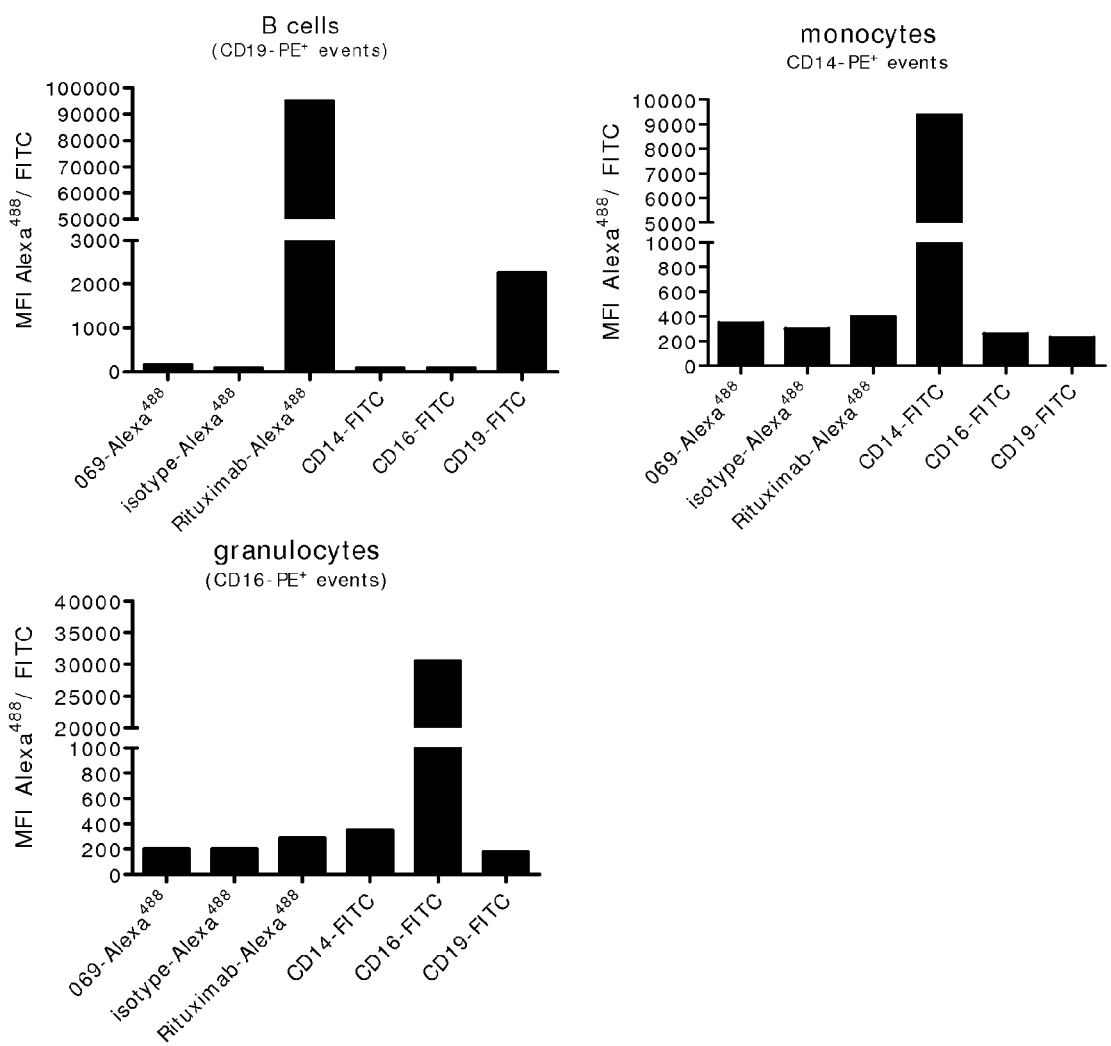

FIG. 20: Lack of binding of c-Met antibodies to cells in whole blood in FACS binding assay. Results are shown for B cells; monocytes and granulocytes.

DETAILED DESCRIPTION OF THE INVENTION

Definitions

The term "c-Met", when used herein, refers to the hepatocyte growth factor receptor (Genbank accession NM 000245) and includes any variants, isoforms and species homologs of human c-Met which are naturally expressed by cells or are expressed on cells transfected with the c-Met gene.

The term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An anti-c-Met antibody may also be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of c-Met. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementary determining region (CDR). Furthermore, although the two domains of the Fv fragment, $V_L$ and $V_H$ are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

As used herein, "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not able of antigen crosslinking.

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is IgG4.

An "anti-c-Met antibody" is an antibody as described above, which binds specifically to the antigen c-Met.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

In a preferred embodiment, the antibody of the invention is isolated. An "isolated antibody," as used herein, is intended to refer to an antibody which is substantially free of other antibodies having different antigenic specificities (for instance an isolated antibody that specifically binds to c-Met is substantially free of antibodies that specifically bind antigens other than c-Met). An isolated antibody that specifically binds to an epitope, isoform or variant of human c-Met may, however, have cross-reactivity to other related antigens, for instance from other species (such as c-Met species homologs). Moreover, an isolated antibody may be substantially free of other cellular material and/or chemicals. In one embodiment of the present invention, two or more "isolated" monoclonal antibodies having different antigen-binding specificities are combined in a well-defined composition.

When used herein in the context of two or more antibodies, the term "competes with" or "cross-competes with" indicates that the two or more antibodies compete for binding to c-Met, e.g. compete for c-Met binding in the assay described in the Examples herein. For some pairs of antibodies, competition in the assay of Examples is only observed when one antibody is coated on the plate and the other is used to compete, and not vice versa. The term "competes with" when used herein is also intended to cover such combinations antibodies.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The terms "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" ($sec^{-1}$), as used herein, refers to the dissociation rate constant of a particular antibody-antigen interaction. Said value is also referred to as the $k_{off}$ value.

The term "$k_a$" ($M^{-1} \times sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $K_a$ by the $k_d$.

As used herein, the term "inhibits growth" (e.g. referring to cells, such as tumor cells) is intended to include any measurable decrease in the cell growth when contacted with an anti-c-Met antibody as compared to the growth of the same cells not in contact with an anti-c-Met antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g. effector cell phagocytosis, ADCC, CDC, and/or apoptosis.

The present invention also provides antibodies comprising functional variants of the $V_L$ region, $V_H$ region, or one or more CDRs of the antibodies of the examples. A functional variant of a $V_L$, $V_H$, or CDR used in the context of an anti-c-Met antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-c-Met antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The sequence of CDR variants may differ from the sequence of the CDR of the parent antibody sequences through mostly conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following table:

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-c-Met antibodies when immunized with c-Met antigen and/or cells expressing c-Met. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Similar mice, having a larger human Ab gene repertoire, include HCo7 and HCo20 (see e.g. WO2009097006). Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an anti-c-Met antibody may vary according to factors such as the disease state, age, sex, and weight of the individual, and the ability of the anti-c-Met antibody to elicit a desired response in the individual. A therapeutically effective amount is also one in which any toxic or detrimental effects of the antibody or antibody portion are outweighed by the therapeutically beneficial effects.

An "anti-idiotypic" antibody is an antibody which recognizes unique determinants generally associated with the antigen-binding site of an antibody.

Further Aspects and Embodiments of the Invention

As described above, in a first aspect, the invention relates to a monoclonal antibody which binds human c-Met.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed against c-Met may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (µ and γ) and κ light chain immunoglobulin sequences, together with targeted mutations that inactivate the endogenous p and K chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

In one embodiment, the antibody of the invention is of isotype IgG1, IgG2, IgG3, IgG4, IgD, IgA, IgE, or IgM.

In a first main embodiment of the antibody of the invention, the antibody competes for binding to soluble cMetECDHis with an immobilized antibody, wherein said immobilized antibody comprises a VH region comprising the sequence of SEQ ID NO:33 and a VL region comprising the sequence of SEQ ID NO:37 (024), preferably wherein the antibody competes for more than 50%, such as more than 75% with said immobilized antibody, when determined as described in Example 17.

In a further embodiment, the antibody does not compete for binding to soluble cMetECDHis with an antibody selected from the group consisting of:
  a) an immobilized antibody comprising a VH region comprising the sequence of SEQ ID NO:1 and a VL region comprising the sequence of SEQ ID NO:5 (005)
  b) an immobilized antibody comprising a VH region comprising the sequence of SEQ ID NO:17 and a VL region comprising the sequence of SEQ ID NO:21 (008)
  c) an immobilized antibody comprising the VH region and the VL region of antibody 5D5, and
  d) an immobilized antibody comprising a VH region comprising the sequence of SEQ ID NO:49 and a VL region comprising the sequence of SEQ ID NO:53 (045),
preferably wherein the antibody competes for less than 25%, such as less than 20% with said immobilized antibody, when determined as described in Example 17.

In a further embodiment, the antibody binds to the same epitope as an antibody selected from the group consisting of:
  a) an antibody comprising a VH region comprising the sequence of SEQ ID NO:33 and a VL region comprising the sequence of SEQ ID NO:37 (024)
  b) an antibody comprising a VH region comprising the sequence of SEQ ID NO:65 and a VL region comprising the sequence of SEQ ID NO:69 (061)
  c) an antibody comprising a VH region comprising the sequence of SEQ ID NO:73 and a VL region comprising the sequence of SEQ ID NO:77 (062)
  d) an antibody comprising a VH region comprising the sequence of SEQ ID NO:81 and a VL region comprising the sequence of SEQ ID NO:85 (064)
  e) an antibody comprising a VH region comprising the sequence of SEQ ID NO:89 and a VL region comprising the sequence of SEQ ID NO:93 (068)
  f) an antibody comprising a VH region comprising the sequence of SEQ ID NO:97 and a VL region comprising the sequence of SEQ ID NO:101 (069)
  g) an antibody comprising a VH region comprising the sequence of SEQ ID NO:113 and a VL region comprising the sequence of SEQ ID NO:117 (098)
  h) an antibody comprising a VH region comprising the sequence of SEQ ID NO:121 and a VL region comprising the sequence of SEQ ID NO:125 (101), and
  i) an antibody comprising a VH region comprising the sequence of SEQ ID NO:129 and a VL region comprising the sequence of SEQ ID NO:133 (181).

In a further embodiment, the antibody comprises a VH CDR3 region having the sequence as set forth in
  a) SEQ ID NO:36 (024)
  b) SEQ ID NO:193, such as a VH CDR3 region as set forth in SEQ ID NO:68, 76, 84 or 92 (061, 062, 064, 068)
  c) SEQ ID NO:196, such as a VH CDR3 region as set forth in SEQ ID NO:100 or 132 (069, 181)
  d) SEQ ID NO:116 (098), or
  e) SEQ ID NO:201, such as a VH CDR3 region as set forth in SEQ ID NO:124 (101).

In a further embodiment, the antibody comprises:
  a) a VH region comprising the CDR1, 2 and 3 sequences of SEQ ID NO:34, 185 and 36 and a VL region comprising the CDR1, 2 and 3 sequences of SEQ ID NO:38, 39 and 206, such as an antibody comprising a VH region comprising the CDR1, 2 and 3 sequences of SEQ ID NO:34, 35 and 36 and a VL region comprising the CDR1, 2 and 3 sequences of SEQ ID NO:38, 39 and 40 (024)
  b) a VH region comprising the CDR1, 2 and 3 sequences of SEQ ID NO:191, 192 and 193 and a VL region comprising the CDR1, 2 and 3 sequences of SEQ ID NO:78, 79 and 208, such as an antibody comprising
    a. a VH region comprising the CDR1, 2 and 3 sequences of SEQ ID NO:66, 67 and 68 and a VL region comprising the CDR1, 2 and 3 sequences of SEQ ID NO:70, 71 and 72 (061)
    b. a VH region comprising the CDR1, 2 and 3 sequences of SEQ ID NO:74, 75 and 76 and a VL region comprising the CDR1, 2 and 3 sequences of SEQ ID NO:78, 79 and 80, (062)
    c. a VH region comprising the CDR1, 2 and 3 sequences of SEQ ID NO:82, 83 and 84 and a VL region comprising the CDR1, 2 and 3 sequences of SEQ ID NO:86, 87 and 88, (064), or
    d. a VH region comprising the CDR1, 2 and 3 sequences of SEQ ID NO:90, 91 and 92 and a VL region comprising the CDR1, 2 and 3 sequences of SEQ ID NO:94, 95 and 96, (068)
  c) a VH region comprising the CDR1, 2 and 3 sequences of SEQ ID NO:194, 195 and 196 and a VL region comprising the CDR1, 2 and 3 sequences of SEQ ID NO:209, 210 and 104, such as an antibody comprising
    a. a VH region comprising the CDR1, 2 and 3 sequences of SEQ ID NO:98, 99 and 100 and a VL region comprising the CDR1, 2 and 3 sequences of SEQ ID NO:102, 103 and 104, (069), or
    b. a VH region comprising the CDR1, 2 and 3 sequences of SEQ ID NO:130, 131 and 132 and a VL region comprising the CDR1, 2 and 3 sequences of SEQ ID NO:134, 135 and 136, (181)
  d) a VH region comprising the CDR1, 2 and 3 sequences of SEQ ID NO:197, 198 and 116 and a VL region comprising the CDR1, 2 and 3 sequences of SEQ ID NO:118, 119 and 211, such as an antibody comprising a VH region comprising the CDR1, 2 and 3 sequences of SEQ ID NO:114, 115 and 116 and a VL region comprising the CDR1, 2 and 3 sequences of SEQ ID NO:118, 119 and 120 (098), or
  e) a VH region comprising the CDR1, 2 and 3 sequences of SEQ ID NO: 199, 200 and 201 and a VL region comprising the CDR1, 2 and 3 sequences of SEQ ID NO: 126, 212 and 128, such as an antibody comprising a VH region comprising the CDR1, 2 and 3 sequences of SEQ ID NO:122, 123 and 124 and a VL region comprising the CDR1, 2 and 3 sequences of SEQ ID NO:126, 127 and 128 (101).

In a further embodiment, the antibody comprises:
  a) a VH region comprising the sequence of SEQ ID NO:33 and, preferably, a VL region comprising the sequence of SEQ ID NO:37 (024)
  b) a VH region comprising the sequence of SEQ ID NO:61 and, preferably, a VL region comprising the sequence of SEQ ID NO:69 (061)
  c) a VH region comprising the sequence of SEQ ID NO:73 and, preferably, a VL region comprising the sequence of SEQ ID NO:77 (062)
  d) a VH region comprising the sequence of SEQ ID NO:81 and, preferably, a VL region comprising the sequence of SEQ ID NO:85 (064)
  e) a VH region comprising the sequence of SEQ ID NO:89 and, preferably, a VL region comprising the sequence of SEQ ID NO:93 (068)
  f) a VH region comprising the sequence of SEQ ID NO:97 and, preferably, a VL region comprising the sequence of SEQ ID NO:101 (069)
  g) a VH region comprising the sequence of SEQ ID NO:113 and, preferably, a VL region comprising the sequence of SEQ ID NO:117 (098)
  h) a VH region comprising the sequence of SEQ ID NO:121 and, preferably, a VL region comprising the sequence of SEQ ID NO:125 (101)
  i) a VH region comprising the sequence of SEQ ID NO:129 and, preferably, a VL region comprising the sequence of SEQ ID NO:133 (181)
  j) a VH region comprising the sequence of SEQ ID NO:159 and, preferably, a VL region comprising the sequence of SEQ ID NO:160 (078)
  k) a VH region comprising the sequence of SEQ ID NO:161 and, preferably, a VL region comprising the sequence of SEQ ID NO:162 (084)
  l) a VH region comprising the sequence of SEQ ID NO:163 and, preferably, a VL region comprising the sequence of SEQ ID NO:164 (063)

m) a VH region comprising the sequence of SEQ ID NO:165 and, preferably, a VL region comprising the sequence of SEQ ID NO:166 (087)

n) a VH region comprising the sequence of SEQ ID NO:137 and, preferably, a VL region comprising the sequence of SEQ ID NO:138 (066)

o) a VH region comprising the sequence of SEQ ID NO:139 and, preferably, a VL region comprising the sequence of SEQ ID NO:140 (065)

p) a VH region comprising the sequence of SEQ ID NO:141 and, preferably, a VL region comprising the sequence of SEQ ID NO:142 (082)

q) a VH region comprising the sequence of SEQ ID NO:143 and, preferably, a VL region comprising the sequence of SEQ ID NO:144 (089), or r) a variant of any of said antibodies, wherein said variant preferably has at most 1, 2 or 3 amino-acid modifications, more preferably amino-acid substitutions, such as conservative amino-acid substitutions in said sequences.

In one embodiment, the antibody comprises a VH region comprising the CDR3 sequence of SEQ ID NO:100 and a VL region comprising the CDR3 sequence of SEQ ID NO: 104, (069).

In one embodiment, the antibody comprises a VH region comprising the CDR1, 2 and 3 sequences of SEQ ID NO:98, 99 and 100 and a VL region comprising the CDR1, 2 and 3 sequences of SEQ ID NO:102, 103 and 104 (069).

In one embodiment, the antibody comprises a VH region comprising the sequence of SEQ ID NO:97 and a VL region comprising the sequence of SEQ ID NO:101 (069).

In another main embodiment of the antibody of the invention:

the antibody competes for binding to soluble cMetECDHis with an immobilized antibody, wherein said immobilized antibody comprises a VH region comprising the sequence of SEQ ID NO:9 and a VL region comprising the sequence of SEQ ID NO:13 (006), preferably wherein the antibody competes for more than 50%, such as more than 75% with said immobilized antibody, when determined as described in Example 17, and the antibody does not compete binding to soluble cMetECDHis with an immobilized antibody comprising a VH region comprising the sequence of SEQ ID NO:49 and a VL region comprising the sequence of SEQ ID NO:53 (045), preferably wherein the antibody competes less than 50%, e.g. less than 25%, such as less than 20% with said immobilized antibody, when determined as described in Example 17 and the antibody binds to the SEMA domain of c-Met, preferably wherein the antibody is able to inhibit binding of HGF to the SEMA domain with an IC50 of less than 10 μg/mL, such as less than 2 μg/mL as described in Example 9.

In a further embodiment, the antibody does not compete for binding to soluble cMetECDHis with an immobilized antibody comprising a VH region comprising the sequence of SEQ ID NO:33 and a VL region comprising the sequence of SEQ ID NO:37 (024), preferably wherein the antibody competes for less than 25%, such as less than 20% with said immobilized antibody, when determined as described in Example 17.

In a further embodiment, the antibody binds to the same epitope as an antibody selected from the group consisting of:

a) an antibody comprising a VH region comprising the sequence of SEQ ID NO:1 and a VL region comprising the sequence of SEQ ID NO:5 (005)

b) an antibody comprising a VH region comprising the sequence of SEQ ID NO:9 and a VL region comprising the sequence of SEQ ID NO:13 (006)

c) an antibody comprising a VH region comprising the sequence of SEQ ID NO:25 and a VL region comprising the sequence of SEQ ID NO:29 (022), and d) an antibody comprising a VH region comprising the sequence of SEQ ID NO:57 and a VL region comprising the sequence of SEQ ID NO:61 (058).

In a further embodiment, the antibody comprises a VH CDR3 region having the sequence as set forth in a) SEQ ID NO:181, such as a VH CDR3 region as set forth in SEQ ID NO:4 or 12 (005, 006)

b) SEQ ID NO:28 (022), or c) SEQ ID NO:60 (058).

In a further embodiment, the antibody comprises:

a) a VH region comprising the CDR1, 2 and 3 sequences of SEQ ID NO:179, 180 and 181 and a VL region comprising the CDR1, 2 and 3 sequences of SEQ ID NO:6, 7 and 202, such as an antibody comprising
  a. a VH region comprising the CDR1, 2 and 3 sequences of SEQ ID NO:2, 3 and 4 and a VL region comprising the CDR1, 2 and 3 sequences of SEQ ID NO:6, 7 and 8, (005), or
  b. a VH region comprising the CDR1, 2 and 3 sequences of SEQ ID NO:10, 11 and 12 and a VL region comprising the CDR1, 2 and 3 sequences of SEQ ID NO:14, 15 and 16, (006)

b) a VH region comprising the CDR1, 2 and 3 sequences of SEQ ID NO:26, 184 and 28 and a VL region comprising the CDR1, 2 and 3 sequences of SEQ ID NO:30, 31 and 205, such as an antibody comprising a VH region comprising the CDR1, 2 and 3 sequences of SEQ ID NO:26, 27 and 28 and a VL region comprising the CDR1, 2 and 3 sequences of SEQ ID NO:30, 31 and 32 (022), or c) a VH region comprising the CDR1, 2 and 3 sequences of SEQ ID NO: 189, 190 and 60 and a VL region comprising the CDR1, 2 and 3 sequences of SEQ ID NO: 62, 63 and 207, such as an antibody comprising a VH region comprising the CDR1, 2 and 3 sequences of SEQ ID NO:58, 59 and 60 and a VL region comprising the CDR1, 2 and 3 sequences of SEQ ID NO:62, 63 and 64 (058)

In an even further embodiment, the antibody comprises:

a) a VH region comprising the sequence of SEQ ID NO:1 and, preferably, a VL region comprising the sequence of SEQ ID NO:5 (005)

b) a VH region comprising the sequence of SEQ ID NO:9 and, preferably, a VL region comprising the sequence of SEQ ID NO:13 (006)

c) a VH region comprising the sequence of SEQ ID NO:25 and, preferably, a VL region comprising the sequence of SEQ ID NO:29 (022)

d) a VH region comprising the sequence of SEQ ID NO:57 and, preferably, a VL region comprising the sequence of SEQ ID NO:61 (058)

e) a VH region comprising the sequence of SEQ ID NO:145 and, preferably, a VL region comprising the sequence of SEQ ID NO:146 (031)

f) a VH region comprising the sequence of SEQ ID NO:147 and, preferably, a VL region comprising the sequence of SEQ ID NO:148 (007)

g) a VH region comprising the sequence of SEQ ID NO:149 and, preferably, a VL region comprising the sequence of SEQ ID NO:150 (011)

h) a VH region comprising the sequence of SEQ ID NO:151 and, preferably, a VL region comprising the sequence of SEQ ID NO:152 (017)
i) a VH region comprising the sequence of SEQ ID NO:153 and, preferably, a VL region comprising the sequence of SEQ ID NO:154 (025), or
j) a variant of any of said antibodies, wherein said variant preferably has at most 1, 2 or 3 amino-acid modifications, more preferably amino-acid substitutions, such as conservative amino-acid substitutions in said sequences.

In another main embodiment of the antibody of the invention:
the antibody competes for binding to soluble cMetECDHis with an immobilized antibody, wherein said immobilized antibody comprises a VH region comprising the sequence of SEQ ID NO:49 and a VL region comprising the sequence of SEQ ID NO:53 (045), preferably wherein the antibody competes for more than 50%, such as more than 75% with said immobilized antibody, when determined as described in Example 17, and
the antibody does not compete binding to soluble cMetECDHis with an immobilized antibody, wherein said immobilized comprises a VH region comprising the sequence of SEQ ID NO:9 and a VL region comprising the sequence of SEQ ID NO:13 (006), preferably wherein the antibody competes for less than 25%, such as less than 20% with said immobilized antibody, when determined as described in Example 17.

In a further embodiment, the antibody does not compete for binding to soluble cMetECDHis with an antibody selected from the group consisting of:
a) an immobilized antibody comprising a VH region comprising the sequence of SEQ ID NO:17 and a VL region comprising the sequence of SEQ ID NO:21 (008), and
b) an immobilized antibody comprising a VH region comprising the sequence of SEQ ID NO:33 and a VL region comprising the sequence of SEQ ID NO:37 (024),
preferably wherein the antibody competes for less than 25%, such as less than 20% with said immobilized antibody, when determined as described in Example 17.

In a further embodiment, the antibody binds to the same epitope as an antibody comprising a VH region comprising the sequence of SEQ ID NO:49 and a VL region comprising the sequence of SEQ ID NO:53 (045).

In a further embodiment, the antibody comprises a VH CDR3 region having the sequence as set forth in SEQ ID NO:188, such as a VH CDR3 region as set forth in SEQ ID NO:52 (045).

In a further embodiment, the antibody comprises a VH region comprising the CDR1, 2 and 3 sequences of SEQ ID NO: 186, 187 and 188 and a VL region comprising the CDR1, 2 and 3 sequences of SEQ ID NO: 54, 55 and 56, such as an antibody comprising a VH region comprising the CDR1, 2 and 3 sequences of SEQ ID NO:50, 51 and 52 and a VL region comprising the CDR1, 2 and 3 sequences of SEQ ID NO:54, 55 and 56 (045).

In a further embodiment, the antibody comprises:
a) a VH region comprising the sequence of SEQ ID NO:49 and, preferably, a VL region comprising the sequence of SEQ ID NO:53 (045)
b) a VH region comprising the sequence of SEQ ID NO:155 and, preferably, a VL region comprising the sequence of SEQ ID NO:156 (040)
c) a VH region comprising the sequence of SEQ ID NO:157 and, preferably, a VL region comprising the sequence of SEQ ID NO:158 (039), or
d) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody binds to the SEMA domain of c-Met, preferably wherein the antibody is able to inhibit binding of HGF to the SEMA domain with an IC50 of less than 10 μg/mL, such as less than 2 μg/mL as described in Example 9.

In another main embodiment of the antibody of the invention, the antibody binds to the same epitope as an antibody comprising a VH region comprising the sequence of SEQ ID NO:17 and a VL region comprising the sequence of SEQ ID NO:21 (008) or binds to the same epitope as an antibody comprising a VH region comprising the sequence of SEQ ID NO:41 and a VL region comprising the sequence of SEQ ID NO:45 (035) or binds to the same epitope as an antibody comprising a VH region comprising the sequence of SEQ ID NO:105 and a VL region comprising the sequence of SEQ ID NO:109 (096).

In a further embodiment, the antibody comprises a VH CDR3 region having the sequence as set forth in SEQ ID NO:183, such as a VH CDR3 region as set forth in SEQ ID NO:20, 44 or 108 (008, 035, 096).

In a further embodiment, the antibody comprises a VH region comprising the CDR1, 2 and 3 sequences of SEQ ID NO:18, 182 and 183 and a VL region comprising the CDR1, 2 and 3 sequences of SEQ ID NO:22, 203 and 204, such as an antibody comprising
a) a VH region comprising the CDR1, 2 and 3 sequences of SEQ ID NO:18, 19 and 20 and a VL region comprising the CDR1, 2 and 3 sequences of SEQ ID NO:22, 23 and 24, (008), or
b) a VH region comprising the CDR1, 2 and 3 sequences of SEQ ID NO:42, 43 and 44 and a VL region comprising the CDR1, 2 and 3 sequences of SEQ ID NO:46, 47 and 48, (035), or
c) a VH region comprising the CDR1, 2 and 3 sequences of SEQ ID NO:106, 107 and 108 and a VL region comprising the CDR1, 2 and 3 sequences of SEQ ID NO:110, 111 and 112 (096).

In a further embodiment, the antibody comprises:
a) a VH region comprising the sequence of SEQ ID NO:17 and, preferably, a VL region comprising the sequence of SEQ ID NO:21 (008)
b) a VH region comprising the sequence of SEQ ID NO:41 and, preferably, a VL region comprising the sequence of SEQ ID NO:45 (035)
c) a VH region comprising the sequence of SEQ ID NO:105 and, preferably, a VL region comprising the sequence of SEQ ID NO:109 (096) or
d) a variant of any of said antibodies, wherein said variant preferably has at most 1, 2 or 3 amino-acid modifications, more preferably amino-acid substitutions, such as conservative amino-acid substitutions in said sequences.

In a further embodiment, the antibody binds to A431 cells with an EC50 of 10 nM or less, such as an EC50 of 2 nM or less, preferably as determined according to Example 13.

In an even further embodiment, the antibody binds to c-Met with an affinity constant ($K_D$) of 20 nM or less, such as an affinity of 5 nM or less, preferably as determined according to Example 14.

In an even further embodiment, the antibody binds to Rhesus c-Met, preferably wherein the signal of antibody binding to Rhesus c-Met is at least 5 times that of a negative control antibody, as determined according to Example 15.

In an even further embodiment, the antibody inhibits binding of HGF to the extracellular domain of c-Met, preferably wherein the antibody inhibits binding more than 40%, such as more than 50%, e.g. more than 60%, e.g. more than 70%, e.g. more than 80%, e.g. more than 90%, as determined according to Example 16.

In a yet even further embodiment, the antibody is capable of inhibit the viability of KP4 cells, preferably wherein the antibody is capable of inhibit the viability of more than 10%, such as more than 25%, e.g. more than 40%, preferably as described in Example 19.

Antibody Formats

The present invention provides antagonistic and non-antagonistic anti-c-Met antibodies. Whereas some antibodies act antagonistically on target cells regardless of whether they are monovalent or bivalent, for other antibodies, the functional effect depends on the valency. As shown in Example 19 herein, antibodies 024, 062, 064, 068, 069, 098, 101, 181, for instance, (which are all in the same cross-blocking group see Example 17) have antagonistic properties in a KP4 viability assay regardless of the format. Antibodies 022 and 058, on the other hand, behave antagonistically in this assay in a monovalent format, but agonistically (or at least non-antagonistically) in a bivalent format. Thus, depending on the desired functional properties for a particular use, particular antibodies can be selected from the set of antibodies provided in the present invention and/or their format can be adapted to change the valency.

Furthermore, the antibody of the invention can be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-c-Met antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

Down-modulation of c-Met induced by antagonistic antibodies represents a mechanism of action of therapeutic c-Met antibodies. Accordingly, in one aspect of the invention antibodies with reduced agonistic properties, but with retained ability to induce down-modulation of c-Met are desirable.

It has been discovered that by reducing the conformational flexibility of the antibodies the potential residual agonistic activity of the bivalent IgG1 antibodies are minimized.

Accordingly, in a further embodiment, the antibody of the invention has been modified to make it less flexible, such as by hinge region mutations.

The largest conformational changes are the result of the flexibility of the hinge, which allows a wide range of Fab-Fc angles (Ollmann Saphire, E., R. L. Stanfield, M. D. M. Crispin, P. W. H. I. Parren, P. M. Rudd, R. A. Dwek, D. R. Burton and I. A. Wilson. 2002. Contrasting IgG structures reveal extreme asymmetry and flexibility. J. Mol. Biol. 319: 9-18). One way to reduce Fab-arm flexibility in immunoglobulins is to prevent the formation of disulphide bonds between the light and the heavy chain by means of genetic modification. In a natural IgG1 antibody the light chain is connected covalently with the heavy chain via a disulphide bond, connecting the C-terminal cysteine of the light chain to the cysteine at position 220 (C220 EU numbering) in the hinge of the Fc of the heavy chain. By either mutating amino acid C220 to serine or any other natural amino acid, or removing C220 by removing the complete hinge, or by replacing the IgG1 hinge with an IgG3 hinge, a molecule is formed in which the light chains are connected via their C-terminal cysteines, analogous to the situation found in the human isotype IgA2m(1). This results in a reduced flexibility of the Fabs relative to the Fc and consequently reduced cross-linking capacity, as shown in the Examples.

Another strategy to reduce the flexibility of an IgG1 molecule is to replace the IgG1 hinge with the IgG2 hinge or IgG2-like hinge. (Dangl et al. EMBO J. 1988; 7:1989-94). This hinge region has two properties distinct from that of IgG1, which are considered to render the molecules less flexible. First, compared to IgG1 hinge the IgG2 hinge is 3 amino acids shorter. Second, the IgG2 hinge contains an additional cysteine, thus three instead of two inter-heavy chain disulphide bridges will be formed. Alternatively, a variant of the IgG1 hinge that resembles the IgG2 hinge can be introduced. This mutant (TH746-9) (WO2010063746) contains mutation T223C and two deletions (K222 and T225) in order to create a shorter hinge with an additional cysteine.

In a further embodiment, the antibody of the invention is of the IgG1 subtype, wherein the hinge region has been modified by:
(i) deleting the hinge region of the sequence EPKSCDKTHTCPPCP (SEQ ID NO: 214) and substituting it with the IgG2 hinge region of the sequence: ERKCCVECPPCP (SEQ ID NO: 215) (IgG1 Hinge-IgG2);
(ii) deleting position 220 so the modified hinge region has the sequence of EPKSDKTHTCPPCP (SEQ ID NO: 216) (IgG1 ΔC220);
(iii) substituting cysteine at position 220 with any other natural amino acid (X) so the modified hinge region has the sequence of EPKSXDKTHTCPPCP (SEQ ID NO: 217) (IgG1 C220X);
(iv) deleting the hinge region of sequence EPKSCDKTHTCPPCP (SEQ ID NO: 214) (UniBody IgG1);
(v) deleting the hinge region of the sequence EPKSCDKTHTCPPCP (SEQ ID NO: 214) and substituting it with the IgG3 hinge region of the sequence ELKTPLGDTTHTCPRCPEPKSCDTPPPCPRCPEPKSCDTPPPCPRCPEPKSCDTPPPCPRCP (SEQ ID NO: 218) (IgG1 Hinge-IgG3); or
(vi) substituting threonine at position 223 with cysteine, and deleting lysine at position 222 and threonine at position 225, so the modified hinge region has the sequence of EPKSCDCHCPPCP (SEQ ID NO: 219) (IgG1 TH7Δ6-9).

In one embodiment of the invention, the antibody of the invention is of the IgG1 subtype, wherein the hinge region has been modified by deleting position 220 so the modified hinge region has the sequence of EPKSDKTHTCPPCP (SEQ ID NO: 216) (IgG1 ΔC220) or by substituting cysteine at position 220 with any other natural amino acid (X) so the modified hinge region has the sequence of EPKSXDKTHTCPPCP (SEQ ID NO: 217) (IgG1 C220X);

In a further embodiment, the antibody of the invention is of the IgG1 subtype, wherein the hinge region has been modified by substituting cysteine at position 220 with serine so the modified hinge region has the sequence of EPKSSDKTHTCPPCP (SEQ ID NO: 220) (IgG1 C220S).

In a further embodiment, the antibody of the invention is of IgG2 subtype.

In a further embodiment, the antibody of the invention is glyco-engineered to reduce fucose and thus enhance ADCC, e.g. by addition of compounds to the culture media duringantibody production as described in US2009317869 or as described in van Berkel et al.(2010) Biotechnol. Bioeng. 105: 350 or by using FUT8 knockout cells, e.g. as described in Yamane-Ohnuki et al (2004) Biotechnol. Bioeng 87:614. ADCC may alternatively be optimized using the method described by Umalia et al. (1999) Nature Biotech 17:176.

In one embodiment, the antibody comprises a VH region comprising the CDR3 sequence of SEQ ID NO:100 and a VL region comprising the CDR3 sequence of SEQ ID NO: 104 (069) of the IgG1 subtype, wherein the hinge region has been modified by substituting cysteine at position 220 with serine so the modified hinge region has the sequence of EPKSSDKTHTCPPCP (SEQ ID NO: 220) (IgG1C220S).

In one embodiment, the antibody comprises a VH region comprising the CDR1, 2 and 3 sequences of SEQ ID NO:98, 99 and 100 and a VL region comprising the CDR1, 2 and 3 sequences of SEQ ID NO:102, 103 and 104 (069) of the IgG1 subtype, wherein the hinge region has been modified by substituting cysteine at position 220 with serine so the modified hinge region has the sequence of EPKSSDKTHTCPPCP (SEQ ID NO: 220) (IgG1 C220S).

In one embodiment, the antibody comprises a VH region comprising the sequence of SEQ ID NO:97 and a VL region comprising the sequence of SEQ ID NO:101 (069) of the IgG1 subtype, wherein the hinge region has been modified by substituting cysteine at position 220 with serine so the modified hinge region has the sequence of EPKSSDKTHTCPPCP (SEQ ID NO: 220) (IgG1 C220S).

Various publications have demonstrated the correlation between reduced core-fucosylation and enhanced ADCC activity in vitro (Shields R L. 2002 JBC; 277:26733-26740, Shinkawa T. 2003 JBC; 278(5):3466-3473, Umaña P. Nat Biotechnol. 1999 February; 17(2):176-80).

In a further embodiment, the antibody of the invention has been modified to reduce core-fucosylation below 10%, such as below 5% as determined with high performance anion-exchange chromatography coupled with pulsed amperometric detection (HPAEC-PAD). This may be achieved by methods well known in the prior art, e.g. kifunensine treatment or production in FUT8 negative cells.

In a further embodiment, the antibody of the invention has been engineered to enhance complement activation, e.g. as described in Natsume et al. (2009) Cancer Sci. 100:2411.

In one embodiment, the antibody of the invention is a full-length antibody, preferably an IgG1 antibody, in particular an IgG1,κ antibody. In another embodiment, the antibody of the invention is an antibody fragment or a single-chain antibody.

Antibodies fragments may e.g. be obtained by fragmentation using conventional techniques, and the fragments screened for utility in the same manner as described herein for whole antibodies. For example, F(ab')$_2$ fragments may be generated by treating antibody with pepsin. The resulting F(ab')$_2$ fragment may be treated to reduce disulfide bridges to produce Fab' fragments. Fab fragments may be obtained by treating an IgG antibody with papain; Fab' fragments may be obtained with pepsin digestion of IgG antibody. An F(ab') fragment may also be produced by binding Fab' described below via a thioether bond or a disulfide bond. A Fab' fragment is an antibody fragment obtained by cutting a disulfide bond of the hinge region of the F(ab')$_2$. A Fab' fragment may be obtained by treating an F(ab')$_2$ fragment with a reducing agent, such as dithiothreitol. Antibody fragment may also be generated by expression of nucleic acids encoding such fragments in recombinant cells (see for instance Evans et al., J. Immunol. Meth. 184, 123-38 (1995)). For example, a chimeric gene encoding a portion of an F(ab')$_2$ fragment could include DNA sequences encoding the $C_H1$ domain and hinge region of the H chain, followed by a translational stop codon to yield such a truncated antibody fragment molecule.

As explained above, in one embodiment, the anti-c-Met antibody of the invention is a bivalent antibody.

In another embodiment, the anti-c-Met antibody of the invention is a monovalent antibody.

In one embodiment, the antibody of the invention is a Fab fragment or a one-armed antibody, such as described in US20080063641 (Genentech) or other monovalent antibody, e.g. such as described in WO2007048037 (Amgen).

In a preferred embodiment, a monovalent antibody has a structure as described in WO2007059782 (Genmab) (incorporated herein by reference) having a deletion of the hinge region. Accordingly, in one embodiment, the antibody is a monovalent antibody, wherein said anti-c-Met antibody is constructed by a method comprising:

i) providing a nucleic acid construct encoding the light chain of said monovalent antibody, said construct comprising a nucleotide sequence encoding the VL region of a selected antigen specific anti-c-Met antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;

ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;

iii) providing a cell expression system for producing said monovalent antibody;

iv) producing said monovalent antibody by co-expressing the nucleic acid constructs of (i) and (ii) in cells of the cell expression system of (iii).

Similarly, in one embodiment, the anti-c-Met antibody is a monovalent antibody, which comprises (i) a variable region of an antibody of the invention as described herein or an antigen binding part of the said region, and (ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

In a further embodiment hereof, the heavy chain of the monovalent anti-c-Met antibody has been modified such that the entire hinge has been deleted.

In another further embodiment, said monovalent antibody is of the IgG4 subtype, but the $C_H3$ region has been modified so that one or more of the following amino acid substitutions have been made:

| KABAT* | EU index G4* | Mutations |
|---|---|---|
| | Numbering of CH3 mutations | |
| E378 | E357 | E357A or E357T or E357V or E357I |
| S387 | S364 | S364R or S364K |
| T389 | T366 | T366A or T366R or T366K or T366N |
| L391 | L368 | L368A or L368V or L368E or L368G or L368S or L368T |
| D427 | D399 | D399A or D399T or D399S |
| F436 | F405 | F405A or F405L or F405T or F405D or F405R or F405Q or F405K or F405Y |
| Y438 | Y407 | Y407A or Y407E or Y407Q or Y407K or Y407F |
| F436 and Y438 | F405 and Y407 | (F405T and Y407E) or (F405D and Y407E) |
| D427 and Y438 | D399 and Y407 | (D399S and Y407Q) or (D399S and Y407K) or (D399S and Y407E) |

*KABAT indicates amino acid numbering according to Kabat (Kabat et al., Sequences of Proteins of Immunological Interest, 5th Ed. Public Health Service, National Institutes of Health, Bethesda, MD. (1991). EU index indicates amino acid numbering according to EU index as outlined in Kabat et al., Sequences of Proteins of Immunological Interest, 5th Ed. Public Health Service, National Institutes of Health, Bethesda, MD. (1991)).

In another further embodiment, the sequence of said monovalent antibody has been modified so that it does not comprise any acceptor sites for N-linked glycosylation.

Anti-c-Met antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-c-Met antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used.

In one embodiment, the anti-c-Met antibody of the invention is an effector-function-deficient antibody. In one embodiment, the effector-function-deficient anti-c-Met antibody is a stabilized IgG4 antibody, which has been modified to prevent Fab-arm exchange (van der Neut Kolfschoten et al. (2007) Science 317(5844):1554-7). Examples of suitable stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386 (Kirin)) and/or wherein the hinge region has been modified to comprise a Cys-Pro-Pro-Cys (SEQ ID NO: 213) sequence.

In a further embodiment, the stabilized IgG4 anti-c-Met antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys (SEQ ID NO: 213) sequence in the hinge region. Preferably, said antibody comprises a Lys or Ala residue at the position corresponding to 409 or the CH3 region of the antibody has been replaced by the CH3 region of human IgG1, of human IgG2 or of human IgG3. See also and WO2008145142 (Genmab).

In an even further embodiment, the stabilized IgG4 anti-c-Met antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys (SEQ ID NO: 213) sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient anti-c-Met antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24):12161-12168 (2001).

Conjugates

In a further embodiment, the present invention provides an anti-c-Met antibody conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydro-testosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, Aleurites fordii proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, and enomycin toxins. Other suitable conjugated molecules include ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents, which may be administered in combination with a an anti-c-Met antibody of the present invention as described elsewhere herein, may also be candidates for therapeutic moieties useful for conjugation to an antibody of the present invention.

In another embodiment, an anti-c-Met antibody of the invention comprises a conjugated nucleic acid or nucleic acid-associated molecule. In one such facet of the present invention, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another embodiment, an anti-c-Met antibody of the invention is conjugated to an aptamer or a ribozyme.

In one embodiment, anti-c-Met antibodies comprising one or more radiolabeled amino acids are provided. A radiolabeled anti-c-Met antibody may be used for both diagnostic and therapeutic purposes (conjugation to radiolabeled molecules is another possible feature). Non-limiting examples of labels for polypeptides include 3H, 14C, 15N, 35S, 90Y, 99Tc, and 125I, 131I, and 186Re.

Anti-c-Met antibodies may also be chemically modified by covalent conjugation to a polymer to for instance increase their circulating half-life. Exemplary polymers, and methods to attach them to peptides, are illustrated in for instance U.S. Pat. Nos. 4,766,106, 4,179,337, 4,495,285 and No. 4,609, 546. Additional polymers include polyoxyethylated polyols and polyethylene glycol (PEG) (e.g., a PEG with a molecular weight of between about 1,000 and about 40,000, such as between about 2,000 and about 20,000).

Any method known in the art for conjugating the anti-c-Met antibody to the conjugated molecule(s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such antibodies may be produced by chemically conjugating the other moiety to the N-terminal side or C-terminal side of the anti-c-Met antibody or fragment thereof (e.g., an anti-c-Met antibody H or L chain) (see, e.g., Antibody Engineering Handbook, edited by Osamu Kanemitsu, published by Chijin Shokan (1994)). Such conjugated antibody derivatives may also be generated by conjugation at internal residues or sugars, where appropriate. The agents may be coupled either directly or indirectly to an anti-c-Met antibody of the present invention. One example of indirect coupling of a second agent is coupling by a spacer moiety. In one embodiment, the anti-c-Met antibody of the present invention is attached to a chelator linker, e.g. tiuxetan, which allows for the antibody to be conjugated to a radioisotope.

Bispecific Antibodies

In a further aspect, the invention relates to a bispecific molecule comprising a first antigen binding site from an anti-c-Met antibody of the invention as described herein above and a second antigen binding site with a different binding specificity, such as a binding specificity for a human effector cell, a human Fc receptor, a T cell receptor, a B cell receptor or a binding specificity for a non-overlapping epitope of c-Met, i.e. a bispecific antibody wherein the first and second antigen binding sites do not compete for binding to c-Met, e.g. when tested as described in Example 17.

Exemplary bispecific antibody molecules of the invention comprise (i) two antibodies one with a specificity to c-Met and another to a second target that are conjugated together, (ii) a single antibody that has one chain or arm specific to c-Met and a second chain or arm specific to a second molecule, and (iii) a single chain antibody that has specificity to c-Met and a second molecule. In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, C-myc, Marti, MelanA, MUM-1, MUM-2, MUM-3, HLA-B7, Ep-CAM or a cancer-associated integrin, such as α5β3 integrin. In another embodiment, the second molecule is an angiogenic factor or other cancer-associated growth factor, such as a vascular endothelial growth factor, a fibroblast growth factor, epidermal growth factor, angiogenin or a receptor of any of these, particularly receptors associated with cancer progression (for instance one of the HER1-HER4 receptors). In one embodiment, a bispecific antibody of the present invention is a diabody.

Nucleic Acid Sequences, Vectors and Host Cells

In a further aspect, the invention relates to nucleic acid sequences, such as DNA sequences, encoding heavy and light chains of an antibody of the invention.

In one embodiment, the nucleic acid sequence encodes an amino acid sequence selected from the group consisting of: SEQ ID NO: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177 and 178.

In another particular embodiment, the nucleic acid sequence encodes a VH amino acid sequence selected from the group consisting of: SEQ ID NO: 1, 9, 17, 25, 33, 41, 49, 57, 65, 73, 81, 89, 97, 105, 113, 121, 129, 137, 139, 141, 143, 145, 147, 149, 151, 153, 155, 157, 159, 161, 163, 165, 167, 169, 171, 173, 175 and 177.

In another particular embodiment, the nucleic acid sequence encodes a VL amino acid sequence selected from the group consisting: SEQ ID NO: 5, 13, 21, 29, 37, 45, 53, 61, 69, 77, 85, 93, 101, 109, 117, 125, 133, 138, 140, 142, 144, 146, 148, 150, 152, 154, 156, 158, 160, 162, 164, 166, 168, 170, 172, 174, 176 and 178.

In an even further aspect, the invention relates to an expression vector, or a set of expression vectors, encoding an antibody of the invention. The heavy and light chain of the antibody may be encoded by the same vector or by different vector.

Such expression vectors may be used for recombinant production of antibodies of the invention.

In one embodiment, the expression vector of the invention comprises a nucleotide sequence encoding one or more of the amino acid sequences selected from the group consisting of: SEQ ID NO: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177 and 178.

In another particular embodiment, the expression vector of the invention comprises a nucleotide sequence encoding one or more of the VH amino acid sequences selected from the group consisting of: SEQ ID NO: 1, 9, 17, 25, 33, 41, 49, 57, 65, 73, 81, 89, 97, 105, 113, 121, 129, 137, 139, 141, 143, 145, 147, 149, 151, 153, 155, 157, 159, 161, 163, 165, 167, 169, 171, 173, 175 and 177.

In another particular embodiment, the expression vector of the invention comprises a nucleotide sequence encoding one or more of the VL amino acid sequences selected from the group consisting of: SEQ ID NO: 5, 13, 21, 29, 37, 45, 53, 61, 69, 77, 85, 93, 101, 109, 117, 125, 133, 138, 140, 142, 144, 146, 148, 150, 152, 154, 156, 158, 160, 162, 164, 166, 168, 170, 172, 174, 176 and 178.

In a further embodiment, the expression vector further comprises a nucleotide sequence encoding the constant region of a light chain, a heavy chain or both light and heavy chains of an antibody, e.g. a human antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-c-Met antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and No. 5,973,972).

In one embodiment, the vector is suitable for expression of the anti-c-Met antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley Inter-Science New York (1987), and Grant et al., Methods in Enzymol 153, 516-544 (1987)).

An expression vector may also or alternatively be a vector suitable for expression in mammalian cells, e.g. a vector comprising glutamine synthetase as a selectable markers, such as the vectors described in (Bebbington (1992) Biotechnology (NY) 10:169-175).

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

In an expression vector of the invention, anti-c-Met antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the anti-c-Met-antibody-encoding expression vector may be positioned in and/or delivered to the host cell or host animal via a viral vector.

In an even further aspect, the invention relates to a recombinant eukaryotic or prokaryotic host cell, such as a transfectoma, which produces an antibody of the invention as defined herein. Examples of host cells include yeast, bacterial, and mammalian cells, such as CHO or HEK cells. For example, in one embodiment, the present invention provides a cell comprising a nucleic acid stably integrated into the cellular genome that comprises a sequence coding for expression of an anti-c-Met antibody of the present invention. In another embodiment, the present invention provides a cell comprising a non-integrated nucleic acid, such as a plasmid, cosmid, phagemid, or linear expression element, which comprises a sequence coding for expression of an anti-c-Met antibody of the invention.

In a further aspect, the invention relates to a hybridoma which produces an antibody of the invention as defined herein. In an even further aspect, the invention relates to a transgenic non-human animal or plant comprising nucleic acids encoding a human heavy chain and a human light chain, wherein the animal or plant produces an antibody of the invention of the invention.

In a further aspect, the invention relates to a method for producing an anti-c-Met antibody of the invention, said method comprising the steps of
a) culturing a hybridoma or a host cell of the invention as described herein above, and
b) purifying the antibody of the invention from the culture media.

Compositions

In a further main aspect, the invention relates to a pharmaceutical composition comprising:
an anti-c-Met antibody as defined herein, and
a pharmaceutically-acceptable carrier.

The pharmaceutical composition of the present invention may contain one antibody of the present invention or a combination of different antibodies of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Uses

In a further main aspect, the invention relates to an anti-c-Met antibody of the invention for use as a medicament.

The anti-c-Met antibodies of the invention may be used for a number of purposes. In particular, the antibodies of the invention may be used for the treatment of various forms of cancer, including metastatic cancer and refractory cancer. Such cancer may be HGF-dependent or HGF-independent.

In one embodiment, the anti-c-Met antibodies of the invention are used for the treatment of a form of cancer selected from the group consisting of: bladder cancer, breast cancer, cervical cancer, cholangiocarcinoma, colorectal cancer, endometrial cancer, esophogeal cancer, gastric cancer, head and neck cancer, kidney cancer, liver cancer, lung cancer (such as non-small cell lung cancer (NSCLC)), nasopharyngeal cancer, ovarian cancer, pancreatic cancer, gall bladder cancer, prostate cancer and thyroid cancer.

In another embodiment, the anti-c-Met antibodies of the invention are used for the treatment of a form of cancer selected from the group consisting of: osteosarcoma, rhabdomyosarcoma and synovial sarcoma.

In another embodiment, the anti-c-Met antibodies of the invention are used for the treatment of a form of cancer selected from the group consisting of: Kaposi's sarcoma, leiomyosarcoma, malignant fibrous histiocytoma and fibrosarcoma.

In another embodiment, the anti-c-Met antibodies of the invention are used for the treatment of hematopoietic malignancies, such as a malignancy selected from the group consisting of: acute myelogenous leukemia, adult T cell leukemia, chronic myeloid leukemia, lymphoma and multiple myeloma.

In a further embodiment, the anti-c-Met antibodies of the invention are used for the treatment of a neoplasm selected from the group consisting of: glioblastoma, astrocytoma, melanoma, mesothelioma and Wilm's tumor.

In a further embodiment, the anti-c-Met antibodies of the invention are used for the treatment of MiT tumors, including clear cell sarcoma (CCS), alveolar soft part sarcoma (ASPS) and translocation-associated renal cell carcinoma.

In another embodiment, agonistic anti-c-Met antibodies of the invention are used for the regulation of cytokine production and the induction of endothelial progenitor cell mobilization, e.g. in patients with coronary heart disease (Yang et al. (2009) Clin Exp Pharmacol Physiol. 36:790).

In another embodiment, agonistic anti-c-Met antibodies of the invention are used for inhibiting or improving chronic renal failure (Mizuno et al. (2008) Front Biosci. 13:7072).

Similarly, the invention relates to a method for inhibiting growth and/or proliferation of a tumor cell expressing c-Met, comprising administration, to an individual in need thereof, of an effective amount of an antibody of the invention.

In one embodiment, said tumor cell is involved in a form of cancer selected from the group consisting of: bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal cancer, ovarian cancer, pancreatic cancer, gall bladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, acute myelogenous leukemia, adult T cell leukemia, chronic myeloid leukemia, lymphoma, multiple myeloma, glioblastoma, astrocytoma, melanoma, mesothelioma and Wilm's tumor.

Also, the invention relates to the use of a monoclonal antibody that binds to human c-Met for the preparation of a medicament for the treatment of cancer, such as one of the specific cancer indications mentioned above.

In an embodiment, selection of patients to be treated with an anti-c-Met antibody is based on the level of (over)expression of c-Met and/or HGF on the relevant tumor cells of said patients.

In a further embodiment of the methods of treatment of the present invention, the efficacy of the treatment is being monitored during the therapy, e.g. at predefined points in time, by determining c-Met expression levels on the relevant tumor cells.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the anti-c-Met antibodies depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the anti-c-Met antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Administration may e.g. be parenteral, such as intravenous, intramuscular or subcutaneous. In one embodiment, the anti-c-Met antibodies may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours. In one embodiment, the anti-c-Met antibodies may be administered by slow continuous infusion over a long period, such as more than 24 hours, in order to reduce toxic side effects.

In one embodiment the anti-c-Met antibodies may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-c-Met antibodies of the present invention.

In one embodiment, the anti-c-Met antibodies may be administered by maintenance therapy, such as, e.g., once a week for a period of 6 months or more.

An anti-c-Met antibody may also be administered prophylactically in order to reduce the risk of developing cancer, delay the onset of the occurrence of an event in cancer progression, and/or reduce the risk of recurrence when a cancer is in remission.

Anti-c-Met antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing c-Met as described above, which methods comprise administration of an anti-c-Met antibody of the present invention combined with one or more additional therapeutic agents as described below.

In one embodiment, the present invention provides a method for treating a disorder involving cells expressing c-Met in a subject, which method comprises administration of a therapeutically effective amount of an anti-c-Met antibody of the present invention and at least one additional therapeutic agent to a subject in need thereof.

In one embodiment, the present invention provides a method for treating or preventing cancer, which method comprises administration of a therapeutically effective amount of an anti-c-Met antibody of the present invention and at least one additional therapeutic agent to a subject in need thereof.

In one embodiment, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In another embodiment, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In another embodiment, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In another embodiment, such an additional therapeutic agent may be selected from a topoisomerase inhibitor, such as topotecan or irinotecan, or a cytostatic drug, such as etoposide and teniposide.

In another embodiment, such an additional therapeutic agent may be selected from a growth factor inhibitor, such as an inhibitor of ErbB1 (EGFR) (such as an anti-EGFR antibody, e.g. zalutumumab, cetuximab, panitumumab or nimotuzumab or other EGFR inhibitors, such as gefitinib or erlotinib), an inhibitor of ErbB2 (Her2/neu) (such as an anti-HER2 antibody, e.g. trastuzumab, trastuzumab-DM1 or pertuzumab) or an inhibitor of both EGFR and HER2, such as lapatinib).

In another embodiment, such an additional therapeutic agent may be selected from a tyrosine kinase inhibitor, such as imatinib (Glivec, Gleevec STI571) or lapatinib, PTK787/ZK222584.

In another embodiment, the present invention provides a method for treating a disorder involving cells expressing c-Met in a subject, which method comprises administration of a therapeutically effective amount of an anti-c-Met antibody of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicilamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF (e.g. bevacizumab), bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2).

Other examples of such inhibitors of angiogenesis, neovascularization, and/or other vascularization are anti-angiogenic heparin derivatives (e.g., heperinase III), temozolomide, NK4, macrophage migration inhibitory factor, cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other targets, such as anti-alpha-v/beta-3 integrin and anti-kininostatin antibodies.

In one embodiment, a therapeutic agent for use in combination with an anti-c-Met antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines) or tumor-derived heat shock proteins.

In one embodiment, a therapeutic agent for use in combination with an anti-c-Met antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3, ligand, stem cell factor, ancestim, and TNFα. Suitable chemokines may include Glu-Leu-Arg (ELR)-negative chemokines such as IP-10, MCP-3, MIG, and SDF-1α from the human CXC and C-C chemokine families. Suitable cytokines include cytokine derivatives, cytokine variants, cytokine fragments, and cytokine fusion proteins.

In one embodiment, a therapeutic agent for use in combination with an anti-c-Met antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and No. 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In one embodiment, a therapeutic agent for use in combination with an anti-c-Met antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In one embodiment, a therapeutic agent for use in combination with an anti-c-Met antibody for treating the disorders as described above may be an anti-anergic agent, such ascompounds are molecules that block the activity of CTLA-4, e.g. ipilimumab.

In one embodiment, a therapeutic agent for use in combination with an anti-c-Met antibody for treating the disorders as described above may be an anti-cancer nucleic acid or an anti-cancer inhibitory RNA molecule.

Examples of other anti-cancer agents, which may be relevant as therapeutic agents for use in combination with an anti-c-Met antibody for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, RON (such as an anti-RON antibody), Sea, Tie, Tie2, Eph, Ret, Ros, Alk, LTK, PTK7 and similar agents.

Examples of other anti-cancer agents, which may be relevant as therapeutic agents for use in combination with an anti-c-Met antibody for treating the disorders as described above are estramustine and epirubicin.

Examples of other anti-cancer agents, which may be relevant as therapeutic agents for use in combination with an anti-c-Met antibody for treating the disorders as described above are a HSP90 inhibitor like 17-allyl amino geld-anamycin, antibodies directed against a tumor antigen such as PSA, CA125, KSA, integrins, e.g. integrin β1, or inhibitors of VCAM.

Examples of other anti-cancer agents, which may be relevant as therapeutic agents for use in combination with an anti-c-Met antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin). and inhibitors of "lymphocyte homing" mechanisms (such as FTY720), and agents with effects on cell signaling such as adhesion molecule inhibitors (for instance anti-LFA).

In one embodiment, the anti-c-Met antibody of the invention is for use in combination with one or more other therapeutic antibodies, such as ofatumumab, zanolimumab, daratumumab, ranibizumab, Zenapax, Simulect, Remicade, Humira, Tysabri, Xolair, raptiva and/or rituximab.

Other therapeutic antibodies which may be used in combination with the antibody of the present invention are anti-c-Met antibodies that bind to other regions of c-Met, such as the antibodies described in WO2005016382, WO2006015371, WO2007090807, WO2007126799 or WO2009007427 (all incorporated herein by reference).

In another embodiment, two or more different antibodies of the invention as described herein are used in combination for the treatment of disease. Particularly interesting combinations include two or more non-competing antibodies. Such combination therapy may lead to binding of an increased number of antibody molecules per cell, which may give increase efficacy, e.g. via activation of complement-mediated lysis.

In addition to the above, other embodiments of combination therapies of the invention include the following:

For the treatment of non-small-cell lung cancer, an anti-c-Met antibody in combination with EGFR inhibitors, such as an anti-EGFR antibody, e.g. zalutumumab, cetuximab, panitumumab or nimotuzumab or other EGFR inhibitors, such as gefitinib or erlotinib), or in combination with an an inhibitor of ErbB2 (Her2/neu) (such as an anti-HER2 antibody, e.g. trastuzumab, trastuzumab-DM1 or pertuzumab) or in combination with an inhibitor of both EGFR and HER2, such as lapatinib, or in combination with a HER3 inhibitor.

For the treatment of glioma, an anti-c-Met antibody in combination with temozolomide or an angiogenesis inhibitor, such as bevacizumab.

For the treatment of colorectal cancer an anti-c-Met antibody in combination with one or more compounds selected from: gemcitabine, bevacizumab, FOLFOX, FOLFIRI, XELOX, IFL, oxaliplatin, irinotecan, 5-FU/LV, Capecitabine, UFT, EGFR targeting agents, such as cetuximab. panitumumab, zalutumumab; VEGF inhibitors, or tyrosine kinase inhibitors such as sunitinib.

For the treatment of prostate cancer an anti-c-Met antibody in combination with one or more compounds selected from: hormonal/antihormonal therapies; such as antiandrogens, Luteinizing hormone releasing hormone (LHRH) agonists, and chemotherapeutics such as taxanes, mitoxantrone, estramustine, 5FU, vinblastine, ixabepilone, Radiotherapy—Surgery In one embodiment, the present invention provides a method for treating a disorder involving cells expressing c-Met in a subject, which method comprises administration of a therapeutically effective amount of an anti-c-Met antibody, such as an anti-c-Met antibody of the present invention, and radiotherapy to a subject in need thereof.

In one embodiment, the present invention provides a method for treating or preventing cancer, which method comprises administration of a therapeutically effective amount of an anti-c-Met antibody, such as an anti-c-Met antibody of the present invention, and radiotherapy to a subject in need thereof.

In one embodiment, the present invention provides the use of an anti-c-Met antibody, such as an anti-c-Met antibody of the present invention, for the preparation of a pharmaceutical composition for treating cancer to be administered in combination with radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of an anti-c-Met antibody, such as an anti-c-Met antibody of the present invention, in combination with surgery.

Diagnostic Uses

The anti-c-Met antibodies of the invention may also be used for diagnostic purposes. Thus, in a further aspect, the invention relates to a diagnostic composition comprising an anti-c-Met antibody as defined herein.

In one embodiment, the anti-c-Met antibodies of the present invention may be used in vivo or in vitro for diagnosing diseases wherein activated cells expressing c-Met play an active role in the pathogenesis, by detecting levels of c-Met, or levels of cells which contain c-Met on their membrane surface. This may be achieved, for example, by contacting a sample to be tested, optionally along with a control sample, with the anti-c-Met antibody under conditions that allow for formation of a complex between the antibody and c-Met.

Thus, in a further aspect, the invention relates to a method for detecting the presence of c-Met antigen, or a cell expressing c-Met, in a sample comprising:

contacting the sample with an anti-c-Met antibody of the invention under conditions that allow for formation of a complex between the antibody and c-Met; and analyzing whether a complex has been formed.

In one embodiment, the method is performed in vitro.

More specifically, the present invention provides methods for the identification of, and diagnosis of invasive cells and tissues, and other cells targeted by anti-c-Met antibodies of the present invention, and for the monitoring of the progress of therapeutic treatments, status after treatment, risk of developing cancer, cancer progression, and the like.

Suitable labels for the anti-c-Met antibody and/or secondary antibodies used in such techniques are well-known in the art.

In a further aspect, the invention relates to a kit for detecting the presence of c-Met antigen, or a cell expressing c-Met, in a sample comprising an anti-c-Met antibody of the invention or a bispecific molecule of the invention; and instructions for use of the kit.

In one embodiment, the present invention provides a kit for diagnosis of cancer comprising a container comprising an anti-c-Met antibody, and one or more reagents for detecting binding of the anti-c-Met antibody to c-Met. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

Anti-Idiotypic Antibodies

In a further aspect, the invention relates to an anti-idiotypic antibody which binds to an anti-c-Met antibody of the invention as described herein.

An anti-idiotypic (Id) antibody is an antibody which recognizes unique determinants generally associated with the antigen-binding site of an antibody. An Id antibody may be prepared by immunizing an animal of the same species and genetic type as the source of an anti-c-Met mAb with the mAb to which an anti-Id is being prepared. The immunized animal typically can recognize and respond to the idiotypic determinants of the immunizing antibody by producing an antibody to these idiotypic determinants (the anti-Id antibody).

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity.

The present invention is further illustrated by the following examples which should not be construed as further limiting.

EXAMPLES

Example 1

Expression Constructs for c-Met

Codon-optimized constructs for expression of c-Met, the extracellular domain (ECD) (aa 1-932 and a C-terminal His6 tag or the SEMA domain of c-Met (aa 1-567 and a C-terminal His9 tag), in HEK or CHO cells, were generated. The proteins encoded by these constructs are identical to Genbank accession NM 000245 for c-Met. The constructs contained suitable restriction sites for cloning and an optimal Kozak sequence (Kozak et al. (1999) Gene 234: 187-208). The constructs were cloned in the mammalian expression vector pEE13.4 (Lonza Biologics) (Bebbington (1992) Biotechnology (NY) 10:169-175), obtaining pEE13.4cMet, pEE13.4cMetECDHis and pEE13.4cMetSEMA-567His8.

Example 2

Expression Constructs for 5D5v1, 5D5 and G11-HZ

Codon-optimized constructs for expression of the heavy chain (HC) and the light chain (LC) of the IgG1 antibodies 5D5v1, 5D5 and G11-HZ in HEK cells, were generated. The proteins encoded by these constructs are identical to those described in U.S. Pat. No. 6,468,529 (sequence numbers 3 and 4) for 5D5v1 heavy chain and light chain, WO 2006/015371 A2 (FIG. 13) for 5D5 heavy chain and light chain and WO 2009/007427 A2 (sequence was extracted from multiple figures) for 224G11 heavy and light chain. 224G11 is also termed G11-HZ herein.

Example 3

Transient Expression in HEK-293F Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. Expression of c-Met was tested by means of FACS analysis as described below. In the case of antibody expression, the appropriate heavy chain and light chain expression vectors were co-expressed.

Example 4

Transient Expression in CHO Cells pEE13.4cMet was transiently transfected in Freestyle™ CHO-S (Invitrogen) cell line using Freestyle MAX transfection reagent (Invitrogen). Expression of c-Met was tested by means of FACS analysis as described below.

Example 5

Cloning and Expression of Monovalent Antibodies (UniBody® Molecules)

For the expression of monovalent antibodies in mammalian cells the HC constant region of IgG4, missing the hinge region (Ch) (amino acids E99-P110) and containing the 2 mutations F405T and Y407E in the CH3 region, was synthesized as a codon optimized construct in mammalian expression vector pcDNA3.3 (Invitrogen) and named pUniTE. A separate vector was constructed by inserting the codon optimized constant region of the human kappa light chain region in pcDNA3.3 and named pKappa.

Relevant VH and VL regions were inserted respectively in pUniTE and pKappa resulting in vectors for the expression of the heavy and light chains of the specific antibodies. Cotransfection of the heavy and light chain vectors of a specific antibody in HEK-293F (Invitrogen) cells, resulted in the transient production of monovalent antibodies with the desired specificities. Purification was performed using Protein A affinity column chromatography (as described in Example 11).

Example 6

Purification of His-Tagged c-Met cMetECDHis and cMetSEMAHis were expressed in HEK-293F cells. The His-tag in cMetECDHis and cMetSEMAHis enables purification with immobilized metal affinity chromatography. In this process, a chelator fixed onto the chromatographic resin is charged with $Co^{2+}$ cations. cMetECDHis and cMetSEMAHis containing supernatants were incubated with the resin in batch mode (i.e. solution). The His-tagged protein binds strongly to the resin beads, while other proteins present in the culture supernatant do not bind strongly. After incubation the beads are retrieved from the supernatant and packed into a column. The column is washed in order to remove weakly bound proteins. The strongly bound cMetECDHis and cMetSEMAHis proteins are then eluted with a buffer containing imidazole, which competes with the binding of His to $Co^{2+}$. The eluent is removed from the protein by buffer exchange on a desalting column.

Example 7

Immunization Procedure of Transgenic Mice

Antibodies 005, 006, 007, 008, 011, 012, 016, 017, 022, 024, 025, 028, 031, 035, 039, 040, 045, 093, 095, 096, 101 and 104 were derived from the following immunizations: one HCo20 mouse (1 female, strain GG2713), one HCo17 mouse (female, strain GG2714) and two HCo12-Balb/C mice (2 females, strain GG2811) (Medarex, San Jose, Calif., USA; for references see paragraph on HuMab mouse above, WO2009097006 and US2005191293) were immunized every fortnight alternating with $5 \times 10^6$ NCI-H441 tumor cells intraperitoneal (IP) and 20 µg of cMetECDHis protein coupled to the hapten Keyhole Limpet Hemocyanin (KLH) subcutaneous (SC).

Antibodies 058, 061, 062, 063, 064, 065, 066, 068, 069, 078, 082, 084, 087, 089, 098 and 181 were derived from the following immunizations: two HCo20 mice (1 male and 1 female, strain GG2713) and one HCo12-Balb/C mouse (1 male, strain GG2811) (Medarex, San José, Calif., USA; for references see paragraph on HuMab mouse above) were immunized every fortnight alternating with $5 \times 10^6$ CHO-K1SV cells transient transfected with cMetECD intraperitoneal (IP) and 20 µg of cMetECDHis protein coupled to the hapten Keyhole Limpet Hemocyanin (KLH) subcutaneous (SC).

A maximum of eight immunizations was performed per mouse, four IP and four SC immunizations at the tail base. The first immunization with cells was done in complete Freund's adjuvant (CFA; Difco Laboratories, Detroit, Mich., USA). For all other immunizations, cells were injected IP in PBS and KLH-coupled cMetECD was injected SC using incomplete Freund's adjuvant (IFA; Difco Laboratories, Detroit, Mich., USA). Mice with at least two sequential c-Met specific antibody titers of 200 (serum dilutions of 1/200) or higher, detected in the antigen specific screening FMAT assay as described in Example 8, were fused.

Example 8

Homogeneous Antigen Specific Screening Assay

The presence of anti-c-Met antibodies in sera of immunized mice or HuMab (human monoclonal antibody) hybridoma or transfectoma culture supernatant was determined by homogeneous antigen specific screening assays (four quadrant) using Fluorometric Micro volume Assay Technology (FMAT; Applied Biosystems, Foster City, Calif., USA). For this, a combination of 3 cell based assays and one bead based assay was used. In the cell based assays, binding to TH1016-cMet (HEK-293F cells transiently expressing the extracellular domain of the c-Met receptor; produced as described above) and HT29 (which express c-Met at the cell surface) as well as HEK293 wild-type cells (negative control which does not express c-Met) was determined. For the bead based assay, binding to SB1016-cMet (cMetECDHis obtained from transient transfected HEK-293F cells as described above, biotinylated and coupled to streptavidin-coated beads) was determined. Samples were added to the cells/beads to allow binding to c-Met. Subsequently, binding of HuMab was detected using a fluorescent conjugate (Goat anti-Human IgG-Cy5; Jackson ImmunoResearch). The chimeric c-Met specific antibody 5D5v1 (produced in HEK-293F cells) was used as a positive control and HuMab-mouse pooled serum and HuMab-KLH were used as negative controls. The samples were scanned using an Applied Biosystems 8200 Cellular Detection System (8200 CDS) and 'counts x fluorescence' was used as read-out. Samples were stated positive when counts were higher than 50 and counts x fluorescence were at least three times higher than the negative control HuMab-KLH.

Example 9

HuMab Hybridoma Generation

HuMab mice with sufficient antigen-specific titer development (defined as above) were sacrificed and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Fusion plates were screened with the antigen specific binding assay as described above and positives from this assay were tested in an ERK-phosphorylation Alphascreen® SureFire® assay and affinity ranking Octet assay as described below. Antibodies 031, 035, 087 and 089 were expanded and cultured based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

In parallel antibodies 005, 006, 007, 008, 011, 012, 016, 017, 022, 024, 025, 028, 035, 039, 040, 045, 058, 061, 062, 063, 064, 065, 066, 068, 069, 078, 082, 084, 093, 095, 096, 098, 101, 104 and 181 were cloned using the ClonePix system (Genetix, Hampshire, UK). Specific primary well hybridomas were seeded in semisolid medium made from 40% CloneMedia (Genetix, Hampshire, UK) and 60% HyQ 2x complete media (Hyclone, Waltham, USA) and approximately 100 sub clones of each primary well were picked. The sub clones were retested in the antigen specific binding assay as described previously and IgG levels were measured using Octet in order to select the best specific and producing clone per primary well for further expansion. Further expansion and culturing of the resulting HuMab hybridomas was done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

Example 10

Mass Spectrometry of Purified Antibodies

Small 0.8 ml aliquots of antibody containing hybridoma supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTip columns were used according to manufacturers instructions, but buffers were replaced by: Binding Buffer PBS (B. Braun, Medical B.V., Oss, Netherlands) and Elution Buffer 0.1M Glycine-HCl pH 2.7 (Fluka Riedel-de Haen, Buchs, Germany). After purification, samples were neutralized with 2M Tris-HCl pH 9.0 (Sigma-Aldrich, Zwijndrecht, Netherlands). Alternatively, in some cases larger volumes of culture supernatant were purified using Protein A affinity column chromatography.

After purification, the samples were placed in a 384-well plate (Waters, 100 ul square well plate, part #186002631). Samples were deglycosylated overnight at 37° C. with N-glycosidase F. DTT (15 mg/mL) was added (1 μl/well) and incubated for 1 h at 37° C. Samples (5 or 6 ul) were desalted on an Acquity UPLC™ (Waters, Milford, USA) with a BEH300 C18, 1.7 μm, 2.1×50 mm column at 60° C. MQ water and LC-MS grade acetonitrile (Biosolve, cat no 01204101, Valkenswaard, The Netherlands) with both 0.1% formic acid (Fluka, cat no 56302, Buchs, Germany), were used as Eluens A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution the resulting heavy and light chain masses for all samples were compared in order to find duplicate antibodies. In the comparison of the heavy chains the possible presence of C-terminal lysine variants was taken into account. This resulted in a list of unique antibodies, where unique is defined as a unique combination of heavy and light chains. In case duplicate antibodies were found, the results from other tests were used to decide which antibody was the best material to continue experiments with.

Example 11

Sequence Analysis of the Anti-c-Met Antibody Variable Domains and Cloning in Expression Vectors Total RNA of the anti-c-Met HuMabs was prepared from $5 \times 10^6$ hybridoma cells and 5'-RACE-Complementary DNA (cDNA) was prepared from 100 ng total RNA, using the SMART RACE cDNA Amplification kit (Clontech), according to the manufacturer's instructions. VH (variable region of heavy chain) and VL (variable region of light chain) coding regions were amplified by PCR and in frame cloned into the constant region vectors pG1f (Containing the codon optimized, fully synthetic, constant region of the heavy chain of human IgG1 (allotype f) in the mammalian expression vector pEE6.4 (Lonza Biologics, Slough, UK (Bebbington et al. (1992) Biotechnology 10:169-175)) and pKappa (Containing the codon optimized, fully synthetic, constant region of the human kappa light chain (allotype Km3) in the mammalian expression vector pEE12.4 (Lonza Biologics, Slough, UK (Bebbington et al. (1992) Biotechnology 10:169-175)) using a ligation independent cloning strategy (Aslanidis et al. 1990 Nucleic Acids Res. 18:6069-6074). For each HuMab, 12 VL clones and 8 VH clones were sequenced and their theoretical masses were calculated and compared to the available antibody mass spectrometry data. The sequences are given in the Sequence Listing and in Table 1 here below. CDR sequences are defined according to Kabat et al., Sequences of Proteins of Immunological Interest, 5th Ed. Public Health Service, National Institutes of Health, Bethesda, Md. (1991). Table 2 and Table 3 give an overview of the antibody sequence information and most homologous germline sequences.

TABLE 1

Heavy chain variable region (VH), light chain variable region (VL) and CDR sequences of HuMabs

| | | |
|---|---|---|
| SEQ ID No: 1 | VH 005 | QVQLVQSGAEVKKPGSSVKVSCKASGGTFSSYGFG WVRQAPGQGLEWMGRISPILGIANYAQMFQGRVTIT ADKSTSTAYMELSSLRSEDTAVYYCARDVGYDWPDT FDIWGQGTMVIVSS |
| SEQ ID No: 2 | VH 005, CDR1 | SYGFG |
| SEQ ID No: 3 | VH 005, CDR2 | RISPILGIANYAQMFQG |
| SEQ ID No: 4 | VH 005, CDR3 | DVGYDWPDTFDI |
| SEQ ID No: 5 | VL 005 | DIQMTQSPSSLSASVGDVTITCRASQGISSWLAWY QQKPEKAPKSLIYAASSLQSGVPSRFSGGGSGTDFTL TISSLQPEDFATYYCQQYNSFPPTFGQGTKVEIK |
| SEQ ID No: 6 | VL 005, CDR1 | RASQGISSWLA |
| SEQ ID No: 7 | VL 005, CDR2 | AASSLQS |
| SEQ ID No: 8 | VL 005, CDR3 | QQYNSFPPT |

TABLE 1-continued

Heavy chain variable region (VH), light chain variable region (VL) and CDR sequences of HuMabs

| SEQ ID No: 9 | VH 006 | QVQLVQSGAEVKKPGSSVKVSCKASGGTFSSFGIG<br>WVRQAPGQGLEWMGRIFPILGTANYAQMFQGRVTIT<br>ADKSTSTAYMELTSLRSEDTAVYYCARDVGYDSADAF<br>DIWGQGTMVTVSS |
|---|---|---|
| SEQ ID No: 10 | VH 006, CDR1 | SFGIG |
| SEQ ID No: 11 | VH 006, CDR2 | RIFPILGTANYAQMFQG |
| SEQ ID No: 12 | VH 006, CDR3 | DVGYDSADAFDI |
| SEQ ID No: 13 | VL 006 | DIQMTQSPSSLSASVGDRVTITCRASQGISSWLAWY<br>QQKPEKAPKSLIYAASSLQSGVPSRFSGSGSGTDFTL<br>TISSLQPEDFATYYCQQYNSYPPTFGQGTKVEIK |
| SEQ ID No: 14 | VL 006, CDR1 | RASQGISSWLA |
| SEQ ID No: 15 | VL 006, CDR2 | AASSLQS |
| SEQ ID No: 16 | VL 006, CDR3 | QQYNSYPPT |
| SEQ ID No: 17 | VH 008 | EVQLVQSGAEVKKPGESLKISCKGSGYSFTSYWIGW<br>VRQMPGKGLEWMGIIPGDSETRYSPSFQGQVTISA<br>DKSISTAYLQWSSLKASDTAMYYCARQEITGEFDYW<br>GQGTLVTVSS |
| SEQ ID No: 18 | VH 008, CDR1 | SYWIG |
| SEQ ID No: 19 | VH 008, CDR2 | IIYPGDSETRYSPSFQG |
| SEQ ID No: 20 | VH 008, CDR3 | QEITGEFDY |
| SEQ ID No: 21 | VL 008 | AIQLTQSPSSLSASVGDRVTITCRASQGISSAGAWYQ<br>QKPGKAPKLLIYDASSLESGVPSRFSGSGSGTDFTLTI<br>SSLQPEDFATYYCQQFNSYPRTFGQGTKVEIK |
| SEQ ID No: 22 | VL 008, CDR1 | RASQGISSALA |
| SEQ ID No: 23 | VL 008, CDR2 | DASSLES |
| SEQ ID No: 24 | VL 008, CDR3 | QQFNSYPRT |
| SEQ ID No: 25 | VH 022 | QVQLVESGGGVVQPGRSLRLSCAASGFTFSSYAMH<br>WVRQAPGKGLEWVAVISYDGSNKYYADSVKGRFTIS<br>RDNSKNTLYLQMNSLRAEDTAVYYCARELLWFGELW<br>GYFDLWGRGTLVTVSS |
| SEQ ID No: 26 | VH 022, CDR1 | SYAMH |
| SEQ ID No: 27 | VH 022, CDR2 | VISYDGSNKYYADSVKG |
| SEQ ID No: 28 | VH 022, CDR3 | ELLWFGELWGYFDL |
| SEQ ID No: 29 | VL 022 | DIQMTQSPSSVSASVGDRVTITCRASQGISSWLAWY<br>QHKPGKAPKLLIYAASSLQSGVPSRFSGSGSGTDFTL<br>TISSLQPEDFATYYCQEASSFTWTFGQGTKVEIK |
| SEQ ID No: 30 | VL 022, CDR1 | RASQGISSWLA |
| SEQ ID No: 31 | VL 022, CDR2 | AASSLQS |
| SEQ ID No: 32 | VL 022, CDR3 | QEASSFTWT |
| SEQ ID No: 33 | VH 024 | EVQLLESGGGLVQPGGSLRLSCVASGFTFSSYAMSW<br>VRQAPGKGLEWVSAISGSSGGSTYYVDSVKGRFTIS<br>RANSKNTLYLQMNSLRAEDTAVYYCAKDLDRGWMG<br>YFGYWGQGTLVTVSS |
| SEQ ID No: 34 | VH 024, CDR1 | SYAMS |
| SEQ ID No: 35 | VH 024, CDR2 | AISGSSGGSTYYVDSVKG |
| SEQ ID No: 36 | VH 024, CDR3 | DLDRGWMGYFGY |

TABLE 1-continued

Heavy chain variable region (VH), light chain variable region (VL) and CDR sequences of HuMabs

| SEQ ID No: 37 | VL 024 | DIQMTQSPSSVSASVGDRVTITCRASQGISSWLAWY QHKPGKAPKLLIYAASSLQSGVPSRFSGSGSGTDFTL TISSLQPEDFATYYCQQANSFPTFGQGTRLEIK |
|---|---|---|
| SEQ ID No: 38 | VL 024, CDR1 | RASQGISSWLA |
| SEQ ID No: 39 | VL 024, CDR2 | AASSLQS |
| SEQ ID No: 40 | VL 024, CDR3 | QQANSFPT |
| SEQ ID No: 41 | VH 035 | EVQLVQSGAEVKKPGESLKISCKGSGYSFTSYWIGW VRQMPGKGLEWMGIIYPGDSDTRYSPSFQGQVTISA DKSISTAYLQWNSLKASDTAMYYCARQEITGEFDYW GQGTLVTVSS |
| SEQ ID No: 42 | VH 035, CDR1 | SYWIG |
| SEQ ID No: 43 | VH 035, CDR2 | IIYPGDSDTRYSPSFQG |
| SEQ ID No: 44 | VH 035, CDR3 | QEITGEFDY |
| SEQ ID No: 45 | VL 035 | AIQLTQSPSSLSASVGDRVTITCRASQGISSALAWYQ QKPGKAPKLLIYDASSLESGVPSRFSGSGSGTDFTLTI SSLQPEDFATYYCQQFNSYPMYTFGQGTKLEIK |
| SEQ ID No: 46 | VL 035, CDR1 | RASQGISSALA |
| SEQ ID No: 47 | VL 035, CDR2 | DASSLES |
| SEQ ID No: 48 | VL 035, CDR3 | QQFNSYPMYT |
| SEQ ID No: 49 | VH 045 | EVQLLESGGGLVQPGGSLRLSCAASGFTFSSYAMSW VRQAPGKGLEWVSVISGSGGITYYADSVKGRFTISR DNSKNTLYLQMNSLRAEDTAVYYCARDRGWGSDYW GQGTLVTVSS |
| SEQ ID No: 50 | VH 045, CDR1 | SYAMS |
| SEQ ID No: 51 | VH 045, CDR2 | VISGSGGITYYADSVKG |
| SEQ ID No: 52 | VH 045, CDR3 | DRGWGSDY |
| SEQ ID No: 53 | VL 045 | EIVLTQSPATLSLSPGERATLSCRASQSVSSYLAWYQ QKPGQAPRLLIYDASNRATGIPARFSGSGSGTDFTLTI SSLEPEDFAVYYCQQRSNWPFTFGPGTKVDIK |
| SEQ ID No: 54 | VL 045, CDR1 | RASQSVSSYLA |
| SEQ ID No: 55 | VL 045, CDR2 | DASNRAT |
| SEQ ID No: 56 | VL 045, CDR3 | QQRSNWPFT |
| SEQ ID No: 57 | VH 058 | EVQLVESGGGLVKPGGSLKLSCAASGFTFSDYYMYW VRQTPEKRLEWVATISDDGSYTYYPDSVKGRFTISRD NAKNNLYLQMSSLKSEDTAMYYCAREGLYYYGSGSY YNQDYWGQGTLVTVSS |
| SEQ ID No: 58 | VH 058, CDR1 | DYYMY |
| SEQ ID No: 59 | VH 058, CDR2 | TISDDGSYTYYPDSVKG |
| SEQ ID No: 60 | VH 058, CDR3 | EGLYYYGSGSYYNQDY |
| SEQ ID No: 61 | VL 058 | AIQLTQSPSSLSASVGDRVTITCRASQGLSSALAWYR QKPGKAPKLLIYDASSLESGVPSRFSGSGSGTDFTLTI SSLQPEDFATYYCQQFTSYPQITFGQGTRLEIK |
| SEQ ID No: 62 | VL 058, CDR1 | RASQGLSSALA |
| SEQ ID No: 63 | VL 058, CDR2 | DASSLES |
| SEQ ID No: 64 | VL 058, CDR3 | QQFTSYPQIT |
| SEQ ID No: 65 | VH 061 | QLQLQESGSGLVKPSQTLSLTCAVSGGSISSGGHSW SWIRQPPGKGLEWIGX1IYHSGNTYDNPSLKSRVTIA VDRSKNQLSLKLSFLTAADTAVYYCARSSYDFLTDWG |

TABLE 1-continued

Heavy chain variable region (VH), light chain variable region (VL) and CDR sequences of HuMabs

| | | |
|---|---|---|
| | | QGTLVTVSS, wherein X1 is any amino acid, preferably C, S, Y or A |
| SEQ ID No: 66 | VH 061, CDR1 | SGGHSWS |
| SEQ ID No: 67 | VH 061, CDR2 | X1IYHSGNTYDNPSLKS, wherein X1 is any amino acid, preferably C, S, Y or A |
| SEQ ID No: 68 | VH 061, CDR3 | SSYDFLTD |
| SEQ ID No: 69 | VL 061 | DIQMTQSPSSVSASVGDRVTITCRASQGISSWLAWYQHKPGKAPKLLIYAASSLQSGVPSRFSGSGSGTDFTLTISSLQPEDFATYYCQQANGFPITFGQGTRLEIK |
| SEQ ID No: 70 | VL 061, CDR1 | RASQGISSWLA |
| SEQ ID No: 71 | VL 061, CDR2 | AASSLQS |
| SEQ ID No: 72 | VL 061, CDR3 | QQANGFPIT |
| SEQ ID No: 73 | VH 062 | QLQLQESGSGLVKPSQTLSLTCAVSGGSISSGGHSWSWIRQPPGKGLEWIGX1IYHSGNTYDNPSLKSRVTIAVDRSKNQLSLKLSFVTAADTAVYYCARSSYDILTDWGQGTLVTVSS, wherein X1 is any amino acid, preferably C, S, Y or A |
| SEQ ID No: 74 | VH 062, CDR1 | SGGHSWS |
| SEQ ID No: 75 | VH 062, CDR2 | X1IYHSGNTYDNPSLKS, wherein X1 is any amino acid, preferably C, S, Y or A |
| SEQ ID No: 76 | VH 062, CDR3 | SSYDILTD |
| SEQ ID No: 77 | VL 062 | DIQMTQSPSSVSASVGDRVTITCRASQGISSWLAWYQHKPGKAPKLLIYAASSLQSGVPSRFSGSGSGTDFTLTISSLQPEDFATYYCQQANGFPITFGQGTRLEIK |
| SEQ ID No: 78 | VL 062, CDR1 | RASQGISSWLA |
| SEQ ID No: 79 | VL 062, CDR2 | AASSLQS |
| SEQ ID No: 80 | VL 062, CDR3 | QQANGFPIT |
| SEQ ID No: 81 | VH 064 | QLQLQESGSGLVKPSQTLSLTCAVSGGSISSGGHSWSWIRQPPGKGLEWIGX1IYHSGNTYDNPSLKSRVTISVDRSKNQVSLKLSSVTAADTAVYYCARSSYDILTDWGQGTLVTVSS, wherein X1 is any amino acid, preferably C, S, Y or A |
| SEQ ID No: 82 | VH 064, CDR1 | SGGHSWS |
| SEQ ID No: 83 | VH 064, CDR2 | X1IYHSGNTYDNPSLKS, wherein X1 is any amino acid, preferably C, S, Y or A |
| SEQ ID No: 84 | VH 064, CDR3 | SSYDILTD |
| SEQ ID No: 85 | VL 064 | DIQMTQSPSSVSASVGDRVTITCRASQGISSWLAWYQHKPGKAPKLLIYAASSLQSGVPSRFSGSGSGTDFTLTISSLQPEDFATYYCQQANGFPITFGQGTRLEIK |
| SEQ ID No: 86 | VL 064, CDR1 | RASQGISSWLA |
| SEQ ID No: 87 | VL 064, CDR2 | AASSLQS |
| SEQ ID No: 88 | VL 064, CDR3 | QQANGFPIT |
| SEQ ID No: 89 | VH 068 | QLQLQESGSGLVKPSQTLSLTCAVSGGSISSGGYSWSWIRQPPGKGLEWIGX1IYHSGSTYYNPSLKSRVTISVDRSKNQFSLKLSSVTAADTAVYYCARSSYDILTDWGQGTLVTVSS, wherein X1 is any amino acid, preferably C, S, Y or A |
| SEQ ID No: 90 | VH 068, CDR1 | SGGYSWS |
| SEQ ID No: 91 | VH 068, CDR2 | X1IYHSGSTYYNPSLKS, wherein X1 is any amino acid, preferably C, S, Y or A |

TABLE 1-continued

Heavy chain variable region (VH), light chain variable region (VL) and CDR sequences of HuMabs

| SEQ ID No: 92 | VH 068, CDR3 | SSYDILTD |
|---|---|---|
| SEQ ID No: 93 | VL 068 | DIQMTQSPSSVSASVGDRVTITCRASQGISSWLAWY QHKPGKAPKLLIYAASSLQSGVPSRFSGSGSGTDFTL TISSLQPEDFATYYCQQANSFPITFGQGTRLEIK |
| SEQ ID No: 94 | VL 068, CDR1 | RASQGISSWLA |
| SEQ ID No: 95 | VL 068, CDR2 | AASSLQS |
| SEQ ID No: 96 | VL 068, CDR3 | QQANSFPIT |
| SEQ ID No: 97 | VH 069 | QVQLVQSGAEVKKPGASVKVSCETSGYTFTSYGISW VRQAPGHGLEWMGWISAYNGYTNYAQKLQGRVTMT TDTSTSTAYMELRSLRSDDTAVYYCARDLRGTNYFDY WGQGTLVTVSS |
| SEQ ID No: 98 | VH 069, CDR1 | SYGIS |
| SEQ ID No: 99 | VH 069, CDR2 | WISAYNGYTNYAQKLQG |
| SEQ ID No: 100 | VH 069, CDR3 | DLRGTNYFDY |
| SEQ ID No: 101 | VL 069 | DIQMTQSPSSVSASVGDRVTITCRASQGISNWLAWF QHKPGKAPKLLIYAASSLLSGVPSRFSGSGSGTDFTL TISSLQPEDFATYYCQQANSFPITFGQGTRLEIK |
| SEQ ID No: 102 | VL 069, CDR1 | RASQGISNWLA |
| SEQ ID No: 103 | VL 069, CDR2 | AASSLLS |
| SEQ ID No: 104 | VL 069, CDR3 | QQANSFPIT |
| SEQ ID No: 105 | VH 096 | EVQLVQSGAEVKKPGESLKISCKGSGYSFTSYWIGW VRQMPGKGLEWMGIIYPGDSDTRYSPSFQGQVTISA DKSISTAYLQWSSLKASDTAMYYCARQEITGDFDYW GQGTLVTVSS |
| SEQ ID No: 106 | VH 096, CDR1 | SYWIG |
| SEQ ID No: 107 | VH 096, CDR2 | IIYPGDSDTRYSPSFQG |
| SEQ ID No: 108 | VH 096, CDR3 | QEITGDFDY |
| SEQ ID No: 109 | VL 096 | AIQLTQSPSSLSASVGDRVTITCRASQGISSALAWYQ QKPGKAPNLLIYAASSLESGVPSRFSGSGSGTDFTLTI SSLQPEDFATYYCQQFNSYPLTFGGGTKVEIK |
| SEQ ID No: 110 | VL 096, CDR1 | RASQGISSALA |
| SEQ ID No: 111 | VL 096, CDR2 | AASSLES |
| SEQ ID No: 112 | VL 096, CDR3 | QQFNSYPLT |
| SEQ ID No: 113 | VH 098 | QVQLVQSGAEVKKPGASVKVSCKASGYTFTNFGISW VRQAPGQGLEWMGWISAFNGHTDYSQKVQGRVTM TTDTSTSTAYMELRSLRSDDTAVFYCARSHYYGSGSP FDYWGQGTLVTVSS |
| SEQ ID No: 114 | VH 098, CDR1 | NFGIS |
| SEQ ID No: 115 | VH 098, CDR2 | WISAFNGHTDYSQKVQG |
| SEQ ID No: 116 | VH 098, CDR3 | SHYYGSGSPFDY |
| SEQ ID No: 117 | VL 098 | DIQMTQSPSSLSASVGDRVTITCRASQGISNWLAWY QQKPEKAPKSLIYAASSLQSGVPSRFSGSGSGTDFTL TISSLQPEDFATYYCHQYKSYPWTFGQGTKVEIK |
| SEQ ID No: 118 | VL 098, CDR1 | RASQGISNWLA |
| SEQ ID No: 119 | VL 098, CDR2 | AASSLQS |
| SEQ ID No: 120 | VL 098, CDR3 | HQYKSYPWT |
| SEQ ID No: 121 | VH 101 | QVQLVQSGGEVKKPGASVKVSCKASGYTFTRHGITW VRQAPGQGLEWMGWISADNGNTNYAQKFQDRVTM |

TABLE 1-continued

Heavy chain variable region (VH), light chain variable region (VL) and CDR sequences of HuMabs

| | |
|---|---|
| | TTDTSTSTAYMELRSLRSDDTAVYFCARVFRYFDWLL PYFDYWGQGTLVTVST |
| SEQ ID No: 122 VH 101, CDR1 | RHGIT |
| SEQ ID No: 123 VH 101, CDR2 | WISADNGNTNYAQKFQD |
| SEQ ID No: 124 VH 101, CDR3 | VFRYFDWLLPYFDY |
| SEQ ID No: 125 VL 101 | EIVLTQSPGTLSLSPGERATLSCRASQSVSSSYLAWY QQKPGQAPRLLIYGVFSRATGIPDRFSGSGSGTDFTL TISRLEPEDFAVYYCQQYGSSPYTFGQGTKLEIK |
| SEQ ID No: 126 VL 101, CDR1 | RASQSVSSSYLA |
| SEQ ID No: 127 VL 101, CDR2 | GVFSRAT |
| SEQ ID No: 128 VL 101, CDR3 | QQYGSSPYT |
| SEQ ID No: 129 VH 181 | QVQLVQSGAEVKKPGASVKVSCKASGYTFTSYGISW VRQAPGQGLEWMGWISTYNGYTNYAQKLQGRVTMT TDTSTSTAYMELRSLRSDDTAVYYCARDLRGTAYFDY WGQGTLVTVSS |
| SEQ ID No: 130 VH 181, CDR1 | SYGIS |
| SEQ ID No: 131 VH 181, CDR2 | WISTYNGYTNYAQKLQG |
| SEQ ID No: 132 VH 181, CDR3 | DLRGTAYFDY |
| SEQ ID No: 133 VL 181 | DIQMTQSPSSVSASVGDRVTITCRASQGISNWLAWY QHKPGKAPKLLIYAASSLLSGVPSRFSGSGSGTDFTL TISSLQPEDFATYYCQQANSFPITFGQGTRLEIK |
| SEQ ID No: 134 VL 181, CDR1 | RASQGISNWLA |
| SEQ ID No: 135 VL 181, CDR2 | AASSLLS |
| SEQ ID No: 136 VL 181, CDR3 | QQANSFPIT |
| SEQ ID No: 137 VH 066 | QVQLVQSGAEVKKPGASVKVSCEASGYTFTSYGISW VRQAPGHGLEWMGWISAYNGYTNYAQKLQGRVTMT ADTSTSTAYMELRSLRSDDTAVYYCARDLRGTNYFDY WGQGTLVTVSS |
| SEQ ID No: 138 VL 066 | DIQMTQSPSSVSASVGDRVTITCRASQGISNWLAWY QHKPGKAPKLLIYAASSLLSGVPSRFSGSGSGTDFTL TISSLQPEDFATYYCQQANSFPITFGQGTRLEIK |
| SEQ ID No: 139 VH 065 | QVQLVQSGAEVKKPGASVKVSCEASGYTFTNYGISW VRQAPGHGLEWMGWISAYNGYTNYAQKLQGRVTMT TDTSTTTAYMELRSLRSDDTAVYYCARDLRGTNYFDY WGQGTLVTVSS |
| SEQ ID No: 140 VL 065 | DIQMTQSPSSVSASVGDRVTITCRASQGISNWLAWY QHKPGKAPKLLIYAASSLLSGVPSRFSGSGSGTDFTL TISSLQPEDFATYYCQQANSFPITFGQGTRLEIK |
| SEQ ID No: 141 VH 082 | QVQLVQSGAEVKKPGASVKVSCETSGYTFTSYGISW VRQAPGHGLEWMGWISAYNGYTNYAQKLQGRVTMT TDTSTSTAYMELRSLRSDDTAVYYCARDLRGTNYFDY WGQGTLVTVSS |
| SEQ ID No: 142 VL 082 | DIQMTQSPSSVSASVGDRVTITCRASQGISNWLAWY QHKPGKAPKLLIYAASSLLSGVPSRFSGSGSGTDGTL TISSLQPEDFATYYCQQANSFPITFGQGTRLEIK |
| SEQ ID No: 143 VH 089 | QVQLVQSGAEVKKPGASVKVSCETSGYTFTSYGISW VRQAPGHGLEWMGWISAYNGTNYAQKLQGRVTMT TDTSTSTAYMELRSLRSDDTAVYYCARDLRGTNYFDY WGQGTLVTVSS |
| SEQ ID No: 144 VL 089 | DIQMTQSPSSVSASVGDRVTITCRASQGISNWLAWF QHKPGKAPKLLIYAASSLLSGVPSRFSGSGSGTDFTL TISSLQPEDFATYYCQQANSGPITFGQGTRLEIK |

TABLE 1-continued

Heavy chain variable region (VH), light chain variable region (VL) and CDR sequences of HuMabs

| | | |
|---|---|---|
| SEQ ID No: 145 | VH 031 | QVQLVQSGAEVKKPGSSVKVSCKASGGTFSSYGFG WVRQAPGQGLEWMGRISPILGITNYAQMFQGRVTIT ADKSTSTAYMELSSLRSEDTAVYYCARDVGYDQPDT FDIWGQGTMVIVSS |
| SEQ ID No: 146 | VL 031 | DIQMTQSPSSLSASVGDRVTITCRASQGISSWLAWY QQKPEKAPKSLIYAASSLQSGVPSRFSGGGSGTDFTL TISSLQPEDFATYYCQQYNSFPPPTFGQGTKVEIK |
| SEQ ID No: 147 | VH 007 | QVQLVQSGAEVKKPGSSVKVSCKASGGTFSSYGIG WVRQAPGQGLEWMGRIFPILGTANYAQMFQGRVTIT ADKSTSTAYIELTSLRSEDTAVYYCARDVGYDSADAF DIWGQGTMVTVSS |
| SEQ ID No: 148 | VL 007 | DIQMTQSPSSLSASVGDRVTITCRASQGISSWLAWY QQKPEKAPKSLIYAASSLQSGVPSRFSGSGSGTDFTL TISSLQPEDFATYYCQQYNSYPPTFGQGTKVEIK |
| SEQ ID No: 149 | VH 011 | QVQLVQSGAEVKKPGSSVKVSCKASGGTFSSYGIG WVRQAPGQGLEWMGRVFPILGTANYAQMFQGRVTI TADKSTSTAYMELTSLRSEDTAVYYCARDVGYDSAD AFDIQGQGTMVTVSS |
| SEQ ID No: 150 | VL 011 | DIQMTQSPSSLSASVGDRVTITCRASQGISSWLAWY QQKPEKAPKSLIYAASSLQSGVPSRFSGSGSGTDFTL TISSLQPEDFATYYCQQYNSYPPTFGQGTKVEIK |
| SEQ ID No: 151 | VH 017 | QVQLVESGGGVVQPGRSLRLSCAASGFTFSSYAMH WVRQAPGKGLEWVAFISYDGSNKYFADSVKGRFTIS RDNSKNTLYLQMNSLRAEDTAVYYCARELLWFGELW GYFDLWGRGTLVTVSS |
| SEQ ID No: 152 | VL 017 | DIQMTQSPSSVSASVGDRVTITCRASQGISSWLAWY QHKPGKAPKLLIYAASSLQSGVPSRFSGSGSGTDFTL TISSLQPEDFATYYCQEANSFTWTFGQGTKVEIK |
| SEQ ID No: 153 | VH 025 | QVQLVESGGGVVQPGRSLRLSCAASGFTFSSYAMH WVRQAPGKGLEWVAFISYDGSSKDYADSVKGRFTIF RDNSKNTLYLQMSSLRAADTAVYYCARELLWFGELW GYFDLWGRGTLVTVSS |
| SEQ ID No: 154 | VL 025 | DIQMTQSPSSVSASVGDRVTITCRASQGISSWLAWY QHKPGKAPKLLIYAASSLQSGVPSRFSGSGSGTDFTL TISSLQPEDFATYYCQQTNSFTWTFGQGTKVEIK |
| SEQ ID No: 155 | VH 040 | EVQLLESGGGLVQPGGSLRLSCAASGFTFSSYAMTW VRQAPGKGLEWVSVISGSGGITYYADSVKGRFTISR DNSKNTLYLQMNSLRAEDTAVYYCARDRGWGSDYW GQGTLVTVSS |
| SEQ ID No: 156 | VL 040 | EIVLTQSPATLSLSPGERATLSCRASQSVSSYLAWYQ QKPGQAPRLLIYDASNRATGIPARFSGSGSGTDFTLTI SSLEPEDFAVYYCQQRSNWPFTFGPGTKVDIK |
| SEQ ID No: 157 | VH 039 | EVQLLESGGGLVQPGGSLRLSCAASGFTFNNYAMSW VRQAPGKGLEWVSAISGSGGITYYADSEKGRFTISRD NSKNTLYLQMNSLRAEDTAVYYCAKDRGWGSDCWG QGTLVTVSS |
| SEQ ID No: 158 | VL 039 | EIVLTQSPATLSLSPGERATLSCRASQSVSSYLAWYQ QKPGQAPRLLIYDASNRATGIPARFSGSGSGTDFTLTI SSLEPEDFAVYYCQQRSNWPFTFGPGTKVDIK |
| SEQ ID No: 159 | VH 078 | QLQLQESGSGLVKPSQTLSLTCAVSGGSISSGGHSW SWIRQPPGKGLEWIGCLYHSGNTYYNPSLKSRVTISV DRSKNQFSLKLSSVTAADTAVYYCARSSYDILTDWG QGILVTVSS |
| SEQ ID No: 160 | VL 078 | DIQMTQSPSSVSASVGDRVTITCRASQGISSWLAWY QHKPGKAPKLLIYAASSLQSGVPSRFSGSGSGTDFTL TISSLQPEDFATYYCQQANSFPITFGQGTRLEIK |
| SEQ ID No: 161 | VH 084 | QLQLQESGSGLVKPSQTLSLTCGVSGGSISSGGHSW SWIRQPPGKGLEWIGCLYHSGNTYYNPSLKSRVTISV DRSKNQFSLKLSSVTAADTAVYYCARSSYDILTDWG QGTLVTVSS |

TABLE 1-continued

Heavy chain variable region (VH), light chain variable region (VL) and CDR sequences of HuMabs

| | |
|---|---|
| SEQ ID No: 162 VL 084 | DIQMTQSPSSVSASVGDRVTITCRASQGISSWLAWY<br>QHKPGKAPKLLIYAASSLQSGVPSRFSGSGSGTDFTL<br>TISSLQPEDFATYYCQQANSFPITFGQGTRLEIK |
| SEQ ID No: 163 VH 063 | QLQLQESGSGLVKPSQTLSLTCAVSGGSISSGGHSW<br>SWIRQPPGKGLEWIGCIYHSGNTYDNPSLKSRVTIAV<br>DRSKNQLSLKLSFVTAADTAVYYCARSSYDILTDWG<br>QGTLVTVSS |
| SEQ ID No: 164 VL 063 | DIQMTQSPSSVSASVGDRVTITCRASQGISSWLAWY<br>QHKPGKAPKLLIYAASSLQSGVPSRFSGSGSGTDFTL<br>TISSLQPEDFATYYCQQANGFPITFGQGTRLEIK |
| SEQ ID No: 165 VH 087 | QLQLQESGSGLVKPSQTLSLTCAVSGGSISSGGHSW<br>SWIRQPPGKGLEWIGCIYHSGNTYDNPSLKSRVTISV<br>DRSKNQFSLKLSSVTAADTAVYYCARSSYDILTDWG<br>QGTLVTVSS |
| SEQ ID No: 166 VL 087 | DIQMTQSPSSVSASVGDRVTITCRASQGISSWLAWY<br>QHKPGKAPKLLIYAASSLQSGVPSRFSGSGSGTDFTL<br>TISSLQPEDFATYYCQQANGFPITFGQGTRLEIK |
| SEQ ID No: 167 VH 016 | EVQLVQSGAEVKKPGESLKISCKGSGYIFTSYWIGW<br>VRQMPGKGLEWMGIIYPGDSDTRYSPSFQGQVTISA<br>DKSISTAYLQWSSLKASDTAMYYCARQEVTGDFDYW<br>GQGTLVTVSS |
| SEQ ID No: 168 VL 016 | AIQLTQSPSSLSASVGDRVTITCRASQGISSALAWYQ<br>QKPGKAPKLLIYDASSLESGVPSRFSGSGSGTDFTLTI<br>SSLQPEDFATYYCQQFNSYPLTFGGGTKVEIK |
| SEQ ID No: 169 VH 028 | EVQLVQSGGEVKKPGESLKISCKGSGYSFTSYWIGW<br>VRQMPGKGLEWMGIIYPGDSDTRYSPSFQGQVTISA<br>DKSISTAYLQWSSLKASDTAMYYCARQEVTGDFDYW<br>GQGTLVTVSS |
| SEQ ID No: 170 VL 028 | AIQLTQSPSSLSASVGDRVTITCRASQGISSALAWYQ<br>QKPGKAPKLLIYDASSLESGVPSRFSGSGSGTDFTLTI<br>SSLQPEDFATYYCQQFNSYPLTFGGGTKVEIK |
| SEQ ID No: 171 VH 012 | EVQLVQSGAEVKKPGESLKISCKGSGYSFTSYWIGW<br>VRQMPGKGLEWMGIIYPGDSDTRYSPSFQGQVTISA<br>DKSISTAYLQWSSLKASDTAMYYCARQEITGEFDYW<br>GQGTLVTVSS |
| SEQ ID No: 172 VL 012 | AIQLTQSPSSLSASVGDRVTITCRASQGISSALAWYQ<br>QKPGKAPKLLIYDASSLESGVPSRFSGSGSGTDFTLTI<br>SSLQPEDFATYYCQQFNSYPRTFGQGTKVEIK |
| SEQ ID No: 173 VH 095 | EVQLVQSGAEVKKPGESLKISCKGSGYSFTSYWIGW<br>VRQMPGKGLEWMGIIYPGDSNTRYSPSFQGQVTISA<br>DKSISTAYLQWSSLKASDTAMYYCARQEITGDFDYW<br>GQGTLVTVSS |
| SEQ ID No: 174 VL 095 | AIQLTQSPSSLSASVGDRVTITCRASQGISSALAWYQ<br>QKPGKAPKLLIYDASSLESGVPSRFSGSGSGTDFTLTI<br>SSLQPEDFATYYCQQFNSYPLTFGGGTKVEIK |
| SEQ ID No: 175 VH 093 | EVQLVQSGAEVKKPGESLKISCKGSGYSFTSYWIGW<br>VRQMPGKGLEWMGIIYPGDSDTRYSPSFQGQVTISA<br>DKSISTAYLQWSSLKASDTAMYYCARQEITGDFDYW<br>GQGTLVTVSS |
| SEQ ID No: 176 VL 093 | AIQLTQSPSSLSASVGDRVTITCRASQGISSALAWYQ<br>QKPGKAPNLLIYAASSLESGVPSRFSGSGSGTDFTLTI<br>SSLQPEDFATYYCQQFNSYPLTFGGGTKVEIK |
| SEQ ID No: 177 VH 104 | EVQLVQSGAEVKKPGESLKISCKGSGYSFISYWIGW<br>VRQMPGKGLEWMGIIYPGDSDTRYSPSFQGQVTISA<br>DKSISTAYLQWSSLKASDTAMYYCARQEITGDFDYW<br>GQGTLVTVSS |
| SEQ ID No: 178 VL 104 | AIQLTQSPSSLSASVGDRVTITCRASQGISSALAWYQ<br>QKPGKAPKLLIYVASSLESGVPSRFSGSGSGTDFTLTI<br>TSLQPEDFATYYCQQFNSYPITFGQGTRLEIK |

TABLE 2

Mouse origin and heavy chain sequence homologies

| Antibody: | mouse number: | mouse strain: | germline VH: |
|---|---|---|---|
| TH1016-005 | 339732 | HCo12B, C1 | IgHV1-69-4 |
| TH1016-006 | 339732 | HCo12B, C1 | IgHV1-69-4 |
| TH1016-008 | 339732 | HCo12B, C1 | IgHV5-51-1 |
| TH1016-022 | 339733 | HCo12B, C1 | IgHV3-30-3*1 |
| TH1016-024 | 339733 | HCo12B, C1 | IgHV3-23-1 |
| TH1016-035-D09 | 339732 | HCo12B, C1 | IgHV5-51-1 |
| TH1016-045 | 339282 | HCo17, C1 | IgHV3-23-1 |
| TH1016-058 | 343191 | HCo12B, C2 | IgHV3-11-3 |
| TH1016-061 | 348072 | HCo20, C2 | IgHV4-30-2*1 |
| TH1016-062 | 348072 | HCo20, C2 | IgHV4-30-2*1 |
| TH1016-064 | 348072 | HCo20, C2 | IgHV4-30-2*1 |
| TH1016-068 | 348072 | HCo20, C2 | IgHV4-30-2*1 |
| TH1016-069 | 348072 | HCo20, C2 | IgHV1-18-1 |
| TH1016-096 | 339732 | HCo12B, C1 | IgHV5-51-1 |
| TH1016-098 | 347330 | HCo20, C2 | IgHV1-18-1 |
| TH1016-101 | 340659 | HCo20, C1 | IgHV1-18-1 |
| TH1016-181 | 348072 | HCo20, C2 | IgHV1-18-1 |

TABLE 3

Mouse origin and light chain sequence homologies

| Antibody: | mouse number: | mouse strain: | germline: |
|---|---|---|---|
| PC1016-005 | 339732 | HCo12B, C1 | IGKV1D-16*01 |
| PC1016-006 | 339732 | HCo12B, C1 | IGKV1D-16*01 |
| PC1016-008 | 339732 | HCo12B, C1 | IGKV1-13*02 |
| PC1016-022 | 339733 | HCo12B, C1 | IGKV1-12*01 |
| PC1016-024 | 339733 | HCo12B, C1 | IGKV1-12*01 |
| P1016-035 | 339732 | HCo12B, C1 | IGKV1-13*02 |
| PC1016-045 | 339282 | HCo17, C1 | IGKV3-11*01 |
| PC1016-058 | 343191 | HCo12B, C2 | IGKV1-13*02 |
| PC1016-061 | 348072 | HCo20, C2 | IGKV1-12*01 |
| PC1016-062 | 348072 | HCo20, C2 | IGKV1-12*01 |
| PC1016-064 | 348072 | HCo20, C2 | IGKV1-12*01 |
| PC1016-068 | 348072 | HCo20, C2 | IGKV1-12*01 |
| PC1016-069 | 348072 | HCo20, C2 | IGKV1-12*01 |
| PC1016-096 | 339732 | HCo12B, C1 | IGKV1-13*02 |
| PC1016-098 | 347330 | HCo20, C2 | IGKV1D-16*01 |
| PC1016-101 | 340659 | HCo20, C1 | IGKV3-20*01 |
| PC1016-181 | 348072 | HCo20, C2 | IGKV1-12*01 |

FIGS. 1 and 2 give an alignment of HuMabs sequences. On the basis of these sequences, consensus sequence can be defined for some of the CDR sequences. These consensus sequences are given in Table 4.

TABLE 4

Consensus sequences

| SEQ ID No | Germline | CDR | Sequence | Notes |
|---|---|---|---|---|
| SEQ ID No: 179 005-006 | IgHV1-69-4 | CDR1 | SX1X2X3X4 | wherein X1 = Y or F, X2 = A or G, X3 = F or I, X4 = S or G. Preferably, wherein X1 = Y or F, X2 = G, X3 = F or I and X4 = G. |
| SEQ ID No: 180 005-006 | IgHV1-69-4 | CDR2 | RX1X2PILGX3X4NYAQX5FQG | wherein X1 = I or V, X2 = I, S or F, X3 = I or T, X4 = A or T, X5 = K or M. Preferably, wherein X1 = I or V, X2 = S or F, X3 = I or T, X4 = A or T and X5 = M. |
| SEQ ID No: 181 005-006 | IgHV1-69-4 | CDR3 | DVGYDX1X2DX3FDI | wherein X1 = W or S, X2 = P or A, X3 = T or A |
| SEQ ID No: 182 008-035 | IgHV5-51-1 | CDR2 | IIYPGDSX1TRYSPSFQG | wherein X1 = D, E or N |
| SEQ ID No: 183 008-035-096 | IgHV5-51-1 | CDR3 | QEX1TGX2FDY | wherein X1 = V or I, X2 = E or D |
| SEQ ID No: 184 022 | IgHV3-30-3*1 | CDR2 | X1ISYDGSX2KX3X4ADSVKG | wherein X1 = V or F, X2 = N or S, X3 = D or Y, X4 = Y or F |
| SEQ ID No: 185 024 | IgHV3-23-1 | CDR2 | AISGSX1GGSTYYX2DSVKG | wherein X1 = S or no aa, X2 = V or A |
| SEQ ID No: 186 045 | IgHV3-23-1 | CDR1 | X1YAMX2 | wherein X1 = S or N, X2 = S or T |
| SEQ ID No: 187 045 | IgHV3-23-1 | CDR2 | X1ISGSGGX2TYYADSX3KG | wherein X1 = A or V, X2 = S or I, X3 = V or E. Preferably, wherein X1 = A or V, X2 = I and X3 = V or E. |
| SEQ ID No: 188 045 | IgHV3-23-1 | CDR3 | DRGWGSDX1 | wherein X1 = Y or C |
| SEQ ID No: 189 058 | IgHV3-11-3 | CDR1 | DYYMX1 | wherein X1 = Y or S |
| SEQ ID No: 190 058 | IgHV3-11-3 | CDR2 | X1ISX2X3X4SYTX5YX6DSVKG | wherein X1 = T or Y, X2 = D or S, X3 = D or S, X4 = G or S, X5 = Y or N, X6 = P or A |
| SEQ ID No: 191 062-064-068 | IgHV4-30-2*1 | CDR1 | SGGX1SWS | wherein X1 = Y or H |

TABLE 4-continued

Consensus sequences

| SEQ ID No: 192 IgHV4-30-2*1 CDR2 X1X2YHSGX3TYX4NPSLKS<br>062-064-068 | wherein X1 = any amino acid,<br>preferably C, Y, S or A, X2 = I or L,<br>X3 = S or N, X4 = Y or D |
|---|---|
| SEQ ID No: 193 IgHV4-30-2*1 CDR3 SSYDX1LTD<br>062-064-068 | wherein X1 = F or I |
| SEQ ID No: 194 IgHV1-18-1 CDR1 X1YGIS<br>069-181 | wherein X1 = S or N |
| SEQ ID No: 195 IgHV1-18-1 CDR2 WISX1YNGX2TNYAQKLQG<br>069-181 | wherein X1 = A or T, X2 = N or Y.<br>Preferably wherein X1 = A or T and<br>X2 = Y |
| SEQ ID No: 196 IgHV1-18-1 CDR3 DLRGTX1YFDY<br>069-181 | wherein X1 = A or N |
| SEQ ID No: 197 IgHV1-18-1 CDR1 X1X2GIS<br>098 | wherein X1 = N or S, X2 = F or Y |
| SEQ ID No: 198 IgHV1-18-1 CDR2 WISAX1NGX2TX3YX4QKX5QG<br>098 | wherein X1 = F or Y, X2 = H or N,<br>X3 = D or N, X4 = S or A, X5 = V or L |
| SEQ ID No: 199 IgHV1-18-1 CDR1 X1X2GIX3<br>101 | wherein X1 = R or S, X2 = H or Y,<br>X3 = T or S |
| SEQ ID No: 200 IgHV1-18-1 CDR2 WISAX1NGNTNYAQKX2QX3<br>101 | wherein X1 = D or Y, X2 = F or L,<br>X3 = D or G |
| SEQ ID No: 201 IgHV1-18-1 CDR3 VX1RYFDWLLX2YFDY<br>101 | wherein X1 = F or L, X2 = P or no aa |
| SEQ ID No: 202 IGKV1D-16*01 CDR3 QQYNSX1PX2T<br>005-006 | wherein X1 = Y or F, X2 = P or W.<br>Preferably, wherein X1 = Y or F and<br>X2 = P |
| SEQ ID No: 203 IGKV1-13*02 CDR2 X1ASSLES<br>008-035 | wherein X1 = D, V or A |
| SEQ ID No: 204 IGKV1-13*02 CDR3 QQFNSYPLX1T<br>008-035 | wherein X1 = R, I, L, W or MY |
| SEQ ID No: 205 IGKV1-12*01 CDR3 QX1X2X3SFX4WT<br>022 | wherein X1 = Q or E, X2 = A or T,<br>X3 = N or S; X4 = P or T |
| SEQ ID No: 206 IGKV1-12*01 CDR3 QQANSFPX1T<br>024 | wherein X1 = I or no aa |
| SEQ ID No: 207 IGKV1-13*02 CDR3 QQFX1SYPX2IT<br>058 | wherein X1 = T or N, X2 = Q or no aa |
| SEQ ID No: 208 IGKV1-12*01 CDR3 QQANX1FPIT<br>062-064-068 | wherein X1 = G or S |
| SEQ ID No: 209 IGKV1-12*01 CDR1 RASQGISX1WLA<br>069-181 | wherein X1 = S or N |
| SEQ ID No: 210 IGKV1-12*01 CDR2 AASSLX1S<br>069-181 | wherein X1 = Q or L |
| SEQ ID No: 211 IGKV1D-16*01 CDR3 X1QYX2SYPWT<br>098 | wherein X1 = H or Q, X2 = K or N |
| SEQ ID No: 212 IGKV3-20*01 CDR2 GX1X2SRAT<br>101 | wherein X1 = V or A, X2 = F or S |

Example 12

Purification of Antibodies

Culture supernatant was filtered over 0.2 µm dead-end filters and loaded on 5 ml MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH$_2$PO$_4$, 140 mM NaCl, pH 7.4 (B.Braun). Alternatively, subsequent to purification the eluate was loaded on a HiPrep Desalting column and the antibody was exchanged into 12.6 mM NaH$_2$PO$_4$, 140 mM NaCl, pH 7.4 (B.Braun) buffer. After dialysis or buffer-exchange samples were sterile filtered over 0.2 µm dead-end filters. Purity was determined by SDS-PAGE and concentration was measured by nephelometry and absorbance at 280 nm. Purified antibodies were stored at 4° C. Mass spectrometry was performed to identify the molecular mass of the antibody heavy and light chains expressed by the hybridomas as described in Example 10.

Example 13

Binding of Anti-c-Met Clones to Tumor Cells Expressing Membrane-Bound c-Met Measured by Means of FACS Analysis The binding of anti-c-Met antibodies and monovalent forms thereof (also termed "UniBody molecules" herein, see Example 5) to A431 cells expressing membrane-bound c-Met (purchased at ATCC, CRL-1555) was tested using flow cytometry (FACS Canto II, BD Biosciences). Qifi analysis (Dako, Glostrup, Denmark) revealed that A431 cells express on average 30,000 copies of c-Met protein per cell. Binding of anti-c-Met antibodies and UniBody molecules was detected using a Phycoerythrin-conjugated goat-anti-human IgG antibody (Jackson). IgG1-5D5 was used as positive control antibody, and HuMab-KLH was used as isotype control antibody. $EC_{50}$ values were determined by means of non-linear regression (sigmoidal dose-response with variable slope) using GraphPad Prism V4.03 software (GraphPad Software, San Diego, Calif., USA).

FIG. 3 shows that all tested anti-c-Met antibodies and UniBody molecules bound to c-Met expressed on A431 cells in a dose-dependent manner. The $EC_{50}$ values for binding varied between 0.28-1.92 nM for IgG and 0.52-13.89 nM for UniBody molecules. Interestingly, antibody IgG1-024 demonstrated high unsaturated binding levels to A431 cells, which was not observed when binding to HT-29 cells (purchased at ATCC, HTB-38™) was tested (data not shown). For antibodies 022, 024, 062, 064, 069, 098, 101 and 181, no or less than 2-fold decreased $EC_{50}$ values were observed between IgG1's and UniBody molecules of identical clones. Also maximum binding levels were unchanged between IgG1's and UniBody molecules. For antibodies 005, 006, 008, 035, 045 and 058, on the other hand, a more than 2-fold decrease in $EC_{50}$ value as well as a decrease in maximum binding level was observed when comparing IgG1 with their UniBody counterpart. This was most likely due to the lower off-rates ($K_d$) of these antibodies (see Example 14).

Example 14

Affinity Ranking Octet Assay

Antibody binding to cMetECDHis was analyzed by means of Bio-Layer Interferometry (BLI) technology on the Octet System (Fortebio, Menlo Park, USA). Anti-human IgG coated biosensors (Fc-specific) were used to capture anti-c-Met antibodies according to the procedure recommended by the manufacturer. cMetECDHis derived from HEK293 cells was loaded on top of the immobilized anti-c-Met antibodies by placing the loaded biosensor into a well containing 10 µg/mL cMetECDHis diluted in 10 times diluted kinetics buffer (Fortebio). The difference in reflection of light ($\Delta\lambda$, nm) of the biosensor surface due to the binding of cMetECDHis was measured in real time during approximately 10 minutes and was used by the Octet software (V4.0, Fortebio) to calculate the association constant ($k_a$ [1/M×s]). Next, the loaded biosensor was placed into a well containing only kinetics buffer (10 times diluted in PBS) to determine the dissociation constant ($k_d$ [1/s]). Kinetics analysis was performed to determine the affinity ($K_D$ [M]) using model 1:1 (langmuir). As a positive control, 0.2 µg/mL 5D5 IgG1 produced in HEK293 cells, was used.

Table 5 shows that all anti-c-Met antibodies bound to cMetECDHis with nanomolar affinities in the range of 0.6-13.9 nM.

TABLE 5

Kinetic constants ($k_a$, $k_d$ and $K_D$) of antibodies for binding to cMetECDHis

| Clone | $k_a$ [1/Ms] | $k_d$ [1/s] | $K_D$ [M] |
|---|---|---|---|
| 5D5 | 2.14E+05 | 1.25E−03 | 5.86E−09 |
| 005 | 3.18E+05 | 2.52E−03 | 7.92E−09 |
| 006 | 4.25E+05 | 4.20E−03 | 9.89E−09 |
| 008 | 3.08E+05 | 1.57E−03 | 5.12E−09 |
| 022 | 2.36E+05 | 2.51E−04 | 1.06E−09 |
| 024 | 1.45E+05 | 2.28E−04 | 1.57E−09 |
| 035 | 2.64E+05 | 3.68E−03 | 1.39E−08 |
| 045 | 7.21E+05 | 2.07E−03 | 2.87E−09 |
| 058 | 4.64E+05 | 1.25E−03 | 2.70E−09 |
| 061 | 2.56E+05 | 1.53E−04 | 5.96E−10 |
| 062 | 2.73E+05 | 3.19E−04 | 1.17E−09 |
| 064 | 2.84E+05 | 3.24E−04 | 1.14E−09 |
| 068 | 3.21E+05 | 1.35E−03 | 4.21E−09 |
| 069 | 2.12E+05 | 2.67E−04 | 1.26E−09 |
| 096 | 1.96E+05 | 5.00E−04 | 2.55E−09 |
| 098 | 1.64E+05 | 2.97E−04 | 1.82E−09 |
| 101 | 1.69E+05 | 2.14E−04 | 1.27E−09 |
| 181 | 2.37E+05 | 5.31E−04 | 2.23E−09 |

Except for 5D5, each sample was measured once

Example 15

Binding of Anti-c-Met Antibodies to Membrane-Bound c-Met Expressed on Rhesus Monkey Epithelial Cells Measured by Means of FACS Analysis To determine cross-reactivity with Rhesus monkey c-Met, the binding of anti-c-Met antibodies to c-Met positive Rhesus monkey epithelial cells (4MBr-5 purchased at ATCC) was tested using flow cytometry (FACS Canto II, BD Biosciences). A Phycoerythrin-conjugated goat-anti-human IgG antibody (Jackson) was used as a secondary conjugate. HuMab-KLH was used as isotype control antibody.

FIG. 4 demonstrates that all tested anti-c-Met antibodies are cross-reactive with Rhesus c-Met. At both tested concentrations (0.5 µg/mL and 10 µg/mL) the anti-c-Met antibodies were able to bind specifically to Rhesus monkey c-Met. For all antibodies, the signal was at least 5 times higher than for isotype control antibody HuMab-KLH. Interestingly, P1016-035 demonstrated much higher top-fluorescence levels (MFI of ~200,000) compared to other c-Met specific antibodies. This difference was not observed on cell lines expressing human c-Met receptor.

Example 16

Blocking of HGF Binding to the Extracellular Domain of c-Met Determined with Enzyme-Linked Immuno Sorbent Assay (ELISA)

An ELISA was performed to analyze if anti-c-Met antibodies could block binding of hepatocyte growth factor (HGF) to the c-Met receptor. Therefore, coated extracellular domain of c-Met was incubated with an unlabeled anti-c-Met antibody and fluorescently labeled HGF. Non-blocking antibodies do not compete with the labeled HGF for c-Met binding, resulting in maximal fluorescent signal. Blocking antibodies compete with labeled HGF for c-Met binding, resulting in a decreased fluorescent signal.

HGF (ProSpec Tany, Rehovot, Israel) was fluorescently labeled by conjugation with Europium$^{3+}$ (PerkinElmer, Turku, Finland). ELISA wells were coated overnight at 4° C. with 0.5 μg/mL recombinant human c-Met extracellular domain (R&D systems, Minneapolis, USA) diluted in PBS. Next, the ELISA wells were washed with PBST (PBS supplemented with 0.05% Tween-20 [Sigma-Aldrich, Zwijndrecht, The Netherlands]) and blocked for one hour at room temperature (RT) with PBST supplemented with 2% (v/v) chicken serum (Gibco, Paisley, Scotland). After washing with PBST, the ELISA wells were incubated for one hour at RT protected from light with a mixture of 50 μL serially diluted anti-c-Met antibody (0.128-10,000 ng/mL in 5-fold dilutions) and 50 μL of 0.44 μg/mL Europium$^{3+}$-conjugated HGF in PBST, Next, unbound Europium$^{3+}$-conjugated HGF was washed away with PBST and bound Europium$^{3+}$-conjugated HGF was incubated for 30 minutes at RT in the dark with Delfia Enhancement Solution (PerkinElmer) to increase the fluorescent signal. Mean fluorescence intensity at 615 nm was measured using the EnVision 2101 Multilabel reader (PerkinElmer) applying the following settings: Lance/Delfia dual mirror, emission filter 615, excitation filter 340 nm, delay time 400 μs, window 400 μs, 100 flashes, 2000 μs per cycle and bidirectional row-by-row reading. To determine IC$_{50}$ values, the binding curves were analyzed with non-linear regression (sigmoidal dose-response with variable slope, top-values constrained to a shared value for all data-sets) using GraphPad Prism V4.03 software (GraphPad Software, San Diego, Calif., USA).

FIG. 5 depicts representative examples of HGF binding inhibition curves of anti-c-Met antibodies for binding to the extracellular domain of recombinant human c-Met. 5D5 was used as positive control antibody. All anti-c-Met antibodies in the experiment shown were able to compete with Europium$^{3+}$-conjugated HGF for binding to recombinant c-Met. IC$_{50}$ values varied between 0.0011-0.0794 μg/mL. Without adding Europium$^{3+}$-conjugated HGF, roughly ~600 relative fluorescent units (RFU) were detected, indicating the signal when maximal inhibition is accomplished. When binding of Europium$^{3+}$-conjugated HGF was not inhibited, approximately 66,000 RFU were detected. Antibodies 005, 006, 058, 101 and the positive control antibody 5D5 were able to inhibit 84.5-92.1% of HGF binding to the c-Met receptor. All other antibodies were able to inhibit at least 55% of HGF binding to c-Met. Since HGF can bind the c-Met receptor at both the SEMA domain and the Ig region, some antibodies may inhibit only one of these interactions. To determine which interaction was inhibited, a cMetSEMAHis-based inhibition of time-resolved fluorescence resonance energy transfer (TR-FRET) assay was performed.

Example 17

Competition of Anti-c-Met Antibodies for Binding to Soluble cMetECDHis Measured with Sandwich-ELISA First, the optimal coating concentrations of the tested anti-c-Met antibodies and the optimal cMetECDHis concentration were determined. Therefore, ELISA wells were coated overnight at 4° C. with anti-c-Met HuMabs serially diluted in PBS (8 μg/mL in 2-fold dilutions). Next, the ELISA wells were washed with PBST (PBS supplemented with 0.05% Tween-20 [Sigma-Aldrich, Zwijndrecht, The Netherlands]) and blocked for one hour at room temperature (RT) with PBSTC (PBST supplemented 2% [v/v] chicken serum [Gibco, Paisley, Scotland]). Subsequently, the ELISA wells were washed with PBST and incubated for one hour at RT with biotinylated cMetECDHis serially diluted in PBSTC (1 μg/mL in 2-fold dilutions). Unbound biotinylated cMetECDHis was washed away with PBST, and bound biotinylated cMetECDHis was incubated for one hour at RT with 0.1 μg/mL Streptavidin-poly-HRP (Sanquin, Amsterdam, The Netherlands) diluted in PBST. After washing, the reaction was visualized through a 15 minutes incubation with 2,2'-azino-bis(3-ethylbenzothiazoline-6-sulfonic acid (ABTS: dilute one ABTS tablet in 50 mL ABTS buffer [Roche Diagnostics, Almere, The Netherlands]) at RT protected from light. The colorization was stopped by adding an equal volume of oxalic acid (Sigma-Aldrich, Zwijndrecht, The Netherlands). Fluorescence at 405 nm was measured on a microtiter plate reader (Biotek Instruments, Winooski, USA). The conditions that resulted in sub-optimal (approx. 80%) binding of each antibody were determined and used for following cross-block experiments.

ELISA wells were coated with anti-c-Met antibody at a sub-optimal dose as described above. After blocking of the ELISA wells, they were incubated with the predetermined concentration of biotinylated cMetECDHis in the presence of an excess of anti-c-Met antibody. The reaction was developed as described above. Residual binding was expressed as a percentage relative to the binding observed in the absence of competitor antibody.

Table 6: When added as competitor, all anti-c-Met antibodies were able to compete for binding with their immobilized counterparts. 022, 058 and 5D5, when added as competitor antibodies, competed with antibodies 005 and 006. However, the reverse reaction revealed only partial competition by antibodies 005 and 006. These differences can be explained by the lower affinities of antibodies 005 and 006 for biotinylated cMetECDHis. Antibody 5D5, when added as competitor antibody, also demonstrated partial competition with antibodies 008 and 045, whereas no or minimal competition was observed in the reverse reaction. In addition, antibodies 024, 062, 064, 068 and 181 when added as competitor antibodies, demonstrated partial competition with antibody 101, whereas the reverse reaction demonstrated complete inhibition of cMetECDHis binding. Values higher than 100% can be explained by avidity effects and the formation of antibody-cMetECDHis complexes containing two non-competing antibodies.

Antibodies 024, 062, 064, 068, 069, 098, 101 and 181 compete with each other for binding to cMetECDHis. Antibodies 005, 006, 022 and 058 were considered to belong to one cross-block group, a group that is characterized by complete competition with 005, 006, 022, 058 and 5D5. However, antibody 5D5 was the only antibody that was also able to compete for binding with antibody 045. Another group of antibodies that compete for binding to cMetECDHis is formed by 008, 035 and G11-HZ.

TABLE 6

Competition of anti-c-Met antibodies for binding to biotinylated cMetECDHis

| Immobilized anti-body | Competing antibody | | | | | | | |
|---|---|---|---|---|---|---|---|---|
| | 005 | 006 | 008 | 022 | 024 | 035 | 045 | 058 |
| 005 | 7.7 ± 1.1 | 18.2 ± 3.6 | 81.9 ± 3.1 | 4.9 ± 1.3 | 113.5 ± 5.0 | 84.9 ± 0.2 | 116.9 ± 7.0 | 3.6 ± 0.1 |
| 006 | 11.3 ± 0.9 | 14.6 ± 0.7 | 58.8 ±2.2 | 4.6 ± 0.3 | 113.3 ± 1.0 | 67.5 ± 4.2 | 114.5 ± 3.5 | 3.6 ± 0.3 |
| 008 | 63.9 ± 3.1 | 47.3 ± 1.2 | 5.4 ± 0.3 | 82.1 ± 3.0 | 103.2 ± 0.4 | 32.9 ± 1.0 | 100.4 ± 3.8 | 40.8 ± 0.8 |
| 022 | 37.9 ± 3.9 | 60.5 ± 4.0 | 94.1 ± 3.5 | 3.8 ± 1.2 | 99.4 ± 4.8 | 92.4 ± 0.4 | 95.7 ± 3.5 | 5.8 ± 0.0 |
| 024 | 98.4 ± 10.4 | 101.4* ± 16.7 | 104.2* ± 12.7 | 100.2* ± 9.0 | 5.4 ± 0.5 | 108.1* ± 5.8 | 98.1* ± 11.9 | 102.8* ± 12.8 |
| 035 | 36.7 ± 1.0 | 33.0 ± 17.6 | 7.2 ± 1.7 | 54.6 ± 6.5 | 121.4 ± 27.8 | 10.6 ± 0.3 | 125.0 ± 16.8 | 18.5 ± 2.5 |
| 045 | 111.4 ± 1.5 | 110.6 ± 3.5 | 98.5 ± 3.1 | 105.3 ± 2.5 | 102.4 ± 5.6 | 105.4 ± 5.5 | 21.3 ± 0.1 | 115.3* ± 6.5 |
| 058 | 31.4 ± 3.6 | 43.6 ± 2.1 | 90.2 ± 2.5 | 6.8 ± 0.3 | 109.0 ± 4.1 | 90.1 ± 5.4 | 111.7 ± 4.9 | 4.0 ± 0.2 |
| 062 | 95.8 ± 5.1 | 95.2 ± 6.8 | 97.4 ± 5.3 | 94.6 ± 4.0 | 7.3 ± 2.9 | 90.6 ± 11.5 | 97.0 ± 3.0 | 94.4 ± 4.3 |
| 064 | 90.4 ± 1.9 | 90.1* ± 1.4 | 94.6* ± 0.5 | 94.2 ± 3.6 | 7.5 ± 2.5 | 83.5 ± 12.2 | 95.0 ± 4.9 | 95.5 ± 0.6 |
| 068 | 101.1 ± 7.6 | 98.5 ± 6.7 | 101.7 ± 5.5 | 99.6 ± 4.0 | 4.7 ± 2.3 | 88.6 ± 12.7 | 100.4 ± 9.0 | 101.5 ± 5.1 |
| 069 | 102.3 ± 11.2 | 100.3 ± 12.3 | 102.1 ± 12.8 | 97.8 ± 12.5 | 6.6 ± 4.1 | 91.7 ± 27.3 | 99.8 ± 14.4 | 100.6 ± 14.1 |
| 098 | 99.6 ± 6.3 | 97.9 ± 6.7 | 99.8 ± 4.2 | 95.8 ± 5.4 | 12.9 ± 4.2 | 89.4 ± 20.6 | 96.7 ± 3.7 | 98.6 ± 2.9 |
| 101 | 91.5 ± 7.2 | 89.7 ± 7.9 | 94.0 ± 6.3 | 90.7 ± 5.3 | 40.5 ± 5.4 | 96.7 ± 1.9 | 94.7 ± 5.1 | 93.1 ± 5.2 |
| 181 | 95.9 ± 7.8 | 93.7 ± 8.4 | 98.7 ± 5.8 | 92.5 ± 7.4 | 4.3 ± 1.9 | 96.0 ± 9.6 | 96.8 ± 6.7 | 98.9 ± 9.8 |
| 5D5 | 42.3 ± 14.7 | 58.8 ± 19.4 | 90.2 ± 9.9 | 12.4 ± 4.7 | 94.2 ± 9.7 | 98.1 | 83.9 ± 13.4 | 6.6 ± 3.2 |
| G11-HZ | 50.5 ± 7.6 | 47.7 ± 2.9 | 33.3 ± 0.2 | 54.3 ± 3.7 | 98.8 ± 5.6 | 32.8 ± 4.0 | 72.0 ± 9.9 | 27.6 ± 4.3 |

| Immobilized anti-body | Competing antibody | | | | | | | | |
|---|---|---|---|---|---|---|---|---|---|
| | 062 | 064 | 068 | 069 | 098 | 101 | 181 | 5D5 | G11-HZ |
| 005 | 117.7 ± 10.7 | 118.2 ± 7.8 | 128.7 ± 9.5 | 124.0 ± 8.0 | 110.4 ± 7.6 | 103.2 ± 5.0 | 131.0 ± 7.7 | 2.9 ± 0.1 | 76.8 ± 4.4 |
| 006 | 118.8 ± 8.4 | 122.2 ± 5.3 | 128.6 ± 6.5 | 124.5 ± 1.0 | 110.6 ± 2.3 | 105.9 ± 4.1 | 123.5 ± 6.1 | 3.1 ± 0.0 | 54.0 ± 35.1 |
| 008 | 100.5 ± 2.5 | 107.1 ± 6.2 | 112.2 ± 5.1 | 104.1 ± 4.4 | 106.6 ± 2.6 | 101.0 ± 2.5 | 111.3 ± 1.3 | 32.4 ± 0.8 | 2.7 ± 0.2 |
| 022 | 99.4 ± 2.0 | 101.9 ± 3.2 | 104.1 ± 3.3 | 99.6 ± 6.0 | 104.8 ± 4.0 | 103.6 ± 5.1 | 107.1 ± 5.2 | 4.2 ± 2.1 | 85.9 ± 8.3 |
| 024 | 2.3 ± 0.6 | 2.3 ± 0.6 | 12.0 ± 5.5 | 2.9 ± 0.5 | 10.4 ± 4.2 | 4.8 ± 1.0 | 7.1 ± 2.8 | 95.5* ± 1.1 | 98.2* ± 1.3 |
| 035 | 119.6 ± 11.2 | 131.7 ± 20.0 | 175.1 ± 30.2 | 150.9 ± 24.9 | 126.2 ± 19.9 | 113.0 ± 4.6 | 159.1 ± 12.9 | 25.5 ± 9.9 | 7.8 ± 3.2 |
| 045 | 103.1 ± 3.5 | 103.7 ± 5.7 | 113.1 ± 1.4 | 97.0 ± 5.2 | 76.4 ± 11.7 | 101.5 ± 5.1 | 99.4 ± 3.8 | 27.8 ± 3.9 | 99.3 ± 5.3 |
| 058 | 109.1 ± 4.6 | 108.8 ± 4.4 | 118.8 ± 4.2 | 112.6 ± 4.0 | 111.8 ± 6.2 | 104.4 ± 0.8 | 121.3 ± 3.1 | 2.8 ± 0.4 | 81.5 ± 8.6 |
| 062 | 2.4 ± 0.5 | 2.2 ± 0.2 | 14.2 ± 1.8 | 2.9 ± 0.1 | 13.2 ± 0.9 | 7.8 ± 1.1 | 9.4 ± 1.6 | 97.7 ± 8.5 | 101.3 ± 0.9 |
| 064 | 2.2 ± 0.6 | 2.0 ± 0.2 | 13.0 ± 0.9 | 2.7 ± 0.2 | 14.7 ± 1.2 | 7.6 ± 0.8 | 10.1 ± 3.0 | 94.9* ± 4.6 | 102.0 ± 10.5 |
| 068 | 2.0 ± 0.3 | 2.0 ± 0.3 | 6.6 ± 0.7 | 2.4 ± 0.4 | 8.2 ± 1.3 | 4.8 ± 0.7 | 5.2 ± 0.6 | 94.8 ± 2.7 | 110.3 ± 6.6 |
| 069 | 2.2 ± 0.4 | 2.3 ± 0.5 | 10.1 ± 2.6 | 2.4 ± 0.7 | 12.5 ± 3.1 | 3.9 ± 0.5 | 6.3 ± 1.0 | 99.4 ± 16.2 | 110.4 ± 13.2 |
| 098 | 8.8 ± 0.6 | 9.3 ± 1.3 | 18.0 ± 2.5 | 3.4 ± 0.6 | 2.6 ± 0.4 | 4.0 ± 0.6 | 12.0 ± 2.1 | 94.9 ± 1.2 | 99.6 ± 1.2 |
| 101 | 36.9 ± 3.3 | 37.4 ± 3.7 | 45.9 ± 4.3 | 9.5 ± 1.2 | 9.7 ± 1.5 | 3.7 ± 2.4 | 41.9 ± 0.8 | 97.2 ± 4.6 | 98.3 ± 2.1 |
| 181 | 2.0 ± 0.2 | 2.1 ± 0.3 | 6.5 ± 1.1 | 2.2 ± 0.3 | 5.1 ± 1.1 | 2.4 ± 0.2 | 3.6 ± 0.2 | 94.2 ± 4.5 | 98.7 ± 6.7 |
| 5D5 | 97.6 ± 8.1 | 97.1 ± 12.7 | 97.8 ± 6.6 | 99.6 ± 3.9 | 97.6 ± 4.9 | 97.9 ± 10.6 | 103.4 ± 4.3 | 4.1 ± 1.5 | 97.3 |
| G11-HZ | 95.3 ± 3.1 | 99.2 ± 0.6 | 102.6 ± 1.3 | 95.0 ± 8.4 | 96.2 ± 11.8 | 90.1 ± 6.8 | 101.1 ± 5.2 | 29.1 ± 9.2 | 2.6 ± 0.4 |

75->100% competition
25-74% competition
0-24% competition

Data shown are percentages inhibition of binding±the stdev. of 3 independent experiments. For antibodies 035, 5D5 and G11-HZ the cross-block ELISA was performed only twice. In addition, a number of competition reactions (*) resulted in Optimal Density values higher than 5.0, which is above the detection limit of the ELISA reader. These results were discarded from the analysis resulting in duplicate measurements.

Example 18

Blocking of HGF Binding to cMetSEMA-567His8 Determined by Means of Time Resolved-Fluorescent Resonance Energy Transfer (TR-FRET)

HGF can bind the c-Met receptor at both the SEMA domain and the IgG-region. However, only HGF bound to the SEMA domain was found to be crucial for receptor activation. Therefore, the interaction of anti-c-Met antibodies with the SEMA domain of the c-Met receptor was studied using TR-FRET technology. In order to perform this homogenous proximity-based assay, hepatocyte growth factor (HGF, ProSpec Tany, Rehovot, Israel) was conjugated with a fluorescent acceptor dye; AlexaFluor-647 (Invitrogen, Breda, The Netherlands). cMetSEMA-567His8 was labeled with a fluorescent donor molecule directed against the histidine tag (Anti-6×his Europium$^{3+}$, PerkinElmer, Turku, Finland). Binding of the AlexaFluor-647-conjugated HGF to the Europium$^{3+}$-labeled cMetSEMA-567His8 enables an energy transfer of the donor molecule (excitation 340 nm) to the acceptor molecule (emission 665 nm). The mean fluorescent intensity at 665 nm was measured on the EnVision 2101 Multilabel reader (PerkinElmer). Competition of unlabeled anti-c-Met antibodies with AlexaFluor-647-conjugated HGF was measured by a decrease in TR-FRET signal at 665 nm, because in the unbound state, the distance between the donor and acceptor fluorophores is too large for energy transfer to occur.

All dilutions were made in 0.5×Lance detection buffer (PerkinElmer) supplemented with 2.67% Stabilizer solution (PerkinElmer) and 0.03% (v/v) Tween-20 (Riedel de Haen, Seelze, Germany). 25 µL of cMetSEMA-567His8 was added to 25 µL AlexaFluor-647 conjugated HGF, 25 µL of anti-6× his Europium$^{3+}$ and 25 µL of unlabeled anti-c-Met antibody to a 96-well opti-white plate (PerkinElmer). A final concentration of 2.93 µg/mL cMetSEMA-567His8, 0.96 µg/mL AlexaFluor-647-conjugated HGF and 0.4 µg/mL anti-6×his Europium$^{3+}$ was obtained. A 4-fold serial dilution of unlabeled anti-c-Met antibody ranging from 0.49-8000 ng/mL was tested. After overnight incubation at 4° C. in the dark, mean fluorescence intensity at 665 nm was measured using the EnVision 2101 Multilabel reader applying the following settings: Lance/Delfia dual mirror, emission filter 615-665 nm, excitation filter 320 nm, delay time 60 µs, window 100 µs, 100 flashes, 2000 µs per cycle and bidirectional row-by-row reading. To determine IC$_{50}$ values, the binding curves were analyzed with non-linear regression (sigmoidal dose-response with variable slope) using GraphPad Prism V4.03 software (GraphPad Software, San Diego, Calif., USA).

FIG. 6 shows HGF binding inhibition curves of the various anti-c-Met antibodies for binding to cMetSEMA_567His8 tested with TR-FRET. Except for antibodies 008, 035 and 096, all antibodies were able to compete with AlexaFluor-647-conjugated HGF for binding to cMetSEMA-567His8. Antibody 022 was able to inhibit ~80% binding of HGF, whereas antibodies 005, 006, 024, 045, 058, 061, 062, 064, 068, 069, 098, 101, 181 and the positive control antibody 5D5 were able to inhibit >90% of HGF binding to cMetSEMA-567His8. IC$_{50}$ values ranging from 0.082-0.623 µg/mL were determined.

TABLE 7

IC$_{50}$ values (µg/mL) and percentage of ligand inhibition of anti-c-Met antibodies for binding to cMetSEMA-567His8 determined with TR-FRET

| mAb | IC$_{50}$ | % inhibition |
|---|---|---|
| 005 | 0.16 | 92 |
| 006 | 0.16 | 92 |
| 008 | ND | 4 |
| 022 | 0.37 | 77 |
| 024 | 0.39 | 95 |
| 035 | ND | 19 |
| 045 | 0.17 | 92 |
| 058 | 0.15 | 99 |
| 061 | 0.49 | 96 |
| 062 | 0.58 | 97 |
| 064 | 0.07 | 97 |
| 068 | 0.26 | 96 |
| 069 | 0.54 | 97 |
| 096 | ND | 16 |
| 098 | 0.55 | 98 |
| 101 | 0.53 | 96 |
| 181 | 0.34 | 93 |
| 5D5 | 0.2 | 95 |

Data shown are mean MFI of three independent experiments.

Example 19

KP4 Viability Assay

C-Met antibodies were tested for their ability to inhibit viability of KP4 cells (Riken BioResource Center Cell Bank, RCB1005). KP4 cells, which express high levels of both c-Met and HGF in an autocrine manner, were seeded in a 96-wells tissue culture plate (Greiner bio-one, Frickenhausen, Germany) (10,000 cells/well) in serum-free medium (1 part HAM's F12K [Cambrex, East Rutherford, N.J.] and 1 part DMEM [Cambrex]). 66.7 nM anti-c-Met antibody dilution was prepared in serum-free medium and added to the cells. After 3 days incubation, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings. The Alamarblue signal of antibody-treated cells was plotted as a percentage signal compared to untreated cells.

FIG. 7 depicts the percentage inhibition of viable KP4 cells after anti-c-Met antibody treatment compared to untreated cells (0%). The boxed clones are antibodies that cross compete with each other as described in Example 17. Interestingly, antibodies 024, 062, 064, 068, 069, 098, 101 and 181, which belong to the same cross-block group, were all able to inhibit KP4 viability (18-46%), both as IgG1 and as UniBody molecule. Also IgG1 molecules of antibodies 008, 061 and 096 were able to inhibit KP4 viability. In contrast, antibody 045 did not inhibit KP4 viability as IgG1 nor as UniBody molecule. For Uni-1016-045-TE this may be due to its low apparent affinity for membrane bound c-Met, as measured by FACS analysis (Example 13). The IgG1 antibodies of clones 005, 006, 022 and 058 did not inhibit KP4 viability significant, while Uni-1016-022-TE, Uni-1016-058-TE and IgG1-1016-058-wtFab did inhibit 57, 38 and 44% of KP4 viability, respectively. Uni-1016-005 and Uni-1016-006 also cross compete with clones 022 and 058 but did not inhibit KP4 viability significant. This may be due to their low apparent affinities as measured by FACS analysis (Example 13). Interestingly also IgG4-1016-058 demonstrated some inhibition of KP4 viability. This was not observed with IgG4-5D5).

Overall the data indicates that for some cross-blocking groups, monovalent binding is required to inhibit KP4 viability, whereas for other cross-blocking groups both monovalent and bivalent binding antibodies can inhibit KP4 viability.

Example 20

KP4 Xenograft Tumor Model in SCID Mice

A KP4 xenograft tumor model in SCID mice was performed to determine the efficacy of anti-c-Met HuMabs to inhibit tumor growth in vivo. Seven to eleven week-old female SCID-mice, strain C.B-17/IcrPrkdc-scid/CRL, were purchased from Charles River Laboratories Nederland (Maastricht, the Netherlands) and kept under sterile conditions in filter-top cages with food and water provided ad libitum. Microchips (PLEXX BV, Elst, The Netherlands) were placed for mouse identification. All experiments were approved by the Utrecht University animal ethics committee.

At day 0, 10×106 KP4 cells were inoculated subcutaneously in 200 µl PBS on the right flank. Mice were examined at least twice per week for clinical signs of illness. Tumor size was determined at least once a week. Volumes (mm3) are calculated from caliper (PLEXX) measurements as 0.52× (length)×(width)2, starting on day 16. On day 9, average tumor sizes were measured and mice were divided in 8 groups of 7 mice each. Anti-c-Met antibodies (008, 058, 069 and 098) were injected intraperitoneally. Antibody G11-HZ was used as a positive control antibody, whereas 5D5 and isotype-control antibodies were used as negative control antibodies.

Mice received a loading dose of 400 µg/mouse followed weekly with a maintenance dose of 200 µg/mouse, for the duration of 7 weeks.

Additionally, plasma samples, collected before administration of $1^{st}$, $3^{rd}$ and $5^{th}$ maintenance dose and when mice were terminated, the presence of human IgG was verified using latex beads on the BNII nephelometer (Dade Behring, Atterbury, UK).

FIGS. 8 and 9 show that tumor growth of KP4 cells was inhibited by HuMabs 008, 069, 098 and positive control G11-HZ. The inhibition was compared to treatment with isotype-control antibody. Tumor growth of KP4 cells was delayed but not completely inhibited by control antibody G11-HZ. Clones 069 and 098 showed more potent inhibition compared to clones 008 and G11-HZ. Antibodies 5D5 and 058 did not inhibit tumor growth. This was consistent with in vitro data as described in Example 19. Taken together, these data indicate that for some cross-blocking groups bivalent binding antibodies can inhibit KP4 tumor growth.

Example 21

MKN45 Xenograft Tumor Model

A human gastric adenocarcinoma MKN45 xenograft tumor model in nude mice was used to determine the efficacy of anti-c-Met HuMabs to inhibit tumor growth in vivo.

Human MKN45 gastric adenocarcinoma cells were cultured at 37° C. and 5% $CO_2$ in RPMI-1640 medium containing 100 units/mL penicillin G sodium, 100 µg/mL streptomycin sulfate, 25 µg/mL gentamicin, 20% fetal bovine serum, and 2 mM glutamine. Seven to eight weeks old female nude mice (nu/nu, Harlan) (body weights ranging from 17.0 to 26.4 g at the beginning of the study) were used. The animals were fed ad libitum water and food. The mice were housed under conditions complying with the recommendations of the Guide for Care and Use of Laboratory Animals. The animal care and use program was accredited by AAALAC. At day 0, $1 \times 10e^7$ MKN45 cells were inoculated subcutaneously in 200 µl 50% matrigel in PBS in the flank of each mouse. On day 7, the animals were sorted into five groups (n=10) with an average tumor volume of 80 to 120 mm3 and treatment was started. Anti-c-Met antibodies (008, 058, 069) were injected in the tail vein (iv). Antibody G11-HZ was used as a positive control antibody and an isotype control antibody was used as a negative control antibody. All mice received 40 mg/kg antibody on day 7 and 20 mg/kg antibody on days 14, 21, and 28.

Tumors were measured twice weekly using calipers until an endpoint tumor volume of 700 $mm^3$ or until the end of the study (day 62). FIGS. 10 and 11 show that tumor growth of MKN45 cells was significantly delayed by antibodies 008, 058, 069 and the control antibody G11-HZ compared to treatment with isotype control antibody.

Example 22

Decreasing Residual Agonistic Activity of IgG1 c-Met Antibodies by Reducing Conformational Flexibility The natural ligand of c-Met, HGF, is a functional dimer that induces dimerization of two c-Met molecules. The subsequent intracellular phosphorylation of the intracellular domain of c-Met results in the activation of several signaling pathways which are involved in proliferation, invasion and survival of cells. Most bivalent antibodies raised against c-Met show comparable effects as HGF on cell fate, especially when the binding epitopes of the antibody are located near or in the SEMA domain of c-Met.

To minimize the potential residual agonistic activity of the bivalent IgG1 antibodies, a strategy to reduce the conformational flexibility was employed. In an IgG1 there is a large degree of freedom for the Fab arms to move relative to the Fc domain. The largest conformational changes are the result of the flexibility of the hinge, which allows a wide range of Fab-Fc angles (Ollmann Saphire, E., R. L. Stanfield, M. D. M. Crispin, P. W. H. I. Parren, P. M. Rudd, R. A. Dwek, D. R. Burton and I. A. Wilson. 2002. Contrasting IgG structures reveal extreme asymmetry and flexibility. J. Mol. Biol. 319: 9-18). One way to reduce Fab-arm flexibility in immunoglobulins is to prevent the formation of disulphide bonds between the light and the heavy chain by means of genetic modification. In a natural IgG1 antibody the light chain is connected covalently with the heavy chain via a disulphide bond, connecting the C-terminal cysteine of the light chain to the cysteine at position 220 (C220 EU numbering) in the hinge of the Fc of the heavy chain. By either mutating amino acid C220 to serine or any other natural amino acids, by removing C220 by removing the complete hinge, or by replacing the IgG1 hinge with an IgG3 hinge, a molecule is formed in which the light chains are connected via their C-terminal cysteines, analogous to the situation found in the human isotype IgA2m(1). This results in a reduced flexibility of the Fabs relative to the Fc and consequently reduced cross-linking capacity, as shown in comparative studies with IgA2m(1) and IgG1 formats of an agonistic c-Met antibody (5D5) in a KP4 viability assay (FIG. 12).

Another strategy to reduce the flexibility of an IgG1 molecule is to replace the IgG1 hinge with the IgG2 hinge or IgG2-like hinge. (Dangl et al. EMBO J. 1988; 7:1989-94). This hinge region has two properties distinct from that of IgG1, which are considered to render the molecules less flexible. First, compared to IgG1, hinge the IgG2 hinge is 3 amino acids shorter. Second, the IgG2 hinge contains an additional cysteine, thus three instead of two inter-heavy chain disulphide bridges will be formed. Alternatively, a variant of the IgG1 hinge that resembles the IgG2 hinge can be introduced. This mutant (TH7Δ6-9) (WO2010063746) contains mutation T223C and two deletions (K222 and T225) in order to create a shorter hinge with an additional cysteine.

Example 23

Generation of IgG1 Molecules with Reduced Flexibility (Stiffened IgG1 Molecules)

Cloning and Expression

Mutant IgG1 antibodies were designed and cloned using standard molecular biological techniques. An overview of the sequences of all generated hinge region mutations is shown in Table 8 below.

TABLE 8

Amino acid sequence of the hinge of mutant IgG1 antibodies. Deletions are marked by '-', and mutations are highlighted in grey.

| | | | SEQ ID |
|---|---|---|---|
| IgG1 | WT | EPKSCDKTHTCPPCP | 214 |
| IgG1 | Hinge-IgG2 | ERKCCVE---CPPCP | 215 |
| IgG1 | ΔC220 | EPKS-DKTHTCPPCP | 216 |
| IgG1 | C220S | EPKSSDKTHTCPPCP | 220 |
| IgG1 | TH7Δ6-9 | EPKSCD-CH-CPPCP | 219 |
| Hinge | deleted IgG1 (Uni-IgG1) | --------------- | |
| IgG1 | Hinge-IgG3 | ELKTPLGDTTHTCPRCPEPKSCDTPPPCPRCPEPKSCDTPPPCPRCPEPKSCDTPPCPRCP | 218 |

For the expression of the resulting stiffened IgG1 antibodies in mammalian cells, the HC constant region of IgG1, containing mutations in the hinge region (see above Table 8), was synthesized as a codon optimized construct in mammalian expression vector pcDNA3.3 (Invitrogen). A separate vector was constructed by inserting the codon optimized constant region of the human kappa light chain region in pcDNA3.3. VH and VL regions of clone 069 and control antibody 5D5 were inserted in the HC constant plasmid and Kappa light chain plasmid respectively resulting in vectors for the expression of the (mutated) heavy and light chains of the specific antibodies. Co-transfection of the heavy and light chain vectors of a specific antibody in HEK-293F (Invitrogen) cells, resulted in the transient production of mutant antibodies. Purification of the antibodies was performed using Protein A affinity column chromatography (as described in Example 11).

Biochemicial Characterization
Transient Expression

All mutants were expressed at sufficient levels and did not show aberrant formation of multimers as determined by MS (>99% purity) and SDS-PAGE.

The SDS-PAGE results are shown in FIG. 13. In the C220 mutants (C220S and ΔC220) and the hinge-deleted IgG1 variants (the hinge-deleted IgG1 variants are also named Unibody-IgG1 or Uni-IgG1) light chain pairing, visible as a protein band of around 50 kD in non-reduced SDS-PAGE analysis, was observed. The variant with an IgG3 hinge also showed light chain pairing, while the variant with an IgG2 hinge and the IgG1 TH7Δ6-9 mutant showed normal light-heavy chain pairing.

Example 24 c-Met Binding Properties of the Mutants c-Met binding properties of the mutants were tested in an ELISA. ELISA plate wells were coated overnight at 4° C. with rhHGF R/Fc Chimera (R&D Systems; Cat. 358MT/CF) in PBS (1 µg/mL). Next, the wells were washed with PBST (PBS supplemented with 0.05% Tween-20 [Sigma-Aldrich, Zwijndrecht, The Netherlands]) and blocked for one hour at room temperature (RT) with PBSTC (PBST supplemented 2% [v/v] chicken serum [Gibco, Paisley, Scotland]). Subsequently, the wells were washed with PBST and incubated for one hour at RT with the anti-cMet antibodies and variants serially diluted in PBSTC (10 µg/mL in 4-fold dilutions). Unbound antibody was washed away with PBST, and antibody bound to the coat was detected by incubating for one hour at RT with goat-anti-human IgG F(ab')2-HRPdiluted in PBST (Jackson cat. no. 109-035-097). After washing, the reaction was visualized by a 15 min incubation with 2,2'-azino-bis(3-ethylbenzothiazoline-6-sulfonic acid) (ABTS: dilute one ABTS tablet in 50 mL ABTS buffer [Roche Diagnostics, Almere, The Netherlands]) at RT protected from light. The colorization was stopped by adding an equal volume of oxalic acid (Sigma-Aldrich, Zwijndrecht, The Netherlands). Fluorescence at 405 nm was measured on a microtiter plate reader (Biotek Instruments, Winooski, USA). All mutants bound with comparable apparent affinity (EC50) to c-Met (FIG. 14). Table 10 shows the $EC_{50}$ values of the mutants obtained in this experiment.

TABLE 9

The $EC_{50}$ values as determined by ELISA

| | IgG1-1016-069 | IgG1-1016-069-ΔC220 | IgG1-1016-069-C220S | IgG1-1016-069-Hinge IgG2 | IgG2-1016-069 | IgG1-1016-069 TH7Δ6-9 | Uni-1016-069-TE | IgG1-1016-069 | IgG1-1016-069-Hinge IgG3 | Uni-IgG1-1016-069 |
|---|---|---|---|---|---|---|---|---|---|---|
| EC50 (ng/mL) | 49.5 | 18.87 | 15.56 | 23.03 | 29.61 | 18.81 | 30.08 | 45.43 | 14.18 | 15.39 |

Example 25

Reduced Agonistic Effect of Stiffened IgG1 c-Met Antibodies

Receptor Phosphorylation

To determine the agonistic properties of the stiffened antibodies the effect of the antibodies on cMet phosphorylation was performed. Upon dimerizaton of two adjacent cMet receptors by either the natural ligand HGF or most bivalent antibodies, three tyrosine residues (position 1230, 1234 and 1235) in the intracellular domain of c-Met are cross phosphorylated, which is followed by subsequent phosphorylation of several other amino acids in the intracellular domain and activation of a number of signaling cascades. The dimerization and activation of cMet can therefore be monitored by using antibodies specific for the phosphorylated receptor at these positions, and thus used as a read out for the potential agonism of the anti-c-Met antibodies.

A549 cells, CCL-185 obtained from ATCC, were grown in serum containing DMEM medium until 70% confluency was reached. After trypsinization and washing cells they were plated in a 6 well culture plate at 1*10e6 cells/well in serum containing culture medium. After overnight incubation the cells were treated with either HGF (R&D systems; cat. 294-HG) (50 ng/mL) or the panel of antibodies (30 µg/mL) and incubated for 15 minutes at 37° C. The cells were then washed twice with ice cold PBS and lysed with lysis buffer (Cell Signaling; cat. 9803) supplemented with a protease inhibitor cocktail (Roche; cat. 11836170001) and samples were stored at −80° C. Receptor activation was determined by measuring the phosphorylation by means of Western blot using phospho c-Met specific antibodies. The proteins in the cell lysate were separated on a 4-12% SDS-PAGE gel and transferred to nitrocellulose membrane that was subsequently stained with antibody specific for phosphorylated c-Met (Y1234/1235) (Cell Signaling, cat: 3129). To control for gel loading, antibodies against total c-Met and beta-actin were used. Results of the Western blots are shown in FIG. 15.

Tissue culture medium controls and cells treated with the monovalent format UniBody of antibody 5D5 did not show phosphorylation of the receptor. In contrast, Western blot analysis of cells treated with the positive control HGF or agonist antibody IgG1-1016-058 showed a clear band at the expected heigth. Antibody IgG1-1016-069 showed low, but detectable receptor phosphorylation indicating that some cross linking of the receptor takes place. However, variants that were designed to reduce the flexibility of the antibody molecule showed minimal receptor activation, down to a level comparable to the levels detected in cells treated with the monovalent control Uni-5D5-TE. (FIG. 15).

Effect of c-Met Antibodies on NCI-H441 Proliferation In Vitro

The potential proliferative agonistic activity of cMet antibodies was tested using the lung adenocarcinoma cell line NCI-H441 (ATCC, HTB-174™), which expresses high levels of c-Met, but does not produce its ligand HGF. NCI-H441 cells were seeded in a 96-wells tissue culture plate (Greiner bio-one, Frickenhausen, Germany) (5,000 cells/well) in RPMI (Lonza) without serum. Anti c-Met antibody dilutions (66.7 nM) were prepared in RPMI without serum and added to the cells. After 7 days incubation at 37° C./5% $CO_2$, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings.

As appears from FIG. 17 proliferation of NCI-H441 cells was strongly induced by agonistic control mAbs IgG1-058 and IgG1-5D5. Antibody IgG1-1016-069 also showed some agonistic effect compared to cells treated with the istoype control. The agonistic activity of IgG1-1016-069 could be completely removed by introducing the C220 mutants C220S and -del, and partially by the variants with the IgG2 and TH746-9 hinge or IgG2 backbone. Control samples treated with isotype control and the monovalent version of 5D5 (Uni-5D5-TE) did not induce growth of the cells.

KP4 Viability Assay

The ability to inhibit HGF dependent cells was also determined for the anti-c-Met antibody mutants in a KP4 viability assay (see Example 19 for experimental procedures). The results are shown in FIG. 17. The efficacy of IgG1-1016-069 based mutants was completely retained or slightly better in the C220 mutants. Remarkably, mutating C220 in the agonistic antibody 5D5 resulted in a marked reduction of KP4 viability. No agonistic effect of the 058 and 5D5 antibodies in IgG1 format were observed due to the high expression of HGF by KP4 (autocrine HGF loop).

Down-Modulation

Down-modulation of c-Met induced by antagonistic antibodies represents a mechanism of action of therapeutic c-Met antibodies. Accordingly, in one embodiment antibodies with reduced agonistic properties, but with retained ability to induce down-modulation of c-Met are desirable. To determine the down-modulating potential of the antibodies, A549 cells (CCL-185 obtained from ATCC) were seeded in 6-well tissue culture plates (500,000 cells/well) in serum containing cell culture medium and cultured overnight at 37° C. The next morning, anti-c-Met antibodies were added at a final concentration of 10 µg/mL and the plate was incubated another 2 days at 37° C. After washing with PBS, cells were lysed by incubating 30 min at room temperature with 250 µL Lysis buffer (Cell signaling, Danvers, USA). Total protein levels were quantified using bicinchoninic acid (BCA) protein assay reagent (Pierce) following the manufacturer's protocol. c-Met protein levels in cell lysates were quantified using a c-Met-specific sandwich ELISA. To this end, wells of ELISA plates were coated overnight at 4° C. with goat-anti-human c-Met antibody directed against the extracellular domain of c-Met (R&D systems), diluted in PBS (1 µg/mL). Next, the wells were washed with PBST (PBS supplemented with 0.05% Tween-20 [Sigma-Aldrich, Zwijndrecht, The Netherlands]) and blocked for one hour at RT with PBSTC (PBST supplemented 2% [v/v] chicken serum [Gibco, Paisley, Scotland]). Undiluted cell lysates were added (100 µL) and incubated one hour at RT. After washing with PBST, the wells were incubated one hour at RT with a mouse-antibody directed against the intracellular Tyrosine-1234 residue of human-c-Met (Cell signaling), diluted 1:1000 in PBSC. The wells were washed again with PBST and incubated one hour at RT with a goat-anti-mouse Fc-HRP antibody (Jackson) diluted 1:5000 in PBSC. Following washing with PBST, the reaction was visualized through a 30 minutes incubation with 2,2'-azino-bis(3-ethylbenzothiazoline-6-sulfonic acid) (ABTS: dilute one ABTS tablet in 50 mL ABTS buffer [Roche Diagnostics, Almere, The Netherlands]) at RT protected from light. The colorization was stopped by adding an equal volume of oxalic acid (Sigma-Aldrich, Zwijndrecht, The Netherlands). Fluorescence at 405 nm was measured on a microtiter plate reader (Biotek Instruments, Winooski, USA). As appears from FIG. 18 all mutants of antibody 069 were able to induce down-modulation.

Example 26

Antibody-Dependent Cell-Mediated Cytotoxicity (ADCC)

MKN45 cells (purchased from RIKEN BioResource Center, Tsukuba, Japan, RCB1001) were harvested (5×10⁶ cells), washed (twice in PBS, 1500 rpm, 5 min) and collected in 1 mL RPMI 1640 medium supplemented with 10% cosmic calf serum (CCS) (HyClone, Logan, Utah, USA), to which 200 µCi $^{51}$Cr (Chromium-51; Amersham Biosciences Europe GmbH, Roosendaal, The Netherlands) was added. The mixture was incubated in a shaking water bath for 1.5 hours at 37° C. After washing of the cells (twice in PBS, 1500 rpm, 5 min), the cells were resuspended in RPMI 1640 medium supplemented with 10% CCS, counted by trypan blue exclusion and diluted to a concentration of 1×10^5 cells/mL.

Meanwhile, peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France). After resuspension of cells in RPMI 1640 medium supplemented with 10% CCS, cells were counted by trypan blue exclusion and concentrated to 1×10^7 cells/mL.

For each ADCC experiment, 50 µL $^{51}$Cr-labeled MKN45 cells (5,000 cells) were pre-incubated with 15 µg/mL cMet antibody in a total volume of 100 µL RPMI medium supplemented with 10% CCS in a 96-well microtiter plate. After 15 min at RT, 50 µL PBMCs (500,000 cells) were added, resulting in an effector to target cell ratio of 100:1. The maximum amount of cell lysis was determined by incubating 50 µL $^{51}$Cr-labeled MKN45 cells (5,000 cells) with 100 µL 5% Triton-X100. The amount of spontaneous lysis was determined by incubating 5,000 $^{51}$Cr-labeled MKN45 cells in 150 µL medium, without antibody or effector cells. The level of antibody-independent cell lysis was determined by incubating 5,000 MKN45 cells with 500,000 PBMCs without antibody. Subsequently, the cells were incubated 4 hours at 37° C., 5% $CO_2$. The cells were centrifuged (1200 rpm, 3 min) and 75 µL of supernatant was transferred to micronic tubes, after which the released $^{51}$Cr was counted using a gamma counter. The measured counts per minute (cpm) were used to calculate the percentage of antibody-mediated lysis as follows:

(cpm sample−cpm Ab-independent lysis)/(cpm max. lysis−cpm spontaneous lysis)×100%

Various publications have demonstrated the correlation between reduced core-fucosylation and enhanced ADCC activity in vitro (Shields R L. 2002 JBC; 277:26733-26740, Shinkawa T. 2003 JBC; 278(5):3466-3473). FIG. 19 demonstrates that antibody 069 does not induce lysis of MKN45 cells through ADCC. However when core-fucosylation was reduced due to the presence of kifunensine during mAb production in HEK-cells, antibody 069 was able to induce over 30% lysis of MKN45 cells. Moreover, lysis was already observed at antibody concentrations below 0.01 ug/mL. Values depicted are the mean maximum percentages $^{51}$Cr-release±the stdev from one representative in vitro ADCC experiment with MKN45 cells. 069 low-fucose was produced in HEK 293 cells in presence of kifunensine, resulting in an ~99.5% non-core fucosylation (i.e. absence of fucose). 069 high-fucose was produced in HEK 293 cells without kifunensin, resulting in ~2.11% non-core fucosylation, as determined with high performance anion-exchange chromatography coupled with pulsed amperometric detection (HPAEC-PAD) (data not shown).

Example 27

Lack of Binding of c-Met Antibodies to Human Peripheral Blood Cells

In order to address binding of clone 069 to three types of cells (B-cells, monocytes and granulocytes) present in peripheral blood a FACS binding assay was performed. Fluorescently labeled clone 069 was used to enable direct measurement on FACS without use of secondary detection antibodies. The cell populations in the blood were identified in the assay using fluorescently commercial antibodies against specific markers on the cells of interest.

Perhipheral blood from healthy volunteers (University Medical Center Utrecht) was diluted ten times in FACS buffer (PBS+0.4% BSA+0.02% $NaN_3$) and incubated with Alexa[488]-conjugated c-Met antibodies and FITC-conjugated anti-CD19, -CD16 and -CD14 antibodies (final concentration 10 µg/mL) and phycoerythrin (PE)-labeled anti-CD19, -CD16 and -CD14 antibodies (BD Biosciences, San Jose Calif.) to identify cell populations (resp. B cells, granulocytes and monocytes) in a final volume of 100 µl. After 30 minutes at 4° C., samples were centrifuged (300 g, 3 min), supernatant was removed, erythrocytes were lysed by incubation (10 min, 4° C.) with 200 µl Ery-lysis solution (155 mM $NH_4Cl$, 10 mM $KHCO_3$, 0.1 Mm EDTA [pH 7.4]), and samples were washed twice in FACS buffer. Samples were resuspended in 100 µL FACS buffer and analyzed using a FACS Canto II (BD Biosciences).

FIG. 20 is a representative FACS plot which demonstrates that Alexa[488]-conjugated-069 did not bind the B cell population (CD19-PE+ cells within the lymphocyte gate). Binding of Alexa[488]-conjugated-rituximab was used as positive control. Binding to other cell populations was analyzed similarly and representative results for 1 of 3 donors are also plotted in FIG. 21. Antibody 069-Alexa[488] did not bind to B cells, monocytes or granulocytes, whereas the positive control antibodies did demonstrate specific binding.

The invention claimed is:

1. An isolated human monoclonal antibody which binds human c-Met and comprises:
   (i) a VH region comprising the CDR1, 2 and 3 sequences of SEQ ID NO: 34, 185 and 36 and a VL region comprising the CDR1, 2 and 3 sequences of SEQ ID NO: 38, 39 and 206,
   (ii) a VH region comprising the CDR1, 2 and 3 sequences of SEQ ID NO: 191, 192 and 193 and a VL region comprising the CDR1, 2 and 3 sequences of SEQ ID NO: 78, 79 and 208,
   (iii) a VH region comprising the CDR1, 2 and 3 sequences of SEQ ID NO: 194, 195 and 196 and a VL region comprising the CDR1, 2 and 3 sequences of SEQ ID NO: 209, 210 and 104;
   (iv) a VH region comprising the CDR1, 2 and 3 sequences of SEQ ID NO: 197, 198 and 116 and a VL region comprising the CDR1, 2 and 3 sequences of SEQ ID NO: 118, 119 and 211, or
   (v) a VH region comprising the CDR1, 2 and 3 sequences of SEQ ID NO: 199, 200 and 201 and a VL region comprising the CDR1, 2 and 3 sequences of SEQ ID NO: 126, 212 and 128.

2. An isolated human monoclonal antibody which binds human c-Met and comprises a heavy and light chain variable region, wherein:
   (a) the VH region comprises the sequence of SEQ ID NO: 33 and the VL region comprises the sequence of SEQ ID NO: 37,
   (b) the VH region comprises the sequence of SEQ ID NO: 65 and a VL region comprising the sequence of SEQ ID NO: 69,
   (c) the VH region comprises the sequence of SEQ ID NO: 73 and the VL region comprises the sequence of SEQ ID NO: 77,
   (d) the VH region comprises the sequence of SEQ ID NO:81 and the VL region comprises the sequence of SEQ ID NO: 85,
   (e) the VH region comprises the sequence of SEQ ID NO:89 and the VL region comprises the sequence of SEQ ID NO: 93,
   (f) the VH region comprises the sequence of SEQ ID NO:97 and the VL region comprises the sequence of SEQ ID NO: 101,
   (g) the VH region comprises the sequence of SEQ ID NO: 113 and the VL region comprises the sequence of SEQ ID NO: 117,
   (h) the VH region comprises the sequence of SEQ ID NO: 121 and the VL region comprises the sequence of SEQ ID NO: 125, (i) the VH region comprises the sequence of SEQ ID NO: 129 and the VL region comprises the sequence of SEQ ID NO: 133,
(j) the VH region comprises the sequence of SEQ ID NO: 159 and the VL region comprises the sequence of SEQ ID NO: 160,
(k) the VH region comprises the sequence of SEQ ID NO: 161 and the VL region comprises the sequence of SEQ ID NO: 162,
(l) the VH region comprises the sequence of SEQ ID NO: 163 and the VL region comprises the sequence of SEQ ID NO: 164,
(m) the VH region comprises the sequence of SEQ ID NO: 165 and the VL region comprises the sequence of SEQ ID NO: 166,
(n) the VH region comprises the sequence of SEQ ID NO: 137 and the VL region comprises the sequence of SEQ ID NO: 138,
(o) the VH region comprises the sequence of SEQ ID NO: 139 and the VL region comprises the sequence of SEQ ID NO: 140,
(p) the VH region comprises the sequence of SEQ ID NO: 141 and the VL region comprises the sequence of SEQ ID NO: 142, or
(q) the VH region comprises the sequence of SEQ ID NO: 143 and the VL region comprises the sequence of SEQ ID NO: 144.

3. The antibody of claim 1, wherein the antibody binds to the SEMA domain of c-Met, wherein the antibody inhibits binding of HGF to the SEMA domain with an IC50 less than 10 µg/mL as determined by TR-FRET.

4. The antibody of claim 1, wherein the antibody binds to A431 cells with an EC50 of 10 nM or less, as determined by FACS.

5. The antibody of claim 4, wherein the antibody is a bivalent antibody.

6. The antibody of claim 1, wherein the antibody binds to c-Met with an affinity constant ($K_D$) of 20 nM or less, as determined by bio-layer interferometry.

7. The antibody of claim 1, wherein the antibody binds to Rhesus monkey c-Met, wherein the signal of antibody binding to Rhesus monkey c-Met is at least 5 times that of a negative control antibody, as determined by FACS.

8. The antibody of claim 1, wherein the antibody inhibits binding of HGF to the extracellular domain of c-Met, wherein the antibody inhibits binding more than 40%, as determined by ELISA.

9. The antibody of claim 1, wherein the antibody is capable to inhibit the viability of KP4 cells, wherein the antibody inhibits the viability of KP4 cells by more than 10% after applying 66.7 nM of the antibody to 10,000 KP4 cells for 3 days.

10. The antibody of claim 1, wherein the antibody is a full-length antibody.

11. The antibody of claim 1, wherein the antibody is conjugated to another moiety.

12. The antibody of claim 1, wherein the antibody is an effector-function-deficient antibody.

13. The antibody of claim 1, wherein the antibody is a monovalent antibody.

14. The antibody of claim 13, wherein the monovalent antibody comprises:
(i) a variable region of an antibody of claim 1 or an antigen binding part of the said region, and
(ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region do not comprise any amino acid residues, which are capable of forming disulfide bonds with an identical $C_H$ region or other covalent or stable non-covalent inter-heavy chain bonds with an identical $C_H$ region in the presence of polyclonal human IgG.

15. The antibody of claim 14, wherein the immunoglobulin referred to in step (ii) is of the IgG4 subtype.

16. The antibody of claim 14, wherein the heavy chain has been modified such that the entire hinge has been deleted.

17. The antibody of claim 1, wherein the antibody has been modified to make it less flexible in the hinge region, wherein the hinge region has been modified by:
(i) deleting the hinge region of the sequence EPKSCDKTHTCPPCP (SEQ ID NO: 214) and substituting it with the IgG2 hinge region of the sequence: ERKCCVECPPCP (SEQ ID NO: 215);
(ii) deleting position 220 modified hinge region has the sequence of EPKSDKTHTCPPCP (SEQ ID NO: 216);
(iii) substituting cysteine at position 220 with any other natural amino acid (X) so the modified hinge region has the sequence of EPKSXDKTHTCPPCP (SEQ ID NO: 217);
(iv) deleting the hinge region of sequence EPKSCDKTHTCPPCP (SEQ ID NO: 214) ;
(v) deleting the hinge region of the sequence EPKSCDKTHTCPPCP (SEQ ID NO: 214) and substituting it with the IgG3 hinge region of the sequence ELKTPLGDTTHTCPRCPEPKSCDTPPPCPRCPEPKSCDTPPPCPRCPEPKSCDTPPPCPRCP (SEQ ID NO: 218); or
(vi) substituting threonine at position 223 with cysteine, and deleting lysine at position 222 and threonine at position 225, so the modified hinge region has the sequence of EPKSCDCHCPPCP (SEQ ID NO: 219),
wherein the amino acid positions are based on the EU index as described in Kabat.

18. The antibody of claim 17, wherein the hinge region has been modified by substituting cysteine at position 220 with serine so the modified hinge region has the sequence of EPKSSDKTHTCPPCP (SEQ ID NO: 220).

19. The antibody of claim 17, wherein the antibody is of the IgG2 subtype.

20. The antibody of claim 1, wherein the antibody has been modified to reduce core-fucosylation below 10%, as determined by high performance anion-exchange chromatography coupled with pulsed amperometric detection.

21. The antibody of claim 1, wherein the antibody is a bispecific antibody, comprising a c-Met binding site and a second antigen-binding site having a different binding specificity.

22. A pharmaceutical composition comprising an antibody as defined in claim 1 and a pharmaceutically acceptable carrier.

23. A kit for detecting the presence of c-Met in a sample comprising
an antibody of claim 1; and
instructions for use of the kit.

24. The antibody of claim 1, wherein the antibody comprises:
a) a VH region comprising the CDR1, 2 and 3 sequences of SEQ ID NO: 34, 35 and 36 and a VL region comprising the CDR1, 2 and 3 sequences of SEQ ID NO: 38, 39 and 40, b) (i) a VH region comprising the CDR1, 2 and 3 sequences of SEQ ID NO: 66, 67 and 68 and a VL region comprising the CDR1, 2 and 3 sequences of SEQ ID NO: 70, 71 and 72,
  (ii) a VH region comprising the CDR1, 2 and 3 sequences of SEQ ID NO: 74, 75 and 76 and a VL region comprising the CDR1, 2 and 3 sequences of SEQ ID NO: 78, 79 and 80,
  (iii) a VH region comprising the CDR1, 2 and 3 sequences of SEQ ID NO: 82, 83 and 84 and a VL region comprising the CDR1, 2 and 3 sequences of SEQ ID NO: 86, 87 and 88, or
  (iv) a VH region comprising the CDR1, 2 and 3 sequences of SEQ ID NO: 90, 91 and 92 and a VL region comprising the CDR1, 2 and 3 sequences of SEQ ID NO: 94, 95 and 96,
c) (i) a VH region comprising the CDR1, 2 and 3 sequences of SEQ ID NO: 98, 99 and 100 and a VL region comprising the CDR1, 2 and 3 sequences of SEQ ID NO: 102, 103 and 104, or
  (ii) a VH region comprising the CDR1, 2 and 3 sequences of SEQ ID NO: 130, 131 and 132 and a VL region comprising the CDR1, 2 and 3 sequences of SEQ ID NO: 134, 135 and 136,
d) a VH region comprising the CDR1, 2 and 3 sequences of SEQ ID NO: 114, 115 and 116 and a VL region comprising the CDR1, 2 and 3 sequences of SEQ ID NO: 118, 119 and 120, or
e) a VH region comprising the CDR1, 2 and 3 sequences of SEQ ID NO: 122, 123 and 124 and a VL region comprising the CDR1, 2 and 3 sequences of SEQ ID NO: 126, 127 and 128.

\* \* \* \* \*

UNITED STATES PATENT AND TRADEMARK OFFICE
CERTIFICATE OF CORRECTION

| | | |
|---|---|---|
| PATENT NO. | : 9,068,011 B2 | Page 1 of 1 |
| APPLICATION NO. | : 13/583743 | |
| DATED | : June 30, 2015 | |
| INVENTOR(S) | : Joost J. Neijssen et al. | |

It is certified that error appears in the above-identified patent and that said Letters Patent is hereby corrected as shown below:

On the title page item 73, the Assignee's name reads "GENMAB A+S", but should read --GENMAB A/S--.

In the Claims:

At column 197, Claim 3, line 30, the sentence "binding of HGF to the SEMA domain with an IC50 less than", should read --binding of HGF to the SEMA domain with an IC50 of less than--.

Signed and Sealed this
Twenty-ninth Day of December, 2015

Michelle K. Lee
*Director of the United States Patent and Trademark Office*

SEQUENCE LISTING

```
<160> NUMBER OF SEQ ID NOS: 233

<210> SEQ ID NO 1
<211> LENGTH: 121
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Phe Gly Trp Val Arg Gln Ala Pro Gly Gln Gly Leu Glu Trp Met
        35                  40                  45

Gly Arg Ile Ser Pro Ile Leu Gly Ile Ala Asn Tyr Ala Gln Met Phe
    50                  55                  60
```

```
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Val Gly Tyr Asp Trp Pro Asp Thr Phe Asp Ile Trp Gly
            100                 105                 110

Gln Gly Thr Met Val Ile Val Ser Ser
        115                 120

<210> SEQ ID NO 2
<211> LENGTH: 5
<212> TYPE: PRT
<213> ORGANISM: Homo sapiens

<400> SEQUENCE: 2

Ser Tyr Gly Phe Gly
1               5

<210> SEQ ID NO 3
<211> LENGTH: 17
<212> TYPE: PRT
<213> ORGANISM: Homo sapiens

<400> SEQUENCE: 3

Arg Ile Ser Pro Ile Leu Gly Ile Ala Asn Tyr Ala Gln Met Phe Gln
1               5                   10                  15

Gly

<210> SEQ ID NO 4
<211> LENGTH: 12
<212> TYPE: PRT
<213> ORGANISM: Homo sapiens

<400> SEQUENCE: 4

Asp Val Gly Tyr Asp Trp Pro Asp Thr Phe Asp Ile
1               5                   10

<210> SEQ ID NO 5
<211> LENGTH: 107
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105

<210> SEQ ID NO 6
```

<211> LENGTH: 11
<212> TYPE: PRT
<213> ORGANISM: Homo sapiens

<400> SEQUENCE: 6

Arg Ala Ser Gln Gly Ile Ser Ser Trp Leu Ala
1               5                   10

<210> SEQ ID NO 7
<211> LENGTH: 7
<212> TYPE: PRT
<213> ORGANISM: Homo sapiens

<400> SEQUENCE: 7

Ala Ala Ser Ser Leu Gln Ser
1               5

<210> SEQ ID NO 8
<211> LENGTH: 9
<212> TYPE: PRT
<213> ORGANISM: Homo sapiens

<400> SEQUENCE: 8

Gln Gln Tyr Asn Ser Phe Pro Pro Thr
1               5

<210> SEQ ID NO 9
<211> LENGTH: 121
<212> TYPE: PRT
<213> ORGANISM: Homo sapiens

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Phe
            20                  25                  30

Gly Ile Gly Trp Val Arg Gln Ala Pro Gly Gln Gly Leu Glu Trp Met
        35                  40                  45

Gly Arg Ile Phe Pro Ile Leu Gly Thr Ala Asn Tyr Ala Gln Met Phe
    50                  55                  60

Gln Gly Arg Val Thr Ile Thr Ala Asp Lys Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Arg Asp Val Gly Tyr Asp Ser Ala Asp Ala Phe Asp Ile Trp Gly
            100                 105                 110

Gln Gly Thr Met Val Thr Val Ser Ser
        115                 120

<210> SEQ ID NO 10
<211> LENGTH: 5
<212> TYPE: PRT
<213> ORGANISM: Homo sapiens

<400> SEQUENCE: 10

Ser Phe Gly Ile Gly
1               5

<210> SEQ ID NO 11
<211> LENGTH: 17
<212> TYPE: PRT
<213> ORGANISM: Homo sapiens

```
<400> SEQUENCE: 11

Arg Ile Phe Pro Ile Leu Gly Thr Ala Asn Tyr Ala Gln Met Phe Gln
1               5                   10                  15

Gly

<210> SEQ ID NO 12
<211> LENGTH: 12
<212> TYPE: PRT
<213> ORGANISM: Homo sapiens

<400> SEQUENCE: 12

Asp Val Gly Tyr Asp Ser Ala Asp Ala Phe Asp Ile
1               5                   10

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105

<210> SEQ ID NO 14
<211> LENGTH: 11
<212> TYPE: PRT
<213> ORGANISM: Homo sapiens

<400> SEQUENCE: 14

Arg Ala Ser Gln Gly Ile Ser Ser Trp Leu Ala
1               5                   10

<210> SEQ ID NO 15
<211> LENGTH: 7
<212> TYPE: PRT
<213> ORGANISM: Homo sapiens

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Homo sapiens

<400> SEQUENCE: 16

Gln Gln Tyr Asn Ser Tyr Pro Pro Thr
```

-continued

<210> SEQ ID NO 17
<211> LENGTH: 118
<212> TYPE: PRT
<213> ORGANISM: Homo sapiens

<400> SEQUENCE: 17

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Glu Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Gln Glu Ile Thr Gly Glu Phe Asp Tyr Trp Gly Gln Gly Thr
            100                 105                 110
Leu Val Thr Val Ser Ser
        115

<210> SEQ ID NO 18
<211> LENGTH: 5
<212> TYPE: PRT
<213> ORGANISM: Homo sapiens

<400> SEQUENCE: 18

Ser Tyr Trp Ile Gly
1               5

<210> SEQ ID NO 19
<211> LENGTH: 17
<212> TYPE: PRT
<213> ORGANISM: Homo sapiens

<400> SEQUENCE: 19

Ile Ile Tyr Pro Gly Asp Ser Glu Thr Arg Tyr Ser Pro Ser Phe Gln
1               5                   10                  15
Gly

<210> SEQ ID NO 20
<211> LENGTH: 9
<212> TYPE: PRT
<213> ORGANISM: Homo sapiens

<400> SEQUENCE: 20

Gln Glu Ile Thr Gly Glu Phe Asp Tyr
1               5

<210> SEQ ID NO 21
<211> LENGTH: 107
<212> TYPE: PRT
<213> ORGANISM: Homo sapiens

<400> SEQUENCE: 21

Ala Ile Gln Leu Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 22
<211> LENGTH: 11
<212> TYPE: PRT
<213> ORGANISM: Homo sapiens

<400> SEQUENCE: 22

Arg Ala Ser Gln Gly Ile Ser Ser Ala Leu Ala
1               5                   10

<210> SEQ ID NO 23
<211> LENGTH: 7
<212> TYPE: PRT
<213> ORGANISM: Homo sapiens

<400> SEQUENCE: 23

Asp Ala Ser Ser Leu Glu Ser
1               5

<210> SEQ ID NO 24
<211> LENGTH: 9
<212> TYPE: PRT
<213> ORGANISM: Homo sapiens

<400> SEQUENCE: 24

Gln Gln Phe Asn Ser Tyr Pro Arg Thr
1               5

<210> SEQ ID NO 25
<211> LENGTH: 123
<212> TYPE: PRT
<213> ORGANISM: Homo sapiens

<400> SEQUENCE: 25

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                      55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Leu Trp Phe Gly Glu Leu Trp Gly Tyr Phe Asp Leu
```

```
              100                 105                 110
Trp Gly Arg Gly Thr Leu Val Thr Val Ser Ser
        115                 120

<210> SEQ ID NO 26
<211> LENGTH: 5
<212> TYPE: PRT
<213> ORGANISM: Homo sapiens

<400> SEQUENCE: 26

Ser Tyr Ala Met His
1               5

<210> SEQ ID NO 27
<211> LENGTH: 17
<212> TYPE: PRT
<213> ORGANISM: Homo sapiens

<400> SEQUENCE: 27

Val Ile Ser Tyr Asp Gly Ser Asn Lys Tyr Tyr Ala Asp Ser Val Lys
1               5                   10                  15

Gly

<210> SEQ ID NO 28
<211> LENGTH: 14
<212> TYPE: PRT
<213> ORGANISM: Homo sapiens

<400> SEQUENCE: 28

Glu Leu Leu Trp Phe Gly Glu Leu Trp Gly Tyr Phe Asp Leu
1               5                   10

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Ala Ser Ser Phe Thr Trp
                85                  90                  95

Thr Phe Gly Gln Gly Thr Lys Val Glu Ile Lys
            100                 105

<210> SEQ ID NO 30
<211> LENGTH: 11
<212> TYPE: PRT
<213> ORGANISM: Homo sapiens

<400> SEQUENCE: 30

Arg Ala Ser Gln Gly Ile Ser Ser Trp Leu Ala
1               5                   10
```

```
<210> SEQ ID NO 31
<211> LENGTH: 7
<212> TYPE: PRT
<213> ORGANISM: Homo sapiens

<400> SEQUENCE: 31

Ala Ala Ser Ser Leu Gln Ser
1               5

<210> SEQ ID NO 32
<211> LENGTH: 9
<212> TYPE: PRT
<213> ORGANISM: Homo sapiens

<400> SEQUENCE: 32

Gln Glu Ala Ser Ser Phe Thr Trp Thr
1               5

<210> SEQ ID NO 33
<211> LENGTH: 122
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Ser Gly Gly Ser Thr Tyr Tyr Val Asp Ser
    50                  55                  60

Val Lys Gly Arg Phe Thr Ile Ser Arg Ala Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asp Leu Asp Arg Gly Trp Met Gly Tyr Phe Gly Tyr Trp
            100                 105                 110

Gly Gln Gly Thr Leu Val Thr Val Ser Ser
        115                 120

<210> SEQ ID NO 34
<211> LENGTH: 5
<212> TYPE: PRT
<213> ORGANISM: Homo sapiens

<400> SEQUENCE: 34

Ser Tyr Ala Met Ser
1               5

<210> SEQ ID NO 35
<211> LENGTH: 18
<212> TYPE: PRT
<213> ORGANISM: Homo sapiens

<400> SEQUENCE: 35

Ala Ile Ser Gly Ser Ser Gly Gly Ser Thr Tyr Tyr Val Asp Ser Val
1               5                   10                  15

Lys Gly
```

```
<210> SEQ ID NO 36
<211> LENGTH: 12
<212> TYPE: PRT
<213> ORGANISM: Homo sapiens

<400> SEQUENCE: 36

Asp Leu Asp Arg Gly Trp Met Gly Tyr Phe Gly Tyr
1               5                   10

<210> SEQ ID NO 37
<211> LENGTH: 106
<212> TYPE: PRT
<213> ORGANISM: Homo sapiens

<400> SEQUENCE: 37

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Thr
                85                  90                  95

Phe Gly Gln Gly Thr Arg Leu Glu Ile Lys
            100                 105

<210> SEQ ID NO 38
<211> LENGTH: 11
<212> TYPE: PRT
<213> ORGANISM: Homo sapiens

<400> SEQUENCE: 38

Arg Ala Ser Gln Gly Ile Ser Ser Trp Leu Ala
1               5                   10

<210> SEQ ID NO 39
<211> LENGTH: 7
<212> TYPE: PRT
<213> ORGANISM: Homo sapiens

<400> SEQUENCE: 39

Ala Ala Ser Ser Leu Gln Ser
1               5

<210> SEQ ID NO 40
<211> LENGTH: 8
<212> TYPE: PRT
<213> ORGANISM: Homo sapiens

<400> SEQUENCE: 40

Gln Gln Ala Asn Ser Phe Pro Thr
1               5

<210> SEQ ID NO 41
<211> LENGTH: 118
<212> TYPE: PRT
<213> ORGANISM: Homo sapiens
```

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Gln Glu Ile Thr Gly Glu Phe Asp Tyr Trp Gly Gln Gly Thr
            100                 105                 110

Leu Val Thr Val Ser Ser
        115

<210> SEQ ID NO 42
<211> LENGTH: 5
<212> TYPE: PRT
<213> ORGANISM: Homo sapiens

<400> SEQUENCE: 42

Ser Tyr Trp Ile Gly
1               5

<210> SEQ ID NO 43
<211> LENGTH: 17
<212> TYPE: PRT
<213> ORGANISM: Homo sapiens

<400> SEQUENCE: 43

Ile Ile Tyr Pro Gly Asp Ser Asp Thr Arg Tyr Ser Pro Ser Phe Gln
1               5                   10                  15

Gly

<210> SEQ ID NO 44
<211> LENGTH: 9
<212> TYPE: PRT
<213> ORGANISM: Homo sapiens

<400> SEQUENCE: 44

Gln Glu Ile Thr Gly Glu Phe Asp Tyr
1               5

<210> SEQ ID NO 45
<211> LENGTH: 108
<212> TYPE: PRT
<213> ORGANISM: Homo sapiens

<400> SEQUENCE: 45

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Met
                 85                  90                  95

Tyr Thr Phe Gly Gln Gly Thr Lys Leu Glu Ile Lys
            100                 105
```

<210> SEQ ID NO 46
<211> LENGTH: 11
<212> TYPE: PRT
<213> ORGANISM: Homo sapiens

<400> SEQUENCE: 46

```
Arg Ala Ser Gln Gly Ile Ser Ser Ala Leu Ala
 1               5                  10
```

<210> SEQ ID NO 47
<211> LENGTH: 7
<212> TYPE: PRT
<213> ORGANISM: Homo sapiens

<400> SEQUENCE: 47

```
Asp Ala Ser Ser Leu Glu Ser
 1               5
```

<210> SEQ ID NO 48
<211> LENGTH: 10
<212> TYPE: PRT
<213> ORGANISM: Homo sapiens

<400> SEQUENCE: 48

```
Gln Gln Phe Asn Ser Tyr Pro Met Tyr Thr
 1               5                  10
```

<210> SEQ ID NO 49
<211> LENGTH: 117
<212> TYPE: PRT
<213> ORGANISM: Homo sapiens

<400> SEQUENCE: 49

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Ser Gly Ser Gly Gly Ile Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Trp Gly Ser Asp Tyr Trp Gly Gln Gly Thr Leu
            100                 105                 110

Val Thr Val Ser Ser
            115
```

<210> SEQ ID NO 50
<211> LENGTH: 5

<212> TYPE: PRT
<213> ORGANISM: Homo sapiens

<400> SEQUENCE: 50

Ser Tyr Ala Met Ser
1               5

<210> SEQ ID NO 51
<211> LENGTH: 17
<212> TYPE: PRT
<213> ORGANISM: Homo sapiens

<400> SEQUENCE: 51

Val Ile Ser Gly Ser Gly Gly Ile Thr Tyr Tyr Ala Asp Ser Val Lys
1               5                   10                  15

Gly

<210> SEQ ID NO 52
<211> LENGTH: 8
<212> TYPE: PRT
<213> ORGANISM: Homo sapiens

<400> SEQUENCE: 52

Asp Arg Gly Trp Gly Ser Asp Tyr
1               5

<210> SEQ ID NO 53
<211> LENGTH: 107
<212> TYPE: PRT
<213> ORGANISM: Homo sapiens

<400> SEQUENCE: 53

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Thr Phe Gly Pro Gly Thr Lys Val Asp Ile Lys
            100                 105

<210> SEQ ID NO 54
<211> LENGTH: 11
<212> TYPE: PRT
<213> ORGANISM: Homo sapiens

<400> SEQUENCE: 54

Arg Ala Ser Gln Ser Val Ser Ser Tyr Leu Ala
1               5                   10

<210> SEQ ID NO 55
<211> LENGTH: 7
<212> TYPE: PRT
<213> ORGANISM: Homo sapiens

<400> SEQUENCE: 55

Asp Ala Ser Asn Arg Ala Thr
1               5

<210> SEQ ID NO 56
<211> LENGTH: 9
<212> TYPE: PRT
<213> ORGANISM: Homo sapiens

<400> SEQUENCE: 56

Gln Gln Arg Ser Asn Trp Pro Phe Thr
1               5

<210> SEQ ID NO 57
<211> LENGTH: 125
<212> TYPE: PRT
<213> ORGANISM: Homo sapiens

<400> SEQUENCE: 57

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Asp Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Glu Gly Leu Tyr Tyr Tyr Gly Ser Gly Ser Tyr Tyr Asn Gln
            100                 105                 110

Asp Tyr Trp Gly Gln Gly Thr Leu Val Thr Val Ser Ser
        115                 120                 125

<210> SEQ ID NO 58
<211> LENGTH: 5
<212> TYPE: PRT
<213> ORGANISM: Homo sapiens

<400> SEQUENCE: 58

Asp Tyr Tyr Met Tyr
1               5

<210> SEQ ID NO 59
<211> LENGTH: 17
<212> TYPE: PRT
<213> ORGANISM: Homo sapiens

<400> SEQUENCE: 59

Thr Ile Ser Asp Asp Gly Ser Tyr Thr Tyr Tyr Pro Asp Ser Val Lys
1               5                   10                  15

Gly

<210> SEQ ID NO 60
<211> LENGTH: 16
<212> TYPE: PRT
<213> ORGANISM: Homo sapiens

<400> SEQUENCE: 60

Glu Gly Leu Tyr Tyr Tyr Gly Ser Gly Ser Tyr Tyr Asn Gln Asp Tyr
1               5                   10                  15

<210> SEQ ID NO 61
<211> LENGTH: 108
<212> TYPE: PRT
<213> ORGANISM: Homo sapiens

<400> SEQUENCE: 61

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Leu Ser Ser Ala
            20                  25                  30

Leu Ala Trp Tyr Arg Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Thr Ser Tyr Pro Gln
                85                  90                  95

Ile Thr Phe Gly Gln Gly Thr Arg Leu Glu Ile Lys
            100                 105

<210> SEQ ID NO 62
<211> LENGTH: 11
<212> TYPE: PRT
<213> ORGANISM: Homo sapiens

<400> SEQUENCE: 62

Arg Ala Ser Gln Gly Leu Ser Ser Ala Leu Ala
1               5                   10

<210> SEQ ID NO 63
<211> LENGTH: 7
<212> TYPE: PRT
<213> ORGANISM: Homo sapiens

<400> SEQUENCE: 63

Asp Ala Ser Ser Leu Glu Ser
1               5

<210> SEQ ID NO 64
<211> LENGTH: 10
<212> TYPE: PRT
<213> ORGANISM: Homo sapiens

<400> SEQUENCE: 64

Gln Gln Phe Thr Ser Tyr Pro Gln Ile Thr
1               5                   10

<210> SEQ ID NO 65
<211> LENGTH: 118
<212> TYPE: PRT
<213> ORGANISM: Homo sapiens
<220> FEATURE:
<221> NAME/KEY: MOD_RES
<222> LOCATION: (52)..(52)
<223> OTHER INFORMATION: Any naturally occurring amino acid

<400> SEQUENCE: 65

Gln Leu Gln Leu Gln Glu Ser Gly Ser Gly Leu Val Lys Pro Ser Gln
1               5                   10                  15

-continued

```
Thr Leu Ser Leu Thr Cys Ala Val Ser Gly Gly Ser Ile Ser Ser Gly
            20                  25                  30

Gly His Ser Trp Ser Trp Ile Arg Gln Pro Pro Gly Lys Gly Leu Glu
        35                  40                  45

Trp Ile Gly Xaa Ile Tyr His Ser Gly Asn Thr Tyr Asp Asn Pro Ser
    50                  55                  60

Leu Lys Ser Arg Val Thr Ile Ala Val Asp Arg Ser Lys Asn Gln Leu
65                  70                  75                  80

Ser Leu Lys Leu Ser Phe Leu Thr Ala Ala Asp Thr Ala Val Tyr Tyr
                85                  90                  95

Cys Ala Arg Ser Ser Tyr Asp Phe Leu Thr Asp Trp Gly Gln Gly Thr
            100                 105                 110

Leu Val Thr Val Ser Ser
        115
```

<210> SEQ ID NO 66
<211> LENGTH: 7
<212> TYPE: PRT
<213> ORGANISM: Homo sapiens

<400> SEQUENCE: 66

```
Ser Gly Gly His Ser Trp Ser
1               5
```

<210> SEQ ID NO 67
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any naturally occurring amino acid

<400> SEQUENCE: 67

```
Xaa Ile Tyr His Ser Gly Asn Thr Tyr Asp Asn Pro Ser Leu Lys Ser
1               5                   10                  15
```

<210> SEQ ID NO 68
<211> LENGTH: 8
<212> TYPE: PRT
<213> ORGANISM: Homo sapiens

<400> SEQUENCE: 68

```
Ser Ser Tyr Asp Phe Leu Thr Asp
1               5
```

<210> SEQ ID NO 69
<211> LENGTH: 107
<212> TYPE: PRT
<213> ORGANISM: Homo sapiens

<400> SEQUENCE: 69

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Gly Phe Pro Ile
                 85                  90                  95

Thr Phe Gly Gln Gly Thr Arg Leu Glu Ile Lys
            100                 105
```

<210> SEQ ID NO 70
<211> LENGTH: 11
<212> TYPE: PRT
<213> ORGANISM: Homo sapiens

<400> SEQUENCE: 70

```
Arg Ala Ser Gln Gly Ile Ser Ser Trp Leu Ala
 1               5                  10
```

<210> SEQ ID NO 71
<211> LENGTH: 7
<212> TYPE: PRT
<213> ORGANISM: Homo sapiens

<400> SEQUENCE: 71

```
Ala Ala Ser Ser Leu Gln Ser
 1               5
```

<210> SEQ ID NO 72
<211> LENGTH: 9
<212> TYPE: PRT
<213> ORGANISM: Homo sapiens

<400> SEQUENCE: 72

```
Gln Gln Ala Asn Gly Phe Pro Ile Thr
 1               5
```

<210> SEQ ID NO 73
<211> LENGTH: 118
<212> TYPE: PRT
<213> ORGANISM: Homo sapiens
<220> FEATURE:
<221> NAME/KEY: MOD_RES
<222> LOCATION: (52)..(52)
<223> OTHER INFORMATION: Any naturally occurring amino acid

<400> SEQUENCE: 73

```
Gln Leu Gln Leu Gln Glu Ser Gly Ser Gly Leu Val Lys Pro Ser Gln
 1               5                  10                  15

Thr Leu Ser Leu Thr Cys Ala Val Ser Gly Gly Ser Ile Ser Ser Gly
                 20                  25                  30

Gly His Ser Trp Ser Trp Ile Arg Gln Pro Pro Gly Lys Gly Leu Glu
             35                  40                  45

Trp Ile Gly Xaa Ile Tyr His Ser Gly Asn Thr Tyr Asp Asn Pro Ser
 50                  55                  60

Leu Lys Ser Arg Val Thr Ile Ala Val Asp Arg Ser Lys Asn Gln Leu
 65                  70                  75                  80

Ser Leu Lys Leu Ser Phe Val Thr Ala Ala Asp Thr Ala Val Tyr Tyr
                 85                  90                  95

Cys Ala Arg Ser Ser Tyr Asp Ile Leu Thr Asp Trp Gly Gln Gly Thr
            100                 105                 110

Leu Val Thr Val Ser Ser
            115
```

-continued

<210> SEQ ID NO 74
<211> LENGTH: 7
<212> TYPE: PRT
<213> ORGANISM: Homo sapiens

<400> SEQUENCE: 74

Ser Gly Gly His Ser Trp Ser
1               5

<210> SEQ ID NO 75
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any naturally occurring amino acid

<400> SEQUENCE: 75

Xaa Ile Tyr His Ser Gly Asn Thr Tyr Asp Asn Pro Ser Leu Lys Ser
1               5                   10                  15

<210> SEQ ID NO 76
<211> LENGTH: 8
<212> TYPE: PRT
<213> ORGANISM: Homo sapiens

<400> SEQUENCE: 76

Ser Ser Tyr Asp Ile Leu Thr Asp
1               5

<210> SEQ ID NO 77
<211> LENGTH: 107
<212> TYPE: PRT
<213> ORGANISM: Homo sapiens

<400> SEQUENCE: 77

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Ile
                85                  90                  95

Thr Phe Gly Gln Gly Thr Arg Leu Glu Ile Lys
            100                 105

<210> SEQ ID NO 78
<211> LENGTH: 11
<212> TYPE: PRT
<213> ORGANISM: Homo sapiens

<400> SEQUENCE: 78

Arg Ala Ser Gln Gly Ile Ser Ser Trp Leu Ala
1               5                   10

<210> SEQ ID NO 79
<211> LENGTH: 7

```
<212> TYPE: PRT
<213> ORGANISM: Homo sapiens

<400> SEQUENCE: 79

Ala Ala Ser Ser Leu Gln Ser
1               5

<210> SEQ ID NO 80
<211> LENGTH: 9
<212> TYPE: PRT
<213> ORGANISM: Homo sapiens

<400> SEQUENCE: 80

Gln Gln Ala Asn Gly Phe Pro Ile Thr
1               5

<210> SEQ ID NO 81
<211> LENGTH: 118
<212> TYPE: PRT
<213> ORGANISM: Homo sapiens
<220> FEATURE:
<221> NAME/KEY: MOD_RES
<222> LOCATION: (52)..(52)
<223> OTHER INFORMATION: Any naturally occurring amino acid

<400> SEQUENCE: 81

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly His Ser Trp Ser Trp Ile Arg Gln Pro Pro Gly Lys Gly Leu Glu
        35                  40                  45

Trp Ile Gly Xaa Ile Tyr His Ser Gly Asn Thr Tyr Asp Asn Pro Ser
    50                  55                  60

Leu Lys Ser Arg Val Thr Ile Ser Val Asp Arg Ser Lys Asn Gln Val
65                  70                  75                  80

Ser Leu Lys Leu Ser Ser Val Thr Ala Ala Asp Thr Ala Val Tyr Tyr
                85                  90                  95

Cys Ala Arg Ser Ser Tyr Asp Ile Leu Thr Asp Trp Gly Gln Gly Thr
            100                 105                 110

Leu Val Thr Val Ser Ser
        115

<210> SEQ ID NO 82
<211> LENGTH: 7
<212> TYPE: PRT
<213> ORGANISM: Homo sapiens

<400> SEQUENCE: 82

Ser Gly Gly His Ser Trp Ser
1               5

<210> SEQ ID NO 83
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any naturally occurring amino acid

<400> SEQUENCE: 83

Xaa Ile Tyr His Ser Gly Asn Thr Tyr Asp Asn Pro Ser Leu Lys Ser
```

-continued

```
<210> SEQ ID NO 84
<211> LENGTH: 8
<212> TYPE: PRT
<213> ORGANISM: Homo sapiens

<400> SEQUENCE: 84

Ser Ser Tyr Asp Ile Leu Thr Asp
1               5

<210> SEQ ID NO 85
<211> LENGTH: 107
<212> TYPE: PRT
<213> ORGANISM: Homo sapiens

<400> SEQUENCE: 85

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln His Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Ile
                85                  90                  95

Thr Phe Gly Gln Gly Thr Arg Leu Glu Ile Lys
            100                 105

<210> SEQ ID NO 86
<211> LENGTH: 11
<212> TYPE: PRT
<213> ORGANISM: Homo sapiens

<400> SEQUENCE: 86

Arg Ala Ser Gln Gly Ile Ser Ser Trp Leu Ala
1               5                   10

<210> SEQ ID NO 87
<211> LENGTH: 7
<212> TYPE: PRT
<213> ORGANISM: Homo sapiens

<400> SEQUENCE: 87

Ala Ala Ser Ser Leu Gln Ser
1               5

<210> SEQ ID NO 88
<211> LENGTH: 9
<212> TYPE: PRT
<213> ORGANISM: Homo sapiens

<400> SEQUENCE: 88

Gln Gln Ala Asn Gly Phe Pro Ile Thr
1               5

<210> SEQ ID NO 89
<211> LENGTH: 118
<212> TYPE: PRT
```

<213> ORGANISM: Homo sapiens
<220> FEATURE:
<221> NAME/KEY: MOD_RES
<222> LOCATION: (52)..(52)
<223> OTHER INFORMATION: Any naturally occurring amino acid

<400> SEQUENCE: 89

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Xaa Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Ser Tyr Asp Ile Leu Thr Asp Trp Gly Gln Gly Thr
            100                 105                 110

Leu Val Thr Val Ser Ser
        115

<210> SEQ ID NO 90
<211> LENGTH: 7
<212> TYPE: PRT
<213> ORGANISM: Homo sapiens

<400> SEQUENCE: 90

Ser Gly Gly Tyr Ser Trp Ser
1               5

<210> SEQ ID NO 91
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any naturally occurring amino acid

<400> SEQUENCE: 91

Xaa Ile Tyr His Ser Gly Ser Thr Tyr Tyr Asn Pro Ser Leu Lys Ser
1               5                   10                  15

<210> SEQ ID NO 92
<211> LENGTH: 8
<212> TYPE: PRT
<213> ORGANISM: Homo sapiens

<400> SEQUENCE: 92

Ser Ser Tyr Asp Ile Leu Thr Asp
1               5

<210> SEQ ID NO 93
<211> LENGTH: 107
<212> TYPE: PRT
<213> ORGANISM: Homo sapiens

<400> SEQUENCE: 93

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 94
<211> LENGTH: 11
<212> TYPE: PRT
<213> ORGANISM: Homo sapiens

<400> SEQUENCE: 94

Arg Ala Ser Gln Gly Ile Ser Ser Trp Leu Ala
1               5                   10

<210> SEQ ID NO 95
<211> LENGTH: 7
<212> TYPE: PRT
<213> ORGANISM: Homo sapiens

<400> SEQUENCE: 95

Ala Ala Ser Ser Leu Gln Ser
1               5

<210> SEQ ID NO 96
<211> LENGTH: 9
<212> TYPE: PRT
<213> ORGANISM: Homo sapiens

<400> SEQUENCE: 96

Gln Gln Ala Asn Ser Phe Pro Ile Thr
1               5

<210> SEQ ID NO 97
<211> LENGTH: 119
<212> TYPE: PRT
<213> ORGANISM: Homo sapiens

<400> SEQUENCE: 97

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly

```
                     100                 105                 110
Thr Leu Val Thr Val Ser Ser
            115

<210> SEQ ID NO 98
<211> LENGTH: 5
<212> TYPE: PRT
<213> ORGANISM: Homo sapiens

<400> SEQUENCE: 98

Ser Tyr Gly Ile Ser
1               5

<210> SEQ ID NO 99
<211> LENGTH: 17
<212> TYPE: PRT
<213> ORGANISM: Homo sapiens

<400> SEQUENCE: 99

Trp Ile Ser Ala Tyr Asn Gly Tyr Thr Asn Tyr Ala Gln Lys Leu Gln
1               5                   10                  15

Gly

<210> SEQ ID NO 100
<211> LENGTH: 10
<212> TYPE: PRT
<213> ORGANISM: Homo sapiens

<400> SEQUENCE: 100

Asp Leu Arg Gly Thr Asn Tyr Phe Asp Tyr
1               5                   10

<210> SEQ ID NO 101
<211> LENGTH: 107
<212> TYPE: PRT
<213> ORGANISM: Homo sapiens

<400> SEQUENCE: 101

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 102
<211> LENGTH: 11
<212> TYPE: PRT
<213> ORGANISM: Homo sapiens

<400> SEQUENCE: 102

Arg Ala Ser Gln Gly Ile Ser Asn Trp Leu Ala
1               5                   10
```

<210> SEQ ID NO 103
<211> LENGTH: 7
<212> TYPE: PRT
<213> ORGANISM: Homo sapiens

<400> SEQUENCE: 103

Ala Ala Ser Ser Leu Leu Ser
1               5

<210> SEQ ID NO 104
<211> LENGTH: 9
<212> TYPE: PRT
<213> ORGANISM: Homo sapiens

<400> SEQUENCE: 104

Gln Gln Ala Asn Ser Phe Pro Ile Thr
1               5

<210> SEQ ID NO 105
<211> LENGTH: 118
<212> TYPE: PRT
<213> ORGANISM: Homo sapiens

<400> SEQUENCE: 105

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Ile Thr Gly Asp Phe Asp Tyr Trp Gly Gln Gly Thr
            100                 105                 110

Leu Val Thr Val Ser Ser
        115

<210> SEQ ID NO 106
<211> LENGTH: 5
<212> TYPE: PRT
<213> ORGANISM: Homo sapiens

<400> SEQUENCE: 106

Ser Tyr Trp Ile Gly
1               5

<210> SEQ ID NO 107
<211> LENGTH: 17
<212> TYPE: PRT
<213> ORGANISM: Homo sapiens

<400> SEQUENCE: 107

Ile Ile Tyr Pro Gly Asp Ser Asp Thr Arg Tyr Ser Pro Ser Phe Gln
1               5                   10                  15

Gly

<210> SEQ ID NO 108
<211> LENGTH: 9
<212> TYPE: PRT
<213> ORGANISM: Homo sapiens

<400> SEQUENCE: 108

Gln Glu Ile Thr Gly Asp Phe Asp Tyr
1               5

<210> SEQ ID NO 109
<211> LENGTH: 107
<212> TYPE: PRT
<213> ORGANISM: Homo sapiens

<400> SEQUENCE: 109

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Ala Ala Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 110
<211> LENGTH: 11
<212> TYPE: PRT
<213> ORGANISM: Homo sapiens

<400> SEQUENCE: 110

Arg Ala Ser Gln Gly Ile Ser Ser Ala Leu Ala
1               5                   10

<210> SEQ ID NO 111
<211> LENGTH: 7
<212> TYPE: PRT
<213> ORGANISM: Homo sapiens

<400> SEQUENCE: 111

Ala Ala Ser Ser Leu Glu Ser
1               5

<210> SEQ ID NO 112
<211> LENGTH: 9
<212> TYPE: PRT
<213> ORGANISM: Homo sapiens

<400> SEQUENCE: 112

Gln Gln Phe Asn Ser Tyr Pro Leu Thr
1               5

<210> SEQ ID NO 113
<211> LENGTH: 121
<212> TYPE: PRT
<213> ORGANISM: Homo sapiens

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Gly Ile Ser Trp Val Arg Gln Ala Pro Gly Gln Gly Leu Glu Trp Met
        35                  40                  45

Gly Trp Ile Ser Ala Phe Asn Gly His Thr Asp Tyr Ser Gln Lys Val
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Phe Tyr Cys
                85                  90                  95

Ala Arg Ser His Tyr Tyr Gly Ser Gly Ser Pro Phe Asp Tyr Trp Gly
            100                 105                 110

Gln Gly Thr Leu Val Thr Val Ser Ser
        115                 120

<210> SEQ ID NO 114
<211> LENGTH: 5
<212> TYPE: PRT
<213> ORGANISM: Homo sapiens

<400> SEQUENCE: 114

Asn Phe Gly Ile Ser
1               5

<210> SEQ ID NO 115
<211> LENGTH: 17
<212> TYPE: PRT
<213> ORGANISM: Homo sapiens

<400> SEQUENCE: 115

Trp Ile Ser Ala Phe Asn Gly His Thr Asp Tyr Ser Gln Lys Val Gln
1               5                   10                  15

Gly

<210> SEQ ID NO 116
<211> LENGTH: 12
<212> TYPE: PRT
<213> ORGANISM: Homo sapiens

<400> SEQUENCE: 116

Ser His Tyr Tyr Gly Ser Gly Ser Pro Phe Asp Tyr
1               5                   10

<210> SEQ ID NO 117
<211> LENGTH: 107
<212> TYPE: PRT
<213> ORGANISM: Homo sapiens

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly

```
                        50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Lys Ser Tyr Pro Trp
                 85                  90                  95

Thr Phe Gly Gln Gly Thr Lys Val Glu Ile Lys
            100                 105
```

<210> SEQ ID NO 118
<211> LENGTH: 11
<212> TYPE: PRT
<213> ORGANISM: Homo sapiens

<400> SEQUENCE: 118

```
Arg Ala Ser Gln Gly Ile Ser Asn Trp Leu Ala
 1               5                  10
```

<210> SEQ ID NO 119
<211> LENGTH: 7
<212> TYPE: PRT
<213> ORGANISM: Homo sapiens

<400> SEQUENCE: 119

```
Ala Ala Ser Ser Leu Gln Ser
 1               5
```

<210> SEQ ID NO 120
<211> LENGTH: 9
<212> TYPE: PRT
<213> ORGANISM: Homo sapiens

<400> SEQUENCE: 120

```
His Gln Tyr Lys Ser Tyr Pro Trp Thr
 1               5
```

<210> SEQ ID NO 121
<211> LENGTH: 123
<212> TYPE: PRT
<213> ORGANISM: Homo sapiens

<400> SEQUENCE: 121

```
Gln Val Gln Leu Val Gln Ser Gly Gly Glu Val Lys Lys Pro Gly Ala
 1               5                  10                  15

Ser Val Lys Val Ser Cys Lys Ala Ser Gly Tyr Thr Phe Thr Arg His
                20                  25                  30

Gly Ile Thr Trp Val Arg Gln Ala Pro Gly Gln Gly Leu Glu Trp Met
             35                  40                  45

Gly Trp Ile Ser Ala Asp Asn Gly Asn Thr Asn Tyr Ala Gln Lys Phe
         50                  55                  60

Gln Asp Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Phe Cys
                 85                  90                  95

Ala Arg Val Phe Arg Tyr Phe Asp Trp Leu Leu Pro Tyr Phe Asp Tyr
            100                 105                 110

Trp Gly Gln Gly Thr Leu Val Thr Val Ser Thr
            115                 120
```

<210> SEQ ID NO 122
<211> LENGTH: 5

```
<212> TYPE: PRT
<213> ORGANISM: Homo sapiens

<400> SEQUENCE: 122

Arg His Gly Ile Thr
1               5

<210> SEQ ID NO 123
<211> LENGTH: 17
<212> TYPE: PRT
<213> ORGANISM: Homo sapiens

<400> SEQUENCE: 123

Trp Ile Ser Ala Asp Asn Gly Asn Thr Asn Tyr Ala Gln Lys Phe Gln
1               5                   10                  15

Asp

<210> SEQ ID NO 124
<211> LENGTH: 14
<212> TYPE: PRT
<213> ORGANISM: Homo sapiens

<400> SEQUENCE: 124

Val Phe Arg Tyr Phe Asp Trp Leu Leu Pro Tyr Phe Asp Tyr
1               5                   10

<210> SEQ ID NO 125
<211> LENGTH: 108
<212> TYPE: PRT
<213> ORGANISM: Homo sapiens

<400> SEQUENCE: 125

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Val Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 126
<211> LENGTH: 12
<212> TYPE: PRT
<213> ORGANISM: Homo sapiens

<400> SEQUENCE: 126

Arg Ala Ser Gln Ser Val Ser Ser Ser Tyr Leu Ala
1               5                   10

<210> SEQ ID NO 127
<211> LENGTH: 7
<212> TYPE: PRT
<213> ORGANISM: Homo sapiens

<400> SEQUENCE: 127
```

```
Gly Val Phe Ser Arg Ala Thr
1               5

<210> SEQ ID NO 128
<211> LENGTH: 9
<212> TYPE: PRT
<213> ORGANISM: Homo sapiens

<400> SEQUENCE: 128

Gln Gln Tyr Gly Ser Ser Pro Tyr Thr
1               5

<210> SEQ ID NO 129
<211> LENGTH: 119
<212> TYPE: PRT
<213> ORGANISM: Homo sapiens

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Ala Tyr Phe Asp Tyr Trp Gly Gln Gly
            100                 105                 110

Thr Leu Val Thr Val Ser Ser
        115

<210> SEQ ID NO 130
<211> LENGTH: 5
<212> TYPE: PRT
<213> ORGANISM: Homo sapiens

<400> SEQUENCE: 130

Ser Tyr Gly Ile Ser
1               5

<210> SEQ ID NO 131
<211> LENGTH: 17
<212> TYPE: PRT
<213> ORGANISM: Homo sapiens

<400> SEQUENCE: 131

Trp Ile Ser Thr Tyr Asn Gly Tyr Thr Asn Tyr Ala Gln Lys Leu Gln
1               5                   10                  15

Gly

<210> SEQ ID NO 132
<211> LENGTH: 10
<212> TYPE: PRT
<213> ORGANISM: Homo sapiens

<400> SEQUENCE: 132
```

```
Asp Leu Arg Gly Thr Ala Tyr Phe Asp Tyr
1               5                   10

<210> SEQ ID NO 133
<211> LENGTH: 107
<212> TYPE: PRT
<213> ORGANISM: Homo sapiens

<400> SEQUENCE: 133

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln His Lys Pro Gly Lys Ala Pro Lys Leu Leu Ile
            35                  40                  45

Tyr Ala Ala Ser Ser Leu Leu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 134
<211> LENGTH: 11
<212> TYPE: PRT
<213> ORGANISM: Homo sapiens

<400> SEQUENCE: 134

Arg Ala Ser Gln Gly Ile Ser Asn Trp Leu Ala
1               5                   10

<210> SEQ ID NO 135
<211> LENGTH: 7
<212> TYPE: PRT
<213> ORGANISM: Homo sapiens

<400> SEQUENCE: 135

Ala Ala Ser Ser Leu Leu Ser
1               5

<210> SEQ ID NO 136
<211> LENGTH: 9
<212> TYPE: PRT
<213> ORGANISM: Homo sapiens

<400> SEQUENCE: 136

Gln Gln Ala Asn Ser Phe Pro Ile Thr
1               5

<210> SEQ ID NO 137
<211> LENGTH: 119
<212> TYPE: PRT
<213> ORGANISM: Homo sapiens

<400> SEQUENCE: 137

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Ser Tyr
                20                  25                  30
```

```
Gly Ile Ser Trp Val Arg Gln Ala Pro Gly His Gly Leu Glu Trp Met
            35                  40                  45

Gly Trp Ile Ser Ala Tyr Asn Gly Tyr Thr Asn Tyr Ala Gln Lys Leu
 50                      55                  60

Gln Gly Arg Val Thr Met Thr Ala Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Arg Gly Thr Asn Tyr Phe Asp Tyr Trp Gly Gln Gly
                100                 105                 110

Thr Leu Val Thr Val Ser Ser
            115
```

<210> SEQ ID NO 138
<211> LENGTH: 107
<212> TYPE: PRT
<213> ORGANISM: Homo sapiens

<400> SEQUENCE: 138

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Asn Trp
             20                  25                  30

Leu Ala Trp Tyr Gln His Lys Pro Gly Lys Ala Pro Lys Leu Leu Ile
         35                  40                  45

Tyr Ala Ala Ser Ser Leu Leu Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
                100                 105
```

<210> SEQ ID NO 139
<211> LENGTH: 119
<212> TYPE: PRT
<213> ORGANISM: Homo sapiens

<400> SEQUENCE: 139

```
Gln Val Gln Leu Val Gln Ser Gly Ala Glu Val Lys Lys Pro Gly Ala
 1               5                  10                  15

Ser Val Lys Val Ser Cys Glu Ala Ser Gly Tyr Thr Phe Thr Asn Tyr
             20                  25                  30

Gly Ile Ser Trp Val Arg Gln Ala Pro Gly His Gly Leu Glu Trp Met
         35                  40                  45

Gly Trp Ile Ser Ala Tyr Asn Gly Tyr Thr Asn Tyr Ala Gln Lys Leu
 50                      55                  60

Gln Gly Arg Val Thr Met Thr Thr Asp Thr Ser Thr Thr Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Arg Gly Thr Asn Tyr Phe Asp Tyr Trp Gly Gln Gly
                100                 105                 110

Thr Leu Val Thr Val Ser Ser
            115
```

<210> SEQ ID NO 140
<211> LENGTH: 107
<212> TYPE: PRT
<213> ORGANISM: Homo sapiens

<400> SEQUENCE: 140

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 141
<211> LENGTH: 119
<212> TYPE: PRT
<213> ORGANISM: Homo sapiens

<400> SEQUENCE: 141

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser
        115

<210> SEQ ID NO 142
<211> LENGTH: 107
<212> TYPE: PRT
<213> ORGANISM: Homo sapiens

<400> SEQUENCE: 142

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly

```
                 50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
                100                 105

<210> SEQ ID NO 143
<211> LENGTH: 119
<212> TYPE: PRT
<213> ORGANISM: Homo sapiens

<400> SEQUENCE: 143

Gln Val Gln Leu Val Gln Ser Gly Ala Glu Val Lys Lys Pro Gly Ala
  1               5                  10                  15

Ser Val Lys Val Ser Cys Glu Thr Ser Gly Tyr Thr Phe Thr Ser Tyr
                 20                  25                  30

Gly Ile Ser Trp Val Arg Gln Ala Pro Gly His Gly Leu Glu Trp Met
                 35                  40                  45

Gly Trp Ile Ser Ala Tyr Asn Gly Tyr Thr Asn Tyr Ala Gln Lys Leu
             50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asp Leu Arg Gly Thr Asn Tyr Phe Asp Tyr Trp Gly Gln Gly
                100                 105                 110

Thr Leu Val Thr Val Ser Ser
            115

<210> SEQ ID NO 144
<211> LENGTH: 107
<212> TYPE: PRT
<213> ORGANISM: Homo sapiens

<400> SEQUENCE: 144

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Asn Trp
                 20                  25                  30

Leu Ala Trp Phe Gln His Lys Pro Gly Lys Ala Pro Lys Leu Leu Ile
                 35                  40                  45

Tyr Ala Ala Ser Ser Leu Leu Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
                100                 105

<210> SEQ ID NO 145
<211> LENGTH: 121
<212> TYPE: PRT
<213> ORGANISM: Homo sapiens

<400> SEQUENCE: 145
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Gly Phe Gly Trp Val Arg Gln Ala Pro Gly Gln Gly Leu Glu Trp Met
            35                  40                  45

Gly Arg Ile Ser Pro Ile Leu Gly Ile Thr Asn Tyr Ala Gln Met Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Tyr Asp Trp Pro Asp Thr Phe Asp Ile Trp Gly
            100                 105                 110

Gln Gly Thr Met Val Ile Val Ser Ser
            115                 120

<210> SEQ ID NO 146
<211> LENGTH: 107
<212> TYPE: PRT
<213> ORGANISM: Homo sapiens

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105

<210> SEQ ID NO 147
<211> LENGTH: 121
<212> TYPE: PRT
<213> ORGANISM: Homo sapiens

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Gly Ile Gly Trp Val Arg Gln Ala Pro Gly Gln Gly Leu Glu Trp Met
            35                  40                  45

Gly Arg Ile Phe Pro Ile Leu Gly Thr Ala Asn Tyr Ala Gln Met Phe
        50                  55                  60

Gln Gly Arg Val Thr Ile Thr Ala Asp Lys Ser Thr Ser Thr Ala Tyr
65                  70                  75                  80

Ile Glu Leu Thr Ser Leu Arg Ser Glu Asp Thr Ala Val Tyr Tyr Cys
                85                  90                  95

```
Ala Arg Asp Val Gly Tyr Asp Ser Ala Asp Ala Phe Asp Ile Trp Gly
            100                 105                 110

Gln Gly Thr Met Val Thr Val Ser Ser
        115                 120
```

<210> SEQ ID NO 148
<211> LENGTH: 107
<212> TYPE: PRT
<213> ORGANISM: Homo sapiens

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105
```

<210> SEQ ID NO 149
<211> LENGTH: 121
<212> TYPE: PRT
<213> ORGANISM: Homo sapiens

<400> SEQUENCE: 149

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Gly Trp Val Arg Gln Ala Pro Gly Gln Gly Leu Glu Trp Met
        35                  40                  45

Gly Arg Val Phe Pro Ile Leu Gly Thr Ala Asn Tyr Ala Gln Met Phe
    50                  55                  60

Gln Gly Arg Val Thr Ile Thr Ala Asp Lys Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Arg Asp Val Gly Tyr Asp Ser Ala Asp Ala Phe Asp Ile Trp Gly
            100                 105                 110

Gln Gly Thr Met Val Thr Val Ser Ser
        115                 120
```

<210> SEQ ID NO 150
<211> LENGTH: 107
<212> TYPE: PRT
<213> ORGANISM: Homo sapiens

<400> SEQUENCE: 150

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105

<210> SEQ ID NO 151
<211> LENGTH: 123
<212> TYPE: PRT
<213> ORGANISM: Homo sapiens

<400> SEQUENCE: 151

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Phe Ile Ser Tyr Asp Gly Ser Asn Lys Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Leu Trp Phe Gly Glu Leu Trp Gly Tyr Phe Asp Leu
            100                 105                 110

Trp Gly Arg Gly Thr Leu Val Thr Val Ser Ser
        115                 120

<210> SEQ ID NO 152
<211> LENGTH: 107
<212> TYPE: PRT
<213> ORGANISM: Homo sapiens

<400> SEQUENCE: 152

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Ala Asn Ser Phe Thr Trp
                85                  90                  95

Thr Phe Gly Gln Gly Thr Lys Val Glu Ile Lys
            100                 105

```
<210> SEQ ID NO 153
<211> LENGTH: 123
<212> TYPE: PRT
<213> ORGANISM: Homo sapiens

<400> SEQUENCE: 153

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Phe Ile Ser Tyr Asp Gly Ser Lys Asp Tyr Ala Asp Ser Val
    50                  55                  60

Lys Gly Arg Phe Thr Ile Phe Arg Asp Asn Ser Lys Asn Thr Leu Tyr
65                  70                  75                  80

Leu Gln Met Ser Ser Leu Arg Ala Ala Asp Thr Ala Val Tyr Tyr Cys
                85                  90                  95

Ala Arg Glu Leu Leu Trp Phe Gly Leu Trp Gly Tyr Phe Asp Leu
            100                 105                 110

Trp Gly Arg Gly Thr Leu Val Thr Val Ser Ser
            115                 120

<210> SEQ ID NO 154
<211> LENGTH: 107
<212> TYPE: PRT
<213> ORGANISM: Homo sapiens

<400> SEQUENCE: 154

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Thr Trp
                85                  90                  95

Thr Phe Gly Gln Gly Thr Lys Val Glu Ile Lys
            100                 105

<210> SEQ ID NO 155
<211> LENGTH: 117
<212> TYPE: PRT
<213> ORGANISM: Homo sapiens

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Ile Thr Tyr Tyr Ala Asp Ser Val
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Trp Gly Ser Asp Tyr Trp Gly Gln Gly Thr Leu
            100                 105                 110

Val Thr Val Ser Ser
            115

<210> SEQ ID NO 156
<211> LENGTH: 107
<212> TYPE: PRT
<213> ORGANISM: Homo sapiens

<400> SEQUENCE: 156

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Thr Phe Gly Pro Gly Thr Lys Val Asp Ile Lys
            100                 105

<210> SEQ ID NO 157
<211> LENGTH: 117
<212> TYPE: PRT
<213> ORGANISM: Homo sapiens

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ile Thr Tyr Tyr Ala Asp Ser Glu
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Trp Gly Ser Asp Cys Trp Gly Gln Gly Thr Leu
            100                 105                 110

Val Thr Val Ser Ser
            115

<210> SEQ ID NO 158
<211> LENGTH: 107
<212> TYPE: PRT

<213> ORGANISM: Homo sapiens

<400> SEQUENCE: 158

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Thr Phe Gly Pro Gly Thr Lys Val Asp Ile Lys
            100                 105

<210> SEQ ID NO 159
<211> LENGTH: 118
<212> TYPE: PRT
<213> ORGANISM: Homo sapiens

<400> SEQUENCE: 159

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly His Ser Trp Ser Trp Ile Arg Gln Pro Pro Gly Lys Gly Leu Glu
        35                  40                  45

Trp Ile Gly Cys Leu Tyr His Ser Gly Asn Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Ser Tyr Asp Ile Leu Thr Asp Trp Gly Gln Gly Ile
            100                 105                 110

Leu Val Thr Val Ser Ser
        115

<210> SEQ ID NO 160
<211> LENGTH: 107
<212> TYPE: PRT
<213> ORGANISM: Homo sapiens

<400> SEQUENCE: 160

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 161
<211> LENGTH: 118
<212> TYPE: PRT
<213> ORGANISM: Homo sapiens

<400> SEQUENCE: 161

Gln Leu Gln Leu Gln Glu Ser Gly Ser Gly Leu Val Lys Pro Ser Gln
1               5                   10                  15

Thr Leu Ser Leu Thr Cys Gly Val Ser Gly Gly Ser Ile Ser Ser Gly
            20                  25                  30

Gly His Ser Trp Ser Trp Ile Arg Gln Pro Pro Gly Lys Gly Leu Glu
        35                  40                  45

Trp Ile Gly Cys Leu Tyr His Ser Gly Asn Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Ser Tyr Asp Ile Leu Thr Asp Trp Gly Gln Gly Thr
            100                 105                 110

Leu Val Thr Val Ser Ser
        115

<210> SEQ ID NO 162
<211> LENGTH: 107
<212> TYPE: PRT
<213> ORGANISM: Homo sapiens

<400> SEQUENCE: 162

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 163
<211> LENGTH: 118
<212> TYPE: PRT
<213> ORGANISM: Homo sapiens

<400> SEQUENCE: 163

Gln Leu Gln Leu Gln Glu Ser Gly Ser Gly Leu Val Lys Pro Ser Gln
1               5                   10                  15
```

Thr Leu Ser Leu Thr Cys Ala Val Ser Gly Gly Ser Ile Ser Ser Gly
            20                  25                  30

Gly His Ser Trp Ser Trp Ile Arg Gln Pro Pro Gly Lys Gly Leu Glu
        35                  40                  45

Trp Ile Gly Cys Ile Tyr His Ser Gly Asn Thr Tyr Asp Asn Pro Ser
    50                  55                  60

Leu Lys Ser Arg Val Thr Ile Ala Val Asp Arg Ser Lys Asn Gln Leu
65                  70                  75                  80

Ser Leu Lys Leu Ser Phe Val Thr Ala Ala Asp Thr Ala Val Tyr Tyr
                85                  90                  95

Cys Ala Arg Ser Ser Tyr Asp Ile Leu Thr Asp Trp Gly Gln Gly Thr
            100                 105                 110

Leu Val Thr Val Ser Ser
        115

<210> SEQ ID NO 164
<211> LENGTH: 107
<212> TYPE: PRT
<213> ORGANISM: Homo sapiens

<400> SEQUENCE: 164

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Ile
                85                  90                  95

Thr Phe Gly Gln Gly Thr Arg Leu Glu Ile Lys
            100                 105

<210> SEQ ID NO 165
<211> LENGTH: 118
<212> TYPE: PRT
<213> ORGANISM: Homo sapiens

<400> SEQUENCE: 165

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly His Ser Trp Ser Trp Ile Arg Gln Pro Pro Gly Lys Gly Leu Glu
        35                  40                  45

Trp Ile Gly Cys Ile Tyr His Ser Gly Asn Thr Tyr Asp Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Ser Tyr Asp Ile Leu Thr Asp Trp Gly Gln Gly Thr
            100                 105                 110

```
Leu Val Thr Val Ser Ser
        115

<210> SEQ ID NO 166
<211> LENGTH: 107
<212> TYPE: PRT
<213> ORGANISM: Homo sapiens

<400> SEQUENCE: 166

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Ile
                85                  90                  95

Thr Phe Gly Gln Gly Thr Arg Leu Glu Ile Lys
            100                 105

<210> SEQ ID NO 167
<211> LENGTH: 118
<212> TYPE: PRT
<213> ORGANISM: Homo sapiens

<400> SEQUENCE: 167

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Val Thr Gly Asp Phe Asp Tyr Trp Gly Gln Gly Thr
            100                 105                 110

Leu Val Thr Val Ser Ser
        115

<210> SEQ ID NO 168
<211> LENGTH: 107
<212> TYPE: PRT
<213> ORGANISM: Homo sapiens

<400> SEQUENCE: 168

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
```

```
                    35                  40                  45
Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                     85                  90                  95

Thr Phe Gly Gly Gly Thr Lys Val Glu Ile Lys
                100                 105

<210> SEQ ID NO 169
<211> LENGTH: 118
<212> TYPE: PRT
<213> ORGANISM: Homo sapiens

<400> SEQUENCE: 169

Glu Val Gln Leu Val Gln Ser Gly Gly Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Gln Glu Val Thr Gly Asp Phe Asp Tyr Trp Gly Gln Gly Thr
                100                 105                 110

Leu Val Thr Val Ser Ser
        115

<210> SEQ ID NO 170
<211> LENGTH: 107
<212> TYPE: PRT
<213> ORGANISM: Homo sapiens

<400> SEQUENCE: 170

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105

<210> SEQ ID NO 171
<211> LENGTH: 118
<212> TYPE: PRT
```

<213> ORGANISM: Homo sapiens

<400> SEQUENCE: 171

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Ile Thr Gly Glu Phe Asp Tyr Trp Gly Gln Gly Thr
            100                 105                 110

Leu Val Thr Val Ser Ser
            115

<210> SEQ ID NO 172
<211> LENGTH: 107
<212> TYPE: PRT
<213> ORGANISM: Homo sapiens

<400> SEQUENCE: 172

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 173
<211> LENGTH: 118
<212> TYPE: PRT
<213> ORGANISM: Homo sapiens

<400> SEQUENCE: 173

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asn Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Ile Thr Gly Asp Phe Asp Tyr Trp Gly Gln Gly Thr
            100                 105                 110

Leu Val Thr Val Ser Ser
        115

<210> SEQ ID NO 174
<211> LENGTH: 107
<212> TYPE: PRT
<213> ORGANISM: Homo sapiens

<400> SEQUENCE: 174

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 175
<211> LENGTH: 118
<212> TYPE: PRT
<213> ORGANISM: Homo sapiens

<400> SEQUENCE: 175

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Ile Thr Gly Asp Phe Asp Tyr Trp Gly Gln Gly Thr
            100                 105                 110

Leu Val Thr Val Ser Ser
        115

<210> SEQ ID NO 176
<211> LENGTH: 107
<212> TYPE: PRT
<213> ORGANISM: Homo sapiens

<400> SEQUENCE: 176

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Asn Leu Leu Ile
         35                  40                  45

Tyr Ala Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
             100                 105
```

<210> SEQ ID NO 177
<211> LENGTH: 118
<212> TYPE: PRT
<213> ORGANISM: Homo sapiens

<400> SEQUENCE: 177

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ile Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Glu Ile Thr Gly Asp Phe Asp Tyr Trp Gly Gln Gly Thr
             100                 105                 110

Leu Val Thr Val Ser Ser
        115
```

<210> SEQ ID NO 178
<211> LENGTH: 107
<212> TYPE: PRT
<213> ORGANISM: Homo sapiens

<400> SEQUENCE: 178

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Val Ala Ser Ser Leu Glu Ser Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Glu Asp Phe Ala Thr Tyr Tyr Cys Gln Gln Phe Asn Ser Tyr Pro Ile
                 85                  90                  95
```

```
Thr Phe Gly Gln Gly Thr Arg Leu Glu Ile Lys
        100                 105

<210> SEQ ID NO 179
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (4)..(4)
<223> OTHER INFORMATION: Phe or Ile
<220> FEATURE:
<221> NAME/KEY: MOD_RES
<222> LOCATION: (5)..(5)
<223> OTHER INFORMATION: Ser or Gly

<400> SEQUENCE: 179

Ser Xaa Xaa Xaa Xaa
1               5

<210> SEQ ID NO 180
<211> LENGTH: 17
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (3)..(3)
<223> OTHER INFORMATION: Ile, Ser or Phe
<220> FEATURE:
<221> NAME/KEY: MOD_RES
<222> LOCATION: (8)..(8)
<223> OTHER INFORMATION: Ile or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (14)..(14)
<223> OTHER INFORMATION: Lys or Met

<400> SEQUENCE: 180

Arg Xaa Xaa Pro Ile Leu Gly Xaa Xaa Asn Tyr Ala Gln Xaa Phe Gln
1               5                   10                  15

Gly

<210> SEQ ID NO 181
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Trp or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (9)..(9)
```

```
<223> OTHER INFORMATION: Thr or Ala

<400> SEQUENCE: 181

Asp Val Gly Tyr Asp Xaa Xaa Asp Xaa Phe Asp Ile
1               5                   10

<210> SEQ ID NO 182
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Asp, Glu or Asn

<400> SEQUENCE: 182

Ile Ile Tyr Pro Gly Asp Ser Xaa Thr Arg Tyr Ser Pro Ser Phe Gln
1               5                   10                  15

Gly

<210> SEQ ID NO 183
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Val or Ile
<220> FEATURE:
<221> NAME/KEY: MOD_RES
<222> LOCATION: (6)..(6)
<223> OTHER INFORMATION: Glu or Asp

<400> SEQUENCE: 183

Gln Glu Xaa Thr Gly Xaa Phe Asp Tyr
1               5

<210> SEQ ID NO 184
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Val or Phe
<220> FEATURE:
<221> NAME/KEY: MOD_RES
<222> LOCATION: (8)..(8)
<223> OTHER INFORMATION: Asn or Ser
<220> FEATURE:
<221> NAME/KEY: MOD_RES
<222> LOCATION: (10)..(10)
<223> OTHER INFORMATION: Asp or Tyr
<220> FEATURE:
<221> NAME/KEY: MOD_RES
<222> LOCATION: (11)..(11)
<223> OTHER INFORMATION: Tyr or Phe

<400> SEQUENCE: 184

Xaa Ile Ser Tyr Asp Gly Ser Xaa Lys Xaa Xaa Ala Asp Ser Val Lys
1               5                   10                  15

Gly

<210> SEQ ID NO 185
<211> LENGTH: 18
<212> TYPE: PRT
<213> ORGANISM: Homo sapiens
<220> FEATURE:
<221> NAME/KEY: MOD_RES
```

```
<222> LOCATION: (6)..(6)
<223> OTHER INFORMATION: Ser or absent
<220> FEATURE:
<221> NAME/KEY: MOD_RES
<222> LOCATION: (13)..(13)
<223> OTHER INFORMATION: Val or Ala

<400> SEQUENCE: 185

Ala Ile Ser Gly Ser Xaa Gly Gly Ser Thr Tyr Tyr Xaa Asp Ser Val
1               5                   10                  15

Lys Gly

<210> SEQ ID NO 186
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (5)..(5)
<223> OTHER INFORMATION: Ser or Thr

<400> SEQUENCE: 186

Xaa Tyr Ala Met Xaa
1               5

<210> SEQ ID NO 187
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ala or Val
<220> FEATURE:
<221> NAME/KEY: MOD_RES
<222> LOCATION: (8)..(8)
<223> OTHER INFORMATION: Ser or Ile
<220> FEATURE:
<221> NAME/KEY: MOD_RES
<222> LOCATION: (15)..(15)
<223> OTHER INFORMATION: Val or Glu

<400> SEQUENCE: 187

Xaa Ile Ser Gly Ser Gly Gly Xaa Thr Tyr Tyr Ala Asp Ser Xaa Lys
1               5                   10                  15

Gly

<210> SEQ ID NO 188
<211> LENGTH: 8
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Tyr or Cys

<400> SEQUENCE: 188

Asp Arg Gly Trp Gly Ser Asp Xaa
1               5

<210> SEQ ID NO 189
<211> LENGTH: 5
<212> TYPE: PRT
<213> ORGANISM: Homo sapiens
<220> FEATURE:
```

```
<221> NAME/KEY: MOD_RES
<222> LOCATION: (5)..(5)
<223> OTHER INFORMATION: Tyr or Ser

<400> SEQUENCE: 189

Asp Tyr Tyr Met Xaa
1               5

<210> SEQ ID NO 190
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Thr or Tyr
<220> FEATURE:
<221> NAME/KEY: MOD_RES
<222> LOCATION: (4)..(5)
<223> OTHER INFORMATION: Asp or Ser
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (10)..(10)
<223> OTHER INFORMATION: Tyr or Asn
<220> FEATURE:
<221> NAME/KEY: MOD_RES
<222> LOCATION: (12)..(12)
<223> OTHER INFORMATION: Pro or Ala

<400> SEQUENCE: 190

Xaa Ile Ser Xaa Xaa Xaa Ser Tyr Thr Xaa Tyr Xaa Asp Ser Val Lys
1               5                   10                  15
Gly

<210> SEQ ID NO 191
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Tyr or His

<400> SEQUENCE: 191

Ser Gly Gly Xaa Ser Trp Ser
1               5

<210> SEQ ID NO 192
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (10)..(10)
<223> OTHER INFORMATION: Tyr or Asp
```

-continued

<400> SEQUENCE: 192

Xaa Xaa Tyr His Ser Gly Xaa Thr Tyr Xaa Asn Pro Ser Leu Lys Ser
1               5                   10                  15

<210> SEQ ID NO 193
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phe or Ile

<400> SEQUENCE: 193

Ser Ser Tyr Asp Xaa Leu Thr Asp
1               5

<210> SEQ ID NO 194
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ser or Asn

<400> SEQUENCE: 194

Xaa Tyr Gly Ile Ser
1               5

<210> SEQ ID NO 195
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Ala or Thr
<220> FEATURE:
<221> NAME/KEY: MOD_RES
<222> LOCATION: (8)..(8)
<223> OTHER INFORMATION: Asn or Tyr

<400> SEQUENCE: 195

Trp Ile Ser Xaa Tyr Asn Gly Xaa Thr Asn Tyr Ala Gln Lys Leu Gln
1               5                   10                  15

Gly

<210> SEQ ID NO 196
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Ala or Asn

<400> SEQUENCE: 196

Asp Leu Arg Gly Thr Xaa Tyr Phe Asp Tyr
1               5                   10

<210> SEQ ID NO 197
<211> LENGTH: 5
<212> TYPE: PRT
<213> ORGANISM: Homo sapiens
<220> FEATURE:
<221> NAME/KEY: MOD_RES
<222> LOCATION: (1)..(1)

```
<223> OTHER INFORMATION: Asn or Ser
<220> FEATURE:
<221> NAME/KEY: MOD_RES
<222> LOCATION: (2)..(2)
<223> OTHER INFORMATION: Phe or Tyr

<400> SEQUENCE: 197

Xaa Xaa Gly Ile Ser
1               5

<210> SEQ ID NO 198
<211> LENGTH: 17
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phe or Tyr
<220> FEATURE:
<221> NAME/KEY: MOD_RES
<222> LOCATION: (8)..(8)
<223> OTHER INFORMATION: His or Asn
<220> FEATURE:
<221> NAME/KEY: MOD_RES
<222> LOCATION: (10)..(10)
<223> OTHER INFORMATION: Asp or Asn
<220> FEATURE:
<221> NAME/KEY: MOD_RES
<222> LOCATION: (12)..(12)
<223> OTHER INFORMATION: Ser or Ala
<220> FEATURE:
<221> NAME/KEY: MOD_RES
<222> LOCATION: (15)..(15)
<223> OTHER INFORMATION: Val or Leu

<400> SEQUENCE: 198

Trp Ile Ser Ala Xaa Asn Gly Xaa Thr Xaa Tyr Xaa Gln Lys Xaa Gln
1               5                   10                  15

Gly

<210> SEQ ID NO 199
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Arg or Ser
<220> FEATURE:
<221> NAME/KEY: MOD_RES
<222> LOCATION: (2)..(2)
<223> OTHER INFORMATION: His or Tyr
<220> FEATURE:
<221> NAME/KEY: MOD_RES
<222> LOCATION: (5)..(5)
<223> OTHER INFORMATION: Thr or Ser

<400> SEQUENCE: 199

Xaa Xaa Gly Ile Xaa
1               5

<210> SEQ ID NO 200
<211> LENGTH: 17
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Asp or Tyr
<220> FEATURE:
<221> NAME/KEY: MOD_RES
<222> LOCATION: (15)..(15)
```

```
<223> OTHER INFORMATION: Phe or Leu
<220> FEATURE:
<221> NAME/KEY: MOD_RES
<222> LOCATION: (17)..(17)
<223> OTHER INFORMATION: Asp or Gly

<400> SEQUENCE: 200

Trp Ile Ser Ala Xaa Asn Gly Asn Thr Asn Tyr Ala Gln Lys Xaa Gln
1               5                   10                  15

Xaa

<210> SEQ ID NO 201
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phe or Leu
<220> FEATURE:
<221> NAME/KEY: MOD_RES
<222> LOCATION: (10)..(10)
<223> OTHER INFORMATION: Phe or absent

<400> SEQUENCE: 201

Val Xaa Arg Tyr Phe Asp Trp Leu Leu Xaa Tyr Phe Asp Tyr
1               5                   10

<210> SEQ ID NO 202
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Tyr or Phe
<220> FEATURE:
<221> NAME/KEY: MOD_RES
<222> LOCATION: (8)..(8)
<223> OTHER INFORMATION: Phe or Trp

<400> SEQUENCE: 202

Gln Gln Tyr Asn Ser Xaa Pro Xaa Thr
1               5

<210> SEQ ID NO 203
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Asp, Val or Ala

<400> SEQUENCE: 203

Xaa Ala Ser Ser Leu Glu Ser
1               5

<210> SEQ ID NO 204
<211> LENGTH: 10
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: Arg, Ile, Leu, Trp or Met-Tyr, therefore, this
      region may encompass 1-2 residues

<400> SEQUENCE: 204
```

```
Gln Gln Phe Asn Ser Tyr Pro Xaa Xaa Thr
1               5                   10
```

<210> SEQ ID NO 205
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Gln or Glu
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (4)..(4)
<223> OTHER INFORMATION: Asn or Ser
<220> FEATURE:
<221> NAME/KEY: MOD_RES
<222> LOCATION: (7)..(7)
<223> OTHER INFORMATION: Pro or Thr

<400> SEQUENCE: 205

```
Gln Xaa Xaa Xaa Ser Phe Xaa Trp Thr
1               5
```

<210> SEQ ID NO 206
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Ile or absent

<400> SEQUENCE: 206

```
Gln Gln Ala Asn Ser Phe Pro Xaa Thr
1               5
```

<210> SEQ ID NO 207
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Thr or Asn
<220> FEATURE:
<221> NAME/KEY: MOD_RES
<222> LOCATION: (8)..(8)
<223> OTHER INFORMATION: Gln or absent

<400> SEQUENCE: 207

```
Gln Gln Phe Xaa Ser Tyr Pro Xaa Ile Thr
1               5                   10
```

<210> SEQ ID NO 208
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Gly or Ser

<400> SEQUENCE: 208

```
Gln Gln Ala Asn Xaa Phe Pro Ile Thr
1               5
```

```
<210> SEQ ID NO 209
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Ser or Asn

<400> SEQUENCE: 209

Arg Ala Ser Gln Gly Ile Ser Xaa Trp Leu Ala
1               5                   10

<210> SEQ ID NO 210
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Gln or Leu

<400> SEQUENCE: 210

Ala Ala Ser Ser Leu Xaa Ser
1               5

<210> SEQ ID NO 211
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: His or Gln
<220> FEATURE:
<221> NAME/KEY: MOD_RES
<222> LOCATION: (4)..(4)
<223> OTHER INFORMATION: Lys or Asn

<400> SEQUENCE: 211

Xaa Gln Tyr Xaa Ser Tyr Pro Trp Thr
1               5

<210> SEQ ID NO 212
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Val or Ala
<220> FEATURE:
<221> NAME/KEY: MOD_RES
<222> LOCATION: (3)..(3)
<223> OTHER INFORMATION: Phe or Ser

<400> SEQUENCE: 212

Gly Xaa Xaa Ser Arg Ala Thr
1               5

<210> SEQ ID NO 213
<211> LENGTH: 4
<212> TYPE: PRT
<213> ORGANISM: Homo sapiens

<400> SEQUENCE: 213

Cys Pro Pro Cys
1
```

<210> SEQ ID NO 214
<211> LENGTH: 15
<212> TYPE: PRT
<213> ORGANISM: Homo sapiens

<400> SEQUENCE: 214

Glu Pro Lys Ser Cys Asp Lys Thr His Thr Cys Pro Pro Cys Pro
1               5                   10                  15

<210> SEQ ID NO 215
<211> LENGTH: 12
<212> TYPE: PRT
<213> ORGANISM: Homo sapiens

<400> SEQUENCE: 215

Glu Arg Lys Cys Cys Val Glu Cys Pro Pro Cys Pro
1               5                   10

<210> SEQ ID NO 216
<211> LENGTH: 14
<212> TYPE: PRT
<213> ORGANISM: Homo sapiens

<400> SEQUENCE: 216

Glu Pro Lys Ser Asp Lys Thr His Thr Cys Pro Pro Cys Pro
1               5                   10

<210> SEQ ID NO 217
<211> LENGTH: 15
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 217

Glu Pro Lys Ser Xaa Asp Lys Thr His Thr Cys Pro Pro Cys Pro
1               5                   10                  15

<210> SEQ ID NO 218
<211> LENGTH: 62
<212> TYPE: PRT
<213> ORGANISM: Homo sapiens

<400> SEQUENCE: 218

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
        50                  55                  60

<210> SEQ ID NO 219
<211> LENGTH: 13
<212> TYPE: PRT
<213> ORGANISM: Homo sapiens

<400> SEQUENCE: 219

Glu Pro Lys Ser Cys Asp Cys His Cys Pro Pro Cys Pro
1               5                   10

<210> SEQ ID NO 220
<211> LENGTH: 15
<212> TYPE: PRT
<213> ORGANISM: Homo sapiens

<400> SEQUENCE: 220

Glu Pro Lys Ser Ser Asp Lys Thr His Thr Cys Pro Pro Cys Pro
1               5                   10                  15

<210> SEQ ID NO 221
<211> LENGTH: 98
<212> TYPE: PRT
<213> ORGANISM: Mouse
<220> FEATURE:
<221> NAME/KEY: misc_feature
<222> LOCATION: (1)..(98)
<223> OTHER INFORMATION: IgHV1-18-1

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 222
<211> LENGTH: 119
<212> TYPE: PRT
<213> ORGANISM: Homo sapiens
<220> FEATURE:
<221> NAME/KEY: misc_feature
<222> LOCATION: (1)..(119)
<223> OTHER INFORMATION: VH Comparison 1/Consensus

<400> SEQUENCE: 222

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Ser Tyr
                20                  25                  30

Gly Ile Ser Trp Val Arg Gln Ala Pro Gly His Gly Leu Glu Trp Met
            35                  40                  45

Gly Trp Ile Ser Ala Tyr Asn Gly Tyr Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser
            115

<210> SEQ ID NO 223
<211> LENGTH: 98
<212> TYPE: PRT
<213> ORGANISM: Mouse
<220> FEATURE:
<221> NAME/KEY: misc_feature
<222> LOCATION: (1)..(98)
<223> OTHER INFORMATION: IgHV1-69-4

<400> SEQUENCE: 223

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 224
<211> LENGTH: 121
<212> TYPE: PRT
<213> ORGANISM: Homo sapiens
<220> FEATURE:
<221> NAME/KEY: misc_feature
<222> LOCATION: (1)..(121)
<223> OTHER INFORMATION: VH Comparison 2/Consensus

<400> SEQUENCE: 224

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Gly Ile Gly Trp Val Arg Gln Ala Pro Gly Gln Gly Leu Glu Trp Met
            35                  40                  45

Gly Arg Ile Phe Pro Ile Leu Gly Thr Ala Asn Tyr Ala Gln Met Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Tyr Asp Ser Ala Asp Ala Phe Asp Ile Trp Gly
                100                 105                 110

Gln Gly Thr Met Val Thr Val Ser Ser
            115                 120

<210> SEQ ID NO 225
<211> LENGTH: 98
<212> TYPE: PRT
<213> ORGANISM: Mouse
<220> FEATURE:
<221> NAME/KEY: misc_feature
<222> LOCATION: (1)..(98)
<223> OTHER INFORMATION: IgHV3-30-3-1

<400> SEQUENCE: 225

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 226
<211> LENGTH: 98
<212> TYPE: PRT
<213> ORGANISM: Mouse
<220> FEATURE:
<221> NAME/KEY: misc_feature
<222> LOCATION: (1)..(98)
<223> OTHER INFORMATION: IgHV3-23-1

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 227
<211> LENGTH: 117
<212> TYPE: PRT
<213> ORGANISM: Homo sapiens
<220> FEATURE:
<221> NAME/KEY: misc_feature
<222> LOCATION: (1)..(117)
<223> OTHER INFORMATION: VH Comparison 4/Consensus

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Arg Gly Trp Gly Ser Asp Tyr Trp Gly Gln Gly Thr Leu
            100                 105                 110

Val Thr Val Ser Ser
        115

<210> SEQ ID NO 228
<211> LENGTH: 99
<212> TYPE: PRT
<213> ORGANISM: Mouse
<220> FEATURE:
<221> NAME/KEY: misc_feature
<222> LOCATION: (1)..(99)
<223> OTHER INFORMATION: IgHV4-30-2-1

<400> SEQUENCE: 228

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 229
<211> LENGTH: 98
<212> TYPE: PRT
<213> ORGANISM: Mouse
<220> FEATURE:
<221> NAME/KEY: misc_feature
<222> LOCATION: (1)..(98)
<223> OTHER INFORMATION: IgHV5-51-1

<400> SEQUENCE: 229

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 230
<211> LENGTH: 107
<212> TYPE: PRT
<213> ORGANISM: Mouse
```

```
<220> FEATURE:
<221> NAME/KEY: misc_feature
<222> LOCATION: (1)..(107)
<223> OTHER INFORMATION: IGKV1-12*01

<400> SEQUENCE: 230

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 231
<211> LENGTH: 107
<212> TYPE: PRT
<213> ORGANISM: Mouse
<220> FEATURE:
<221> NAME/KEY: misc_feature
<222> LOCATION: (1)..(107)
<223> OTHER INFORMATION: IGKVD-16*01

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 232
<211> LENGTH: 107
<212> TYPE: PRT
<213> ORGANISM: Mouse
<220> FEATURE:
<221> NAME/KEY: misc_feature
<222> LOCATION: (1)..(107)
<223> OTHER INFORMATION: IGKV3-11*01

<400> SEQUENCE: 232

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

-continued

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Phe
                 85                  90                  95

Thr Phe Gly Pro Gly Thr Lys Val Asp Ile Lys
                100                 105

<210> SEQ ID NO 233
<211> LENGTH: 107
<212> TYPE: PRT
<213> ORGANISM: Mouse
<220> FEATURE:
<221> NAME/KEY: misc_feature
<222> LOCATION: (1)..(107)
<223> OTHER INFORMATION: IGKV-13*02

<400> SEQUENCE: 233

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                 85                  90                  95

Thr Phe Gly Gln Gly Thr Lys Val Glu Ile Lys
                100                 105
```